(12) United States Patent
Shapiro et al.

(10) Patent No.: US 9,286,439 B2
(45) Date of Patent: Mar. 15, 2016

(54) SYSTEM AND METHOD FOR EDITING AND MANIPULATING DNA

(75) Inventors: Ehud Y. Shapiro, Nataf (IL); Shai Kaplan, Rehovot (IL); Gregory Linshiz, Rehovot (IL); Tuval Ben-Yehezkel, Ramat Gan (IL); Uri Shabi, Kfar Saba (IL)

(73) Assignee: YEDA RESEARCH AND DEVELOPMENT CO LTD, Rehovot (IL)

( * ) Notice: Subject to any disclaimer, the term of this patent is extended or adjusted under 35 U.S.C. 154(b) by 274 days.

(21) Appl. No.: 12/808,676

(22) PCT Filed: Dec. 17, 2008

(86) PCT No.: PCT/IL2008/001629
§ 371 (c)(1),
(2), (4) Date: Jul. 26, 2010

(87) PCT Pub. No.: WO2009/078016
PCT Pub. Date: Jun. 25, 2009

(65) Prior Publication Data
US 2010/0311598 A1 Dec. 9, 2010

Related U.S. Application Data

(60) Provisional application No. 61/006,042, filed on Dec. 17, 2007.

(51) Int. Cl.
*G06F 19/20* (2011.01)
*G06F 19/22* (2011.01)
*G06F 19/18* (2011.01)

(52) U.S. Cl.
CPC ............... *G06F 19/22* (2013.01); *G06F 19/18* (2013.01)

(58) Field of Classification Search
None
See application file for complete search history.

(56) References Cited

U.S. PATENT DOCUMENTS

| 5,804,373 | A | 9/1998 | Schweitzer et al. |
| 6,266,569 | B1 | 7/2001 | Shapiro et al. |
| 2002/0119458 | A1 | 8/2002 | Suyama et al. |
| 2004/0077090 | A1 | 4/2004 | Short |
| 2004/0152108 | A1 | 8/2004 | Keith et al. |
| 2004/0224345 | A1 | 11/2004 | Vandersall et al. |
| 2007/0161012 | A1 | 7/2007 | Alsheddi et al. |
| 2007/0250497 | A1 | 10/2007 | Mansfield et al. |

FOREIGN PATENT DOCUMENTS

| WO | 2006044956 | | 4/2006 |
| WO | 2007148337 | A2 | 12/2007 |
| WO | 2008045575 | A2 | 4/2008 |
| WO | 2008115626 | A2 | 9/2008 |
| WO | 2008157515 | A1 | 12/2008 |
| WO | 2009045581 | A2 | 4/2009 |

OTHER PUBLICATIONS

Kunkel, T. Rapid and efficient site-specific mutagenesis without phenotypic selection. Proc Nall Acad Sci U S A 82, 488-492 (1985).
Ho, S. et al., Site-directed mutagenesis by overlap extension using the polymerase chain reaction. Gene 77, 51-59 (1989).
Landt, O., et al. A general method for rapid site-directed mutagenesis using the polymerase chain reaction. Gene 96, 125-128 (1990).
Cirino, P., et al. Generating mutant libraries using error-prone PCR. Methods Mol Biol 231, 3-9 (2003).
Stemmer, W, et al. Single-step assembly of a gene and entire plasmid from large numbers of oligodeoxyribonucleotides. Gene 164, 49-53 (1995).
Wilson, G. Cloned restriction-modification systems—a review. Gene 74, 281-289 (1988).
Wilson, G. et al. Restriction and modification systems. Annu Rev Genet 25, 585-627 (1991).
Hartley, J., et al. DNA cloning using in vitro site-specific recombination. Genome Res 10, 1788-1795 (2000).
Li, M. et al. Harnessing homologous recombination in vitro to generate recombinant DNA via SLIC. Nat Methods 4, 251-256 (2007).
Au, L., et al. Gene synthesis by a LCR-based approach: high-level production of leptin-L54 using synthetic gene in *Escherichia coli*. Biochem Biophys Res Commun 248, 200-203 (1998).
Smith, H., et al. Generating a synthetic genome by whole genome assembly: phiX174 bacteriophage from synthetic oligonucleotides. Proc Natl Acad Sci U S A 100, 15440-15445 (2003).
Xiong, A. et al. PCR-based accurate synthesis of long DNA sequences. Nat Protoc 1, 791-797 (2006).
Horton, R., et al. Engineering hybrid genes without the use of restriction enzymes: gene splicing by overlap extension. Gene 77, 61-68 (1989).
Coco, W. et al. DNA shuffling method for generating highly recombined genes and evolved enzymes. Nat Biotechnol 19, 354-359 (2001).
Gaytán, P., et al. Combination of DMT-mononucleotide and Fmoc-trinucleotide phosphoramidites in oligonucleotide synthesis affords an automatable codon-level mutagenesis method. Chem Biol 5, 519-45 527 (1998).
Merkle, R.C. Convergent assembly. Nanotechnology 8, 18-22 (1997).
Xiong, A.S. et al. A simple, rapid, high-fidelity and cost-effective PCR-based two-step DNA synthesis method for long gene sequences. Nucleic Acids Res 32, e98 (2004).
Tian et al., Accurate multiplex gene synthesis from programmable DNA microchips. Nature 432(7020):1050-4 (2004).
International search report and written opinion for PCT/IL2008/001629 dated Jul. 23, 2009.
PCT Search Report for PCT/IL2007/000747 transmitted on Aug. 13, 2008.
IPRP for PCT/IL2007/000747 transmitted on Mar. 17, 2009.

(Continued)

*Primary Examiner* — Catherine S Hibbert
(74) *Attorney, Agent, or Firm* — Graeser Associates International Inc; Dvorah Graeser

(57) ABSTRACT

A system and method for planning, manipulating, processing and editing DNA molecules utilizing a core operation on a given input DNA molecule to produce a targeted DNA molecule.

16 Claims, 17 Drawing Sheets

(56) References Cited

OTHER PUBLICATIONS

Supplementary Search Report for EP application 07736483.4 transmitted on Feb. 16, 2010.
Office Action for EP application 07736483.4 issued on Jun. 8, 2011.
Kodumal et al., 2004, PNAS, Total synthesis of long DNA sequences: Synthesis of a contiguous 32-kb polyketide synthase gene cluster.
Yingfeng An et al: "A rapid and efficient method for multiple-site mutagenesis with a modified overlap extension PCR", Apple Microsoft (2005) 68:774-778.
Hoover et al., 2002, Nucleic Acid Research, DNAWorks: an automated method for designing oligonucleotides for PCR-based gene synthesis.
Yee et al., 1998, Proceedings international conference on intelligent systems for molecular biology, Automated clustering and assembly of large EST collections.
Adelman Leonard M., 1994, Science, Molecular Computation of Solutions to Combinatorial Problems.
Braich et al., 2001, DNA Computing—Lecture Notes in Computer Science, Solution of a Satisfiability Problem on a Gel-Based DNA Computer.
Braich et al., 2002, Science, Solution of a 20-Variable 3-SAT Problem on a DNA Computer.
Ben Yehezkel et al., 2008, Nucleic Acid Research, De novo DNA synthesis using single molecule PCR.
Barany F., 1991, PNAS, Genetic disease detection and DNA amplification using cloned thermostable ligase.
Linshiz Gregory et al: "Recursive constrction of perfect DNA molecules from imperfect oligonucleotides", Molecular Systems Biology, vol. 4, May 2008, pp. Article No. 191 URL-HTTP:// WW,xp002568816, ISSN: 1744-4292 (PRINT) 1744-4292.
Binkowski B Fetal: "Correcting errors in synthetic DNA through consensus shuffling", Nucleic Acids Research Special Publication, Oxford University Press, Surrey, GB, vol. 33, No. 6, Mar. 30, 2005, pp. 1-8, XP002368229, ISSN: 0305-1048, DOI: 10.1093/ NAR!GNI053.
Carr P A et al: "Protein-mediated error correction for de novo DNA synthesis", Nucleic Acids Research Special Publication, Oxford University Press, Surrey, GB, vol. 32, No. 20, Nov. 23, 2004, pp. 1-9, XP002368230, ISSN: 0305-1048, DOI: 10.1093/NAR/GKH560.
Office Action for related EP application 07736483.4 issued on Mar. 8, 2012.
Office Action for related EP application 07736483.4 issued on Jun. 8, 2011.
Office Action for related EP application 12167464 issued on Oct. 23, 2013.
Office Action for related EP application 12167464 issued on Apr. 8, 2013.
Office action for related EP application 12167464 issued on Jun. 28, 2012.
Office Action for related Israel application 196013 issued on Mar. 12, 2012.
Office Action for related Israel application 196013 issued on Aug. 18, 2013.
Office Action for related EP application 12167464 issued on Jun. 30, 2014.
Office Action for related Israel application 196013 issued on Jun. 5, 2014.
Office Action for related Israel application 206439 issued on Mar. 20, 2014.
PCT search report for PCT Application No. PCT/IB2009/052508, mailed Mar. 2 2010.
Diehl et al, Nature Methods, vol. 3, No. 7, Jul. 1, 2006, pp. 551-559.
Margulies et al, Nature, vol. 437, No. 7057, Sep. 15, 2005, pp. 376-380.
Dressman et al, PNAS, vol. 100, No. 15, Jul. 22, 2003, pp. 8817-8822.
Hofreiter et al, COMPTES RENDUS-PALEVOL, vol. 7, No. 2-3, Apr. 1, 2008, pp. 113-124.
Higuchi RG, Ochman H. 1989. Production of single stranded DNA templates by exonuclease digestion following the PCR. Nucleic Acids Res 17:5865.

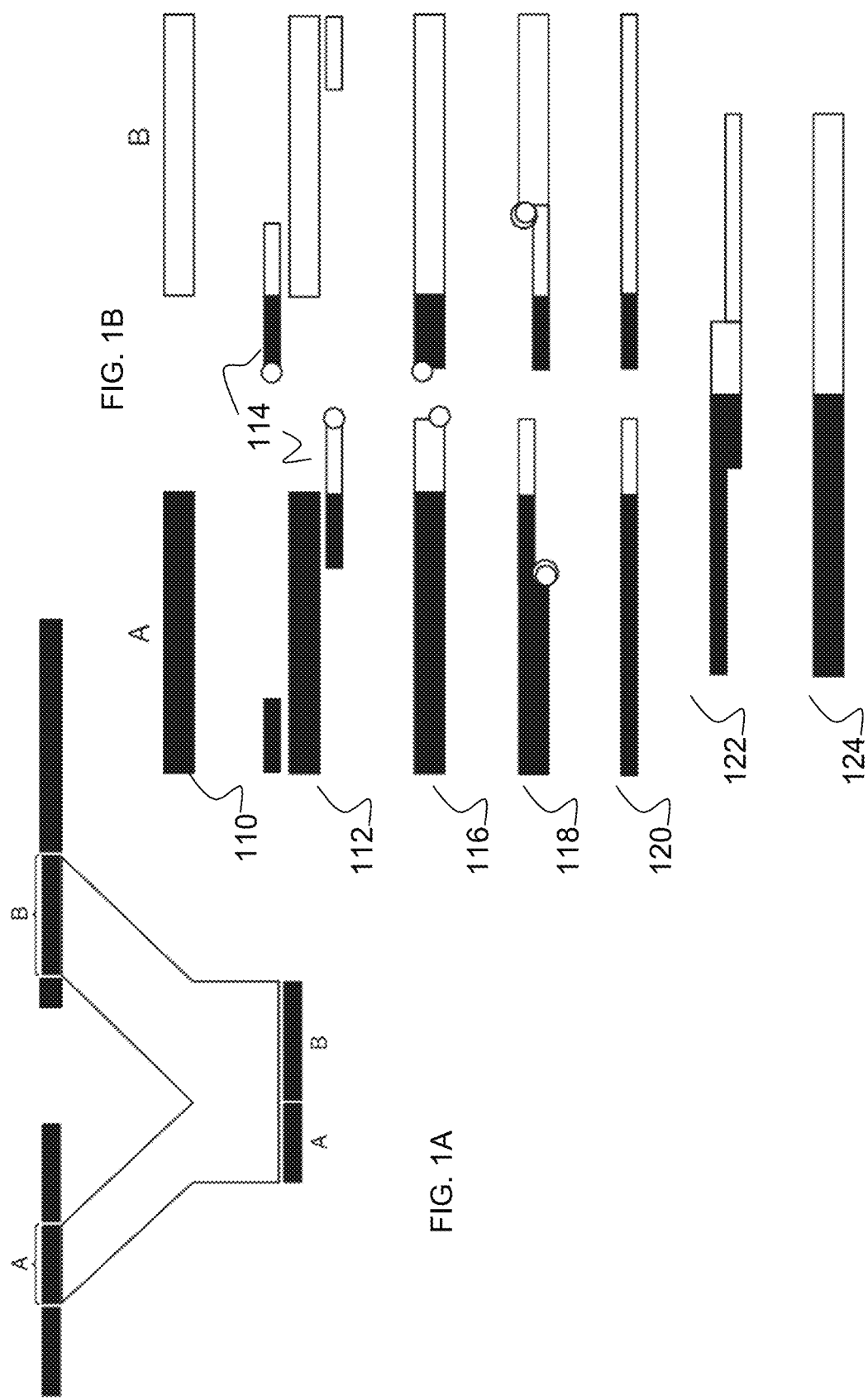

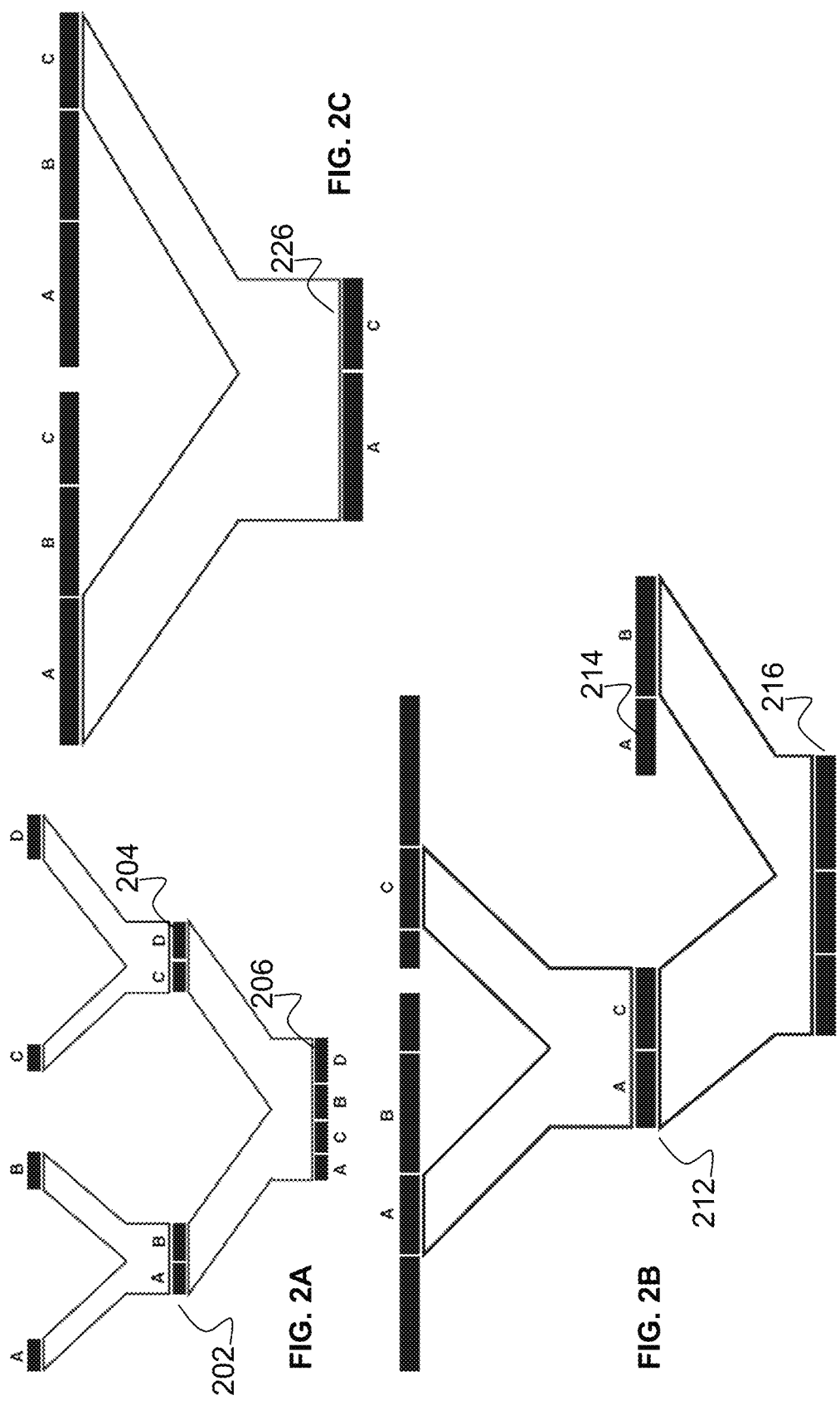

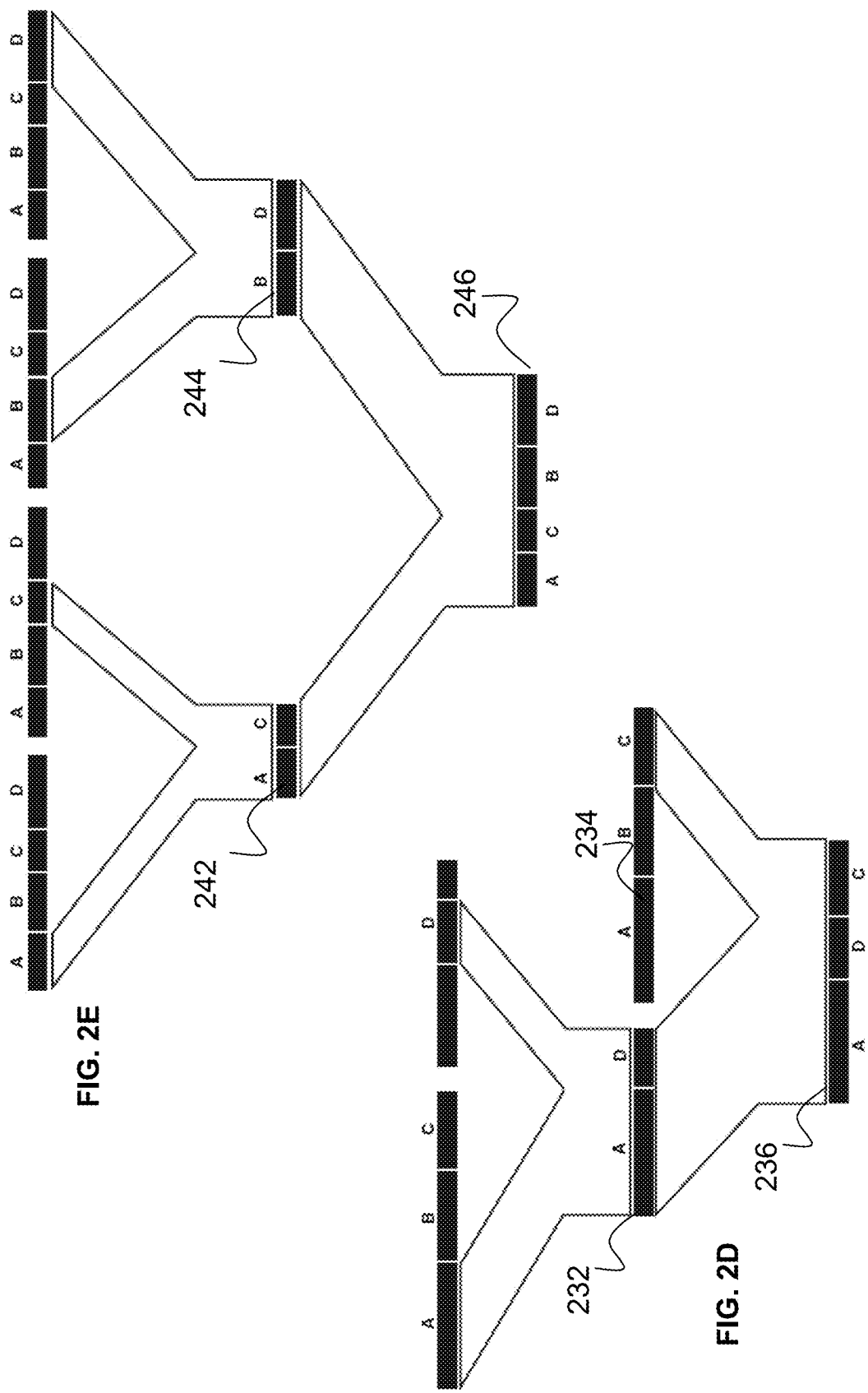

SEQUENCE LISTING

```
<160> NUMBER OF SEQ ID NOS: 143

<210> SEQ ID NO 1
<211> LENGTH: 704
<212> TYPE: DNA
<213> ORGANISM: artificial
<220> FEATURE:
<223> OTHER INFORMATION: synthetic molecule constructed according to the
      described algorithm

<400> SEQUENCE: 1
atcgacccgg gcatttatat tgaattttca aaaattctta ctttttttt ggatggacgc      60 aaagaagttt aataatcata ttacatggca ttaccaccat atacatatcc atatctaatc    120
ttacttatat gttgtggaaa tgtaaagagc cccattatct tagcctaaaa aaaccttctc    180
tttggaactt tcagtaatac gcttaactgc tcattgctat attgaagtac ggattagaag    240
ccgccgagcg ggcgacagcc ctccgacgga agactctcct ccgtgcgtcc tcgtcttcac    300
cggtcgcgtt cctgaaacgc agatgtgcct cgcgccgcac tgctccgaac aataaagatt    360
ctacaatact agcttttatg gttatgaaga ggaaaaattg gcagtaacct ggccccacaa    420
accttcaaat taacgaatca aattaacaac cataggatga taatgcgatt agtttttag    480 ccttatttct ggggtaatta atcagcgaag cgatgatttt tgatctatta acagatatat    540
aaatggaaaa gctgcataac cactttaact aatactttca acattttcag tttgtattac    600
ttcttattca aatgtcataa aagtatcaac aaaaaattgt taatatacct ctatacttta    660
acgtcaagga gaaaaaacta taatgttaat taaggatcca tcga                    704

<210> SEQ ID NO 2
<211> LENGTH: 150
<212> TYPE: DNA
<213> ORGANISM: artificial
<220> FEATURE:
<223> OTHER INFORMATION: synthetic molecule constructed according to the
      described algorithm

<400> SEQUENCE: 2
cctttcttct ctcccctgca atataatagt ttaattctaa tattaataat atcctatatt      60
ttcttcattt accggcgcac tctcgcccga acgacctcaa aatgtctgct acattcataa    120
taaccaaaag ctcataactt ttttttttga                                    150

<210> SEQ ID NO 3
```

```
<211> LENGTH: 774
<212> TYPE: DNA
<213> ORGANISM: artificial
<220> FEATURE:
<223> OTHER INFORMATION: synthetic molecule constructed according to the
      described algorithm

<400> SEQUENCE: 3
atcgacccgg gcatttatat tgaattttca aaaattctta cttttttttt ggatggacgc    60
aaagaagttt aataatcata ttacatggca ttaccaccat atacatatcc atatctaatc   120
ttacttatat gttgtggaaa tgtaaagagc cccattatct tagcctaaaa aaaccttctc   180
tttggaactt tcagtaatac gcttaactgc tcattgctat attgaagtac ggattagaag   240
ccgccgagcg ggcgacagcc ctccgacgga agactctcct ccgtgcgtcc tcgtcttcac   300
cggtcgcgtt cctgaaacgc agatgtgcct cgcgccgcac tgctccgtcc acaacatata   360
agtaagatta gatatggata tgtatatggt ggtaatgcca tgtaatatga ttattaaaac   420
aataaagatt ctacaatact agcttttatg gttatgaaga ggaaaaattg gcagtaacct   480
ggccccacaa accttcaaat taacgaatca aattaacaac cataggatga taatgcgatt   540
agttttttag ccttatttct ggggtaatta atcagcgaag cgatgatttt tgatctatta   600
acagatatat aaatggaaaa gctgcataac cactttaact aatactttca acattttcag   660
tttgtattac ttcttattca aatgtcataa aagtatcaac aaaaaattgt taatatacct   720
ctatacttta acgtcaagga gaaaaaacta taatgttaat taaggatcca tcga         774

<210> SEQ ID NO 4
<211> LENGTH: 586
<212> TYPE: DNA
<213> ORGANISM: artificial
<220> FEATURE:
<223> OTHER INFORMATION: synthetic molecule constructed according to the
      described algorithm

<400> SEQUENCE: 4
atcgacccgg gcatttatat tgaattttca aaaattctta cttttttttt ggatggacgc    60
aaagaagttt aataatcata ttacatggca ttaccaccat atacatatcc atatctaatc   120
ttacttatat gttgtggaaa tgtaaagagc cccattatct tagcctaaaa aaaccttctc   180
tttggaactt tcagtaatac gcttaactgc tcattgctat attgaagtaa acaataaaga   240
ttctacaata ctagctttta tggttatgaa gaggaaaaat tggcagtaac ctggccccac   300
aaaccttcaa attaacgaat caaattaaca accataggat gataatgcga ttagtttttt   360
agccttattt ctggggtaat taatcagcga agcgatgatt tttgatctat taacagatat   420
ataaatggaa aagctgcata accactttaa ctaatacttt caacattttc agtttgtatt   480
acttcttatt caaatgtcat aaaagtatca acaaaaaatt gttaatatac ctctatactt   540
taacgtcaag gagaaaaaac tataatgtta attaaggatc catcga                  586

<210> SEQ ID NO 5
<211> LENGTH: 704
<212> TYPE: DNA
<213> ORGANISM: artificial
<220> FEATURE:
<223> OTHER INFORMATION: synthetic molecule constructed according to the
      described algorithm

<400> SEQUENCE: 5
atcgacccgg gcatttatat tgaattttca aaaattctta cttttttttt ggatggacgc    60
```

```
aaagaagttt aataatcata ttacatggca ttaccaccat atacatatcc atatctaatc    120
ttacttatat gttgtggaaa tgtaaagagc cccattatct tagcctaaaa aaaccttctc    180
tttggaactt tcagtaatac gcttaactgc tcattgctat attgaagtaa acaataaaga    240
ttctacaata ctagctttta tggttatgaa gaggaaaaat tggcagtaac ctggccccac    300
aaaccttcaa attaacgaat caaattaaca accataggat gataatgcga ttagtttttt    360
agccttattt ctggggtaat taatcagcga agcgatgatt tttgatctat taacggatta    420
gaagccgccg agcgggcgac agccctccga cggaagactc tcctccgtgc gtcctcgtct    480
tcaccggtcg cgttcctgaa acgcagatgt gcctcgcgcc gcactgctcc gcagatatat    540
aaatggaaaa gctgcataac cactttaact aatactttca acattttcag tttgtattac    600
ttcttattca aatgtcataa aagtatcaac aaaaaattgt taatataccct ctatacttta    660 acgtcaagga gaaaaaacta taatgttaat taaggatcca tcga                     704
```

<210> SEQ ID NO 6
<211> LENGTH: 822
<212> TYPE: DNA
<213> ORGANISM: artificial
<220> FEATURE:
<223> OTHER INFORMATION: synthetic molecule constructed according to the described algorithm

<400> SEQUENCE: 6

```
atcgacccgg gcatttatat tgaattttca aaaattctta cttttttttt ggatggacgc     60
aaagaagttt aataatcata ttacatggca ttaccaccat atacatatcc atatctaatc    120
ttacttatat gttgtggaaa tgtaaagagc cccattatct tagcctaaaa aaaccttctc    180
tttggaactt tcagtaatac gcttaactgc tcattgctat attgaagtac ggattagaag    240
ccgccgagcg ggcgacagcc ctccgacgga agactctcct ccgtgcgtcc tcgtcttcac    300
cggtcgcgtt cctgaaacgc agatgtgcct cgcgccgcac tgctccgaac aataaagatt    360
ctacaatact agcttttatg gttatgaaga ggaaaaattg gcagtaacct ggccccacaa    420
accttcaaat taacgaatca aattaacaac cataggatga taatgcgatt agttttttag    480
ccttatttct ggggtaatta atcagcgaag cgatgatttt tgatctatta acggattaga    540
agccgccgag cgggcgacag ccctccgacg gaagactctc ctccgtgcgt cctcgtcttc    600
accggtcgcg ttcctgaaac gcagatgtgc ctcgcgccgc actgctccgc agatatataa    660
atggaaaagc tgcataacca ctttaactaa tactttcaac attttcagtt tgtattactt    720
cttattcaaa tgtcataaaa gtatcaacaa aaaattgtta atatacctct atactttaac    780
gtcaaggaga aaaactata atgttaatta aggatccatc ga                        822
```

<210> SEQ ID NO 7
<211> LENGTH: 736
<212> TYPE: DNA
<213> ORGANISM: artificial
<220> FEATURE:
<223> OTHER INFORMATION: synthetic molecule constructed according to the described algorithm

<400> SEQUENCE: 7

```
atcgacccgg gcatttatat tgaattttca aaaattctta cttttttttt ggatggacgc     60
aaagaagttt aataatcata ttacatggca ttaccaccat atacatatcc atatctaatc    120
ttacttatat gttgtggaaa tgtaaagagc cccattatct tagcctaaaa aaaccttctc    180
tttggaactt tcagtaatac gcttaactgc tcattgctat attgaagtac ctttcttctc    240
```

```
tcccctgcaa tataatagtt taattctaat attaataata tcctatattt tcttcattta    300
ccggcgcact ctcgcccgaa cgacctcaaa atgtctgcta cattcataat aaccaaaagc    360
tcataacttt ttttttgaa acaataaaga ttctacaata ctagctttta tggttatgaa     420
gaggaaaaat tggcagtaac ctggccccac aaaccttcaa attaacgaat caaattaaca    480
accataggat gataatgcga ttagtttttt agccttattt ctggggtaat taatcagcga    540
agcgatgatt tttgatctat taacagatat ataaatggaa aagctgcata accactttaa    600
ctaatacttt caacattttc agtttgtatt acttcttatt caaatgtcat aaaagtatca    660
acaaaaaatt gttaatatac ctctatactt taacgtcaag gagaaaaaac tataatgtta    720
attaaggatc catcga                                                    736
```

<210> SEQ ID NO 8
<211> LENGTH: 21
<212> TYPE: DNA
<213> ORGANISM: artificial
<220> FEATURE:
<223> OTHER INFORMATION: synthetic molecule constructed according to the
      described algorithm

<400> SEQUENCE: 8
atcgacccgg gcatttatat t                                              21

<210> SEQ ID NO 9
<211> LENGTH: 27
<212> TYPE: DNA
<213> ORGANISM: artificial
<220> FEATURE:
<223> OTHER INFORMATION: synthetic molecule constructed according to the
      described algorithm

<400> SEQUENCE: 9
tcgatggatc cttaattaac attatag                                        27

<210> SEQ ID NO 10
<211> LENGTH: 21
<212> TYPE: DNA
<213> ORGANISM: artificial
<220> FEATURE:
<223> OTHER INFORMATION: synthetic molecule constructed according to the
      described algorithm

<400> SEQUENCE: 10
gtggacggag cagtgcggcg c                                              21

<210> SEQ ID NO 11
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 11
cgccgcactg ctccgtccac aacatataag taagattaga tatggata                 48

<210> SEQ ID NO 12
<211> LENGTH: 33
<212> TYPE: DNA
<213> ORGANISM: artificial
<220> FEATURE:
<223> OTHER INFORMATION: synthetic molecule constructed according to the
      described algorithm

```
<400> SEQUENCE: 12
tccacaacat ataagtaaga ttagatatgg ata                             33

<210> SEQ ID NO 13
<211> LENGTH: 28
<212> TYPE: DNA
<213> ORGANISM: artificial
<220> FEATURE:
<223> OTHER INFORMATION: synthetic molecule constructed according to the
      described algorithm

<400> SEQUENCE: 13
tcgatggatc cttaattaac attatagt                                   28

<210> SEQ ID NO 14
<211> LENGTH: 39
<212> TYPE: DNA
<213> ORGANISM: artificial
<220> FEATURE:
<223> OTHER INFORMATION: synthetic molecule constructed according to the
      described algorithm

<400> SEQUENCE: 14
ctttattgtt ttaataatca tattcatgg cattaccac                        39

<210> SEQ ID NO 15
<211> LENGTH: 64
<212> TYPE: DNA
<213> ORGANISM: artificial
<220> FEATURE:
<223> OTHER INFORMATION: synthetic molecule constructed according to the
      described algorithm

<400> SEQUENCE: 15
tgtatatggt ggtaatgcca tgtaatatga ttattaaaac aataaagatt ctacaatact    60
agct                                                             64

<210> SEQ ID NO 16
<211> LENGTH: 70
<212> TYPE: DNA
<213> ORGANISM: artificial
<220> FEATURE:
<223> OTHER INFORMATION: synthetic molecule constructed according to the
      described algorithm

<400> SEQUENCE: 16
tccacaacat ataagtaaga ttagatatgg atatgtatat ggtggtaatg ccatgtaata    60
tgattattaa                                                       70

<210> SEQ ID NO 17
<211> LENGTH: 33
<212> TYPE: DNA
<213> ORGANISM: artificial
<220> FEATURE:
<223> OTHER INFORMATION: synthetic molecule constructed according to the
      described algorithm

<400> SEQUENCE: 17
ctttattgtt tacttcaata tagcaatgag cag                             33

<210> SEQ ID NO 18
<211> LENGTH: 55
<212> TYPE: DNA
<213> ORGANISM: artificial
```

```
<220> FEATURE:
<223> OTHER INFORMATION: synthetic molecule constructed according to the
      described algorithm

<400> SEQUENCE: 18
cttaactgct cattgctata ttgaagtaaa caataaagat tctacaatac tagct          55

<210> SEQ ID NO 19
<211> LENGTH: 36
<212> TYPE: DNA
<213> ORGANISM: artificial
<220> FEATURE:
<223> OTHER INFORMATION: synthetic molecule constructed according to the
      described algorithm

<400> SEQUENCE: 19
ttctaatccg ttaatagatc aaaaatcatc gcttcg                               36

<210> SEQ ID NO 20
<211> LENGTH: 41
<212> TYPE: DNA
<213> ORGANISM: artificial
<220> FEATURE:
<223> OTHER INFORMATION: synthetic molecule constructed according to the
      described algorithm

<400> SEQUENCE: 20
gaagcgatga tttttgatct attaacggat tagaagccgc c                         41

<210> SEQ ID NO 21
<211> LENGTH: 25
<212> TYPE: DNA
<213> ORGANISM: artificial
<220> FEATURE:
<223> OTHER INFORMATION: synthetic molecule constructed according to the
      described algorithm

<400> SEQUENCE: 21
atcgacccgg gcatttatat tgaat                                           25

<210> SEQ ID NO 22
<211> LENGTH: 25
<212> TYPE: DNA
<213> ORGANISM: artificial
<220> FEATURE:
<223> OTHER INFORMATION: synthetic molecule constructed according to the
      described algorithm

<400> SEQUENCE: 22
taatagatca aaaatcatcg cttcg                                           25

<210> SEQ ID NO 23
<211> LENGTH: 17
<212> TYPE: DNA
<213> ORGANISM: artificial
<220> FEATURE:
<223> OTHER INFORMATION: synthetic molecule constructed according to the
      described algorithm

<400> SEQUENCE: 23
acggattaga agccgcc                                                    17

<210> SEQ ID NO 24
<211> LENGTH: 27
<212> TYPE: DNA
<213> ORGANISM: artificial
<220> FEATURE:
```

<223> OTHER INFORMATION: synthetic molecule constructed according to the
      described algorithm

<400> SEQUENCE: 24
ttatatatct gcggagcagt gcggcgc                                              27

<210> SEQ ID NO 25
<211> LENGTH: 37
<212> TYPE: DNA
<213> ORGANISM: artificial
<220> FEATURE:
<223> OTHER INFORMATION: synthetic molecule constructed according to the
      described algorithm

<400> SEQUENCE: 25
ccgcactgct ccgcagatat ataaatggaa aagctgc                                   37

<210> SEQ ID NO 26
<211> LENGTH: 34
<212> TYPE: DNA
<213> ORGANISM: artificial
<220> FEATURE:
<223> OTHER INFORMATION: synthetic molecule constructed according to the
      described algorithm

<400> SEQUENCE: 26
gagaagaaag gtacttcaat atagcaatga gcag                                      34

<210> SEQ ID NO 27
<211> LENGTH: 41
<212> TYPE: DNA
<213> ORGANISM: artificial
<220> FEATURE:
<223> OTHER INFORMATION: synthetic molecule constructed according to the
      described algorithm

<400> SEQUENCE: 27
gctcattgct atattgaagt acctttcttc tctcccctgc a                              41

<210> SEQ ID NO 28
<211> LENGTH: 22
<212> TYPE: DNA
<213> ORGANISM: artificial
<220> FEATURE:
<223> OTHER INFORMATION: synthetic molecule constructed according to the
      described algorithm

<400> SEQUENCE: 28
aaagatacca ttgcgctggt gg                                                   22

<210> SEQ ID NO 29
<211> LENGTH: 28
<212> TYPE: DNA
<213> ORGANISM: artificial
<220> FEATURE:
<223> OTHER INFORMATION: synthetic molecule constructed according to the
      described algorithm

<400> SEQUENCE: 29
ttgtttcaca actaacttca ggtctacg                                             28

<210> SEQ ID NO 30
<211> LENGTH: 28
<212> TYPE: DNA
<213> ORGANISM: artificial
<220> FEATURE:
<223> OTHER INFORMATION: synthetic molecule constructed according to the -continued described algorithm

<400> SEQUENCE: 30
tcccgggcat cgcttgtacc agcgatgc                                          28

<210> SEQ ID NO 31
<211> LENGTH: 29
<212> TYPE: DNA
<213> ORGANISM: artificial
<220> FEATURE:
<223> OTHER INFORMATION: synthetic molecule constructed according to the
      described algorithm

<400> SEQUENCE: 31
tggtacaagc gatgcccggg aatgggggg                                         29

<210> SEQ ID NO 32
<211> LENGTH: 18
<212> TYPE: DNA
<213> ORGANISM: artificial
<220> FEATURE:
<223> OTHER INFORMATION: synthetic molecule constructed according to the
      described algorithm

<400> SEQUENCE: 32
cgcttgtacc agcgatgc                                                     18

<210> SEQ ID NO 33
<211> LENGTH: 37
<212> TYPE: DNA
<213> ORGANISM: artificial
<220> FEATURE:
<223> OTHER INFORMATION: synthetic molecule constructed according to the
      described algorithm

<400> SEQUENCE: 33
tcggtaggat ctataagcaa gatttttgtc ccacgga                                37

<210> SEQ ID NO 34
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 34
tccgtgggac aaaaatcttg cttatagatc ctaccgactc agatgccg                    48

<210> SEQ ID NO 35
<211> LENGTH: 27
<212> TYPE: DNA
<213> ORGANISM: artificial
<220> FEATURE:
<223> OTHER INFORMATION: synthetic molecule constructed according to the
      described algorithm

<400> SEQUENCE: 35
ctataagcaa gattttgtc ccacgga                                            27

<210> SEQ ID NO 36
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 36
tcaaagagac ttcccacggt tcatttaacg tttcaacc                                    38

<210> SEQ ID NO 37
<211> LENGTH: 40
<212> TYPE: DNA
<213> ORGANISM: artificial
<220> FEATURE:
<223> OTHER INFORMATION: synthetic molecule constructed according to the
      described algorithm

<400> SEQUENCE: 37
cgttaaatga accgtgggaa gtctctttga aggacggcgc                                  40

<210> SEQ ID NO 38
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 38
aaagatacca ttgcgctggt ggttgaaacg ttaaatgaac cgtgggaa                         48

<210> SEQ ID NO 39
<211> LENGTH: 21
<212> TYPE: DNA
<213> ORGANISM: artificial
<220> FEATURE:
<223> OTHER INFORMATION: synthetic molecule constructed according to the
      described algorithm

<400> SEQUENCE: 39
atcctaccga ctcagatgcc g                                                      21

<210> SEQ ID NO 40
<211> LENGTH: 34
<212> TYPE: DNA
<213> ORGANISM: artificial
<220> FEATURE:
<223> OTHER INFORMATION: synthetic molecule constructed according to the
      described algorithm

<400> SEQUENCE: 40
gtacattgtc ttctgcaata tgggacacga cttc                                        34

<210> SEQ ID NO 41
<211> LENGTH: 45
<212> TYPE: DNA
<213> ORGANISM: artificial
<220> FEATURE:
<223> OTHER INFORMATION: synthetic molecule constructed according to the
      described algorithm

<400> SEQUENCE: 41
tcgtgtccca tattgcagaa gacaatgtac tcggtgggaa aatcg                            45

<210> SEQ ID NO 42
<211> LENGTH: 60
<212> TYPE: DNA
<213> ORGANISM: artificial
<220> FEATURE:
<223> OTHER INFORMATION: synthetic molecule constructed according to the
      described algorithm

<400> SEQUENCE: 42
ttctgcaata tgggacacga cttcgccctt agtggcctga tcatccagcg tgataacggg    60

<210> SEQ ID NO 43
<211> LENGTH: 26
<212> TYPE: DNA
<213> ORGANISM: artificial
<220> FEATURE:
<223> OTHER INFORMATION: synthetic molecule constructed according to the
      described algorithm

<400> SEQUENCE: 43
gatcatccag cgtgataacg ggaatg    26

<210> SEQ ID NO 44
<211> LENGTH: 18
<212> TYPE: DNA
<213> ORGANISM: artificial
<220> FEATURE:
<223> OTHER INFORMATION: synthetic molecule constructed according to the
      described algorithm

<400> SEQUENCE: 44
atgcccggga atgggggg    18

<210> SEQ ID NO 45
<211> LENGTH: 29
<212> TYPE: DNA
<213> ORGANISM: artificial
<220> FEATURE:
<223> OTHER INFORMATION: synthetic molecule constructed according to the
      described algorithm

<400> SEQUENCE: 45
tccggcaatt ctgctatagt ggccgccag    29

<210> SEQ ID NO 46
<211> LENGTH: 35
<212> TYPE: DNA
<213> ORGANISM: artificial
<220> FEATURE:
<223> OTHER INFORMATION: synthetic molecule constructed according to the
      described algorithm

<400> SEQUENCE: 46
ggccactata gcagaattgc cggatcagat cggtg    35

<210> SEQ ID NO 47
<211> LENGTH: 18
<212> TYPE: DNA
<213> ORGANISM: artificial
<220> FEATURE:
<223> OTHER INFORMATION: synthetic molecule constructed according to the
      described algorithm

<400> SEQUENCE: 47
tgctatagtg gccgccag    18

<210> SEQ ID NO 48
<211> LENGTH: 30
<212> TYPE: DNA
<213> ORGANISM: artificial
<220> FEATURE:
<223> OTHER INFORMATION: synthetic molecule constructed according to the
      described algorithm

<400> SEQUENCE: 48

-continued tttcatcttc ttgggcgaac acagcctgta                                    30

<210> SEQ ID NO 49
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 49
gctgtgttcg cccaagaaga tgaaatggca ctgggtgc                           38

<210> SEQ ID NO 50
<211> LENGTH: 20
<212> TYPE: DNA
<213> ORGANISM: artificial
<220> FEATURE:
<223> OTHER INFORMATION: synthetic molecule constructed according to the
      described algorithm

<400> SEQUENCE: 50
ttgggcgaac acagcctgta                                               20

<210> SEQ ID NO 51
<211> LENGTH: 29
<212> TYPE: DNA
<213> ORGANISM: artificial
<220> FEATURE:
<223> OTHER INFORMATION: synthetic molecule constructed according to the
      described algorithm

<400> SEQUENCE: 51
ttcgatcatc gtctgccggt tgagaggct                                     29

<210> SEQ ID NO 52
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 52
tcaaccggca gacgatgatc gaattaaggg cctgaatg                           38

<210> SEQ ID NO 53
<211> LENGTH: 36
<212> TYPE: DNA
<213> ORGANISM: artificial
<220> FEATURE:
<223> OTHER INFORMATION: synthetic molecule constructed according to the
      described algorithm

<400> SEQUENCE: 53
atgcccggga atgggggag ggatttcaac aggcag                              36

<210> SEQ ID NO 54
<211> LENGTH: 19
<212> TYPE: DNA
<213> ORGANISM: artificial
<220> FEATURE:
<223> OTHER INFORMATION: synthetic molecule constructed according to the
      described algorithm

<400> SEQUENCE: 54

```
gtctgccggt tgagaggct                                                      19
```

<210> SEQ ID NO 55
<211> LENGTH: 27
<212> TYPE: DNA
<213> ORGANISM: artificial
<220> FEATURE:
<223> OTHER INFORMATION: synthetic molecule constructed according to the
      described algorithm

<400> SEQUENCE: 55

```
gatgatcgaa ttaagggcct gaatgtt                                             27
```

<210> SEQ ID NO 56
<211> LENGTH: 24
<212> TYPE: DNA
<213> ORGANISM: artificial
<220> FEATURE:
<223> OTHER INFORMATION: synthetic molecule constructed according to the
      described algorithm

<400> SEQUENCE: 56

```
gaagatgaaa tggcactggg tgcg                                                24
```

<210> SEQ ID NO 57
<211> LENGTH: 40
<212> TYPE: DNA
<213> ORGANISM: artificial
<220> FEATURE:
<223> OTHER INFORMATION: synthetic molecule constructed according to the
      described algorithm

<400> SEQUENCE: 57

```
tcaaccggca gacgatgatc gaattaaggg cctgaatgtt                               40
```

<210> SEQ ID NO 58
<211> LENGTH: 39
<212> TYPE: DNA
<213> ORGANISM: artificial
<220> FEATURE:
<223> OTHER INFORMATION: synthetic molecule constructed according to the
      described algorithm

<400> SEQUENCE: 58

```
gctgtgttcg cccaagaaga tgaaatggca ctgggtgcg                                39
```

<210> SEQ ID NO 59
<211> LENGTH: 33
<212> TYPE: DNA
<213> ORGANISM: artificial
<220> FEATURE:
<223> OTHER INFORMATION: synthetic molecule constructed according to the
      described algorithm

<400> SEQUENCE: 59

```
ttagtggcct gatcatccag cgtgataacg gga                                      33
```

<210> SEQ ID NO 60
<211> LENGTH: 31
<212> TYPE: DNA
<213> ORGANISM: artificial
<220> FEATURE:
<223> OTHER INFORMATION: synthetic molecule constructed according to the
      described algorithm

<400> SEQUENCE: 60

```
acgctggatg atcaggccac taagggcgaa g                                        31
```

<210> SEQ ID NO 61
<211> LENGTH: 36
<212> TYPE: DNA
<213> ORGANISM: artificial
<220> FEATURE:
<223> OTHER INFORMATION: synthetic molecule constructed according to the
      described algorithm

<400> SEQUENCE: 61
cggtaggatc tataagcaag attttttgtcc cacgga                              36

<210> SEQ ID NO 62
<211> LENGTH: 43
<212> TYPE: DNA
<213> ORGANISM: artificial
<220> FEATURE:
<223> OTHER INFORMATION: synthetic molecule constructed according to the
      described algorithm

<400> SEQUENCE: 62
gggacaaaaa tcttgcttat agatcctacc gactcagatg ccg                      43

<210> SEQ ID NO 63
<211> LENGTH: 26
<212> TYPE: DNA
<213> ORGANISM: artificial
<220> FEATURE:
<223> OTHER INFORMATION: synthetic molecule constructed according to the
      described algorithm

<400> SEQUENCE: 63
tataagcaag attttttgtcc cacgga                                        26

<210> SEQ ID NO 64
<211> LENGTH: 25
<212> TYPE: DNA
<213> ORGANISM: artificial
<220> FEATURE:
<223> OTHER INFORMATION: synthetic molecule constructed according to the
      described algorithm

<400> SEQUENCE: 64
atcatccagc gtgataacgg gaatg                                          25

<210> SEQ ID NO 65
<211> LENGTH: 22
<212> TYPE: DNA
<213> ORGANISM: artificial
<220> FEATURE:
<223> OTHER INFORMATION: synthetic molecule constructed according to the
      described algorithm

<400> SEQUENCE: 65
atccagcgtg ataacgggaa tg                                             22

<210> SEQ ID NO 66
<211> LENGTH: 19
<212> TYPE: DNA
<213> ORGANISM: artificial
<220> FEATURE:
<223> OTHER INFORMATION: synthetic molecule constructed according to the
      described algorithm

<400> SEQUENCE: 66
caggccacta agggcgaag                                                 19

```
<210> SEQ ID NO 67
<211> LENGTH: 34
<212> TYPE: DNA
<213> ORGANISM: artificial
<220> FEATURE:
<223> OTHER INFORMATION: synthetic molecule constructed according to the
      described algorithm

<400> SEQUENCE: 67
gcccgggaat gggggagggg atttcaacag gcag                                34

<210> SEQ ID NO 68
<211> LENGTH: 18
<212> TYPE: DNA
<213> ORGANISM: artificial
<220> FEATURE:
<223> OTHER INFORMATION: synthetic molecule constructed according to the
      described algorithm

<400> SEQUENCE: 68
tcccgggcat cgcttgta                                                  18

<210> SEQ ID NO 69
<211> LENGTH: 35
<212> TYPE: DNA
<213> ORGANISM: artificial
<220> FEATURE:
<223> OTHER INFORMATION: synthetic molecule constructed according to the
      described algorithm

<400> SEQUENCE: 69
ccctcgccgg cctttttcgc tatgtaatct ccagc                               35

<210> SEQ ID NO 70
<211> LENGTH: 34
<212> TYPE: DNA
<213> ORGANISM: artificial
<220> FEATURE:
<223> OTHER INFORMATION: synthetic molecule constructed according to the
      described algorithm

<400> SEQUENCE: 70
tcccgggcat cgcttgtacc agcgatgccc tgca                                34

<210> SEQ ID NO 71
<211> LENGTH: 22
<212> TYPE: DNA
<213> ORGANISM: artificial
<220> FEATURE:
<223> OTHER INFORMATION: synthetic molecule constructed according to the
      described algorithm

<400> SEQUENCE: 71
ggggagggat ttcaacaggc ag                                             22

<210> SEQ ID NO 72
<211> LENGTH: 39
<212> TYPE: DNA
<213> ORGANISM: artificial
<220> FEATURE:
<223> OTHER INFORMATION: synthetic molecule constructed according to the
      described algorithm

<400> SEQUENCE: 72
caaccggcag acgatgatcg aattaagggc ctgaatgtt                           39
```

```
<210> SEQ ID NO 73
<211> LENGTH: 53
<212> TYPE: DNA
<213> ORGANISM: artificial
<220> FEATURE:
<223> OTHER INFORMATION: synthetic molecule constructed according to the
      described algorithm

<400> SEQUENCE: 73
gcgaaaaagg ccggcgaggg tgcaaaagtt attgaactgc agggcatcgc tgg            53

<210> SEQ ID NO 74
<211> LENGTH: 31
<212> TYPE: DNA
<213> ORGANISM: artificial
<220> FEATURE:
<223> OTHER INFORMATION: synthetic molecule constructed according to the
      described algorithm

<400> SEQUENCE: 74
aattcgatca tcgtctgccg gttgagaggc t                                    31

<210> SEQ ID NO 75
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 75
atccctcccc ccattcccgg gcatcgcttg ta                                   32

<210> SEQ ID NO 76
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 76
tggcctgatc atccagcgtg ataacgggaa tg                                   32

<210> SEQ ID NO 77
<211> LENGTH: 19
<212> TYPE: DNA
<213> ORGANISM: artificial
<220> FEATURE:
<223> OTHER INFORMATION: synthetic molecule constructed according to the
      described algorithm

<400> SEQUENCE: 77
cgcttgtacc agcgatgcc                                                  19

<210> SEQ ID NO 78
<211> LENGTH: 30
<212> TYPE: DNA
<213> ORGANISM: artificial
<220> FEATURE:
<223> OTHER INFORMATION: synthetic molecule constructed according to the
      described algorithm

<400> SEQUENCE: 78
ccatttcatc ttcttgggcg aacacagcct                                      30

<210> SEQ ID NO 79
```

```
<211> LENGTH: 39
<212> TYPE: DNA
<213> ORGANISM: artificial
<220> FEATURE:
<223> OTHER INFORMATION: synthetic molecule constructed according to the
      described algorithm

<400> SEQUENCE: 79
ctgtgttcgc ccaagaagat gaaatggcac tgggtgcgc                            39

<210> SEQ ID NO 80
<211> LENGTH: 22
<212> TYPE: DNA
<213> ORGANISM: artificial
<220> FEATURE:
<223> OTHER INFORMATION: synthetic molecule constructed according to the
      described algorithm

<400> SEQUENCE: 80
ttcttgggcg aacacagcct gt                                              22

<210> SEQ ID NO 81
<211> LENGTH: 33
<212> TYPE: DNA
<213> ORGANISM: artificial
<220> FEATURE:
<223> OTHER INFORMATION: synthetic molecule constructed according to the
      described algorithm

<400> SEQUENCE: 81
tcacgctgga tgatcaggcc actaagggcg aag                                  33

<210> SEQ ID NO 82
<211> LENGTH: 39
<212> TYPE: DNA
<213> ORGANISM: artificial
<220> FEATURE:
<223> OTHER INFORMATION: synthetic molecule constructed according to the
      described algorithm

<400> SEQUENCE: 82
tcaaagagac ttcaaacggt tcatttaacg tttcaacca                            39

<210> SEQ ID NO 83
<211> LENGTH: 44
<212> TYPE: DNA
<213> ORGANISM: artificial
<220> FEATURE:
<223> OTHER INFORMATION: synthetic molecule constructed according to the
      described algorithm

<400> SEQUENCE: 83
gaaacgttaa atgaaccgtt tgaagtctct ttgaaggacg gcgc                      44

<210> SEQ ID NO 84
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 84
aaagatacca ttgcgctggt ggttgaaacg ttaaatgaac cgtttgaa                  48

<210> SEQ ID NO 85
<211> LENGTH: 40
```

<212> TYPE: DNA
<213> ORGANISM: artificial
<220> FEATURE:
<223> OTHER INFORMATION: synthetic molecule constructed according to the
      described algorithm

<400> SEQUENCE: 85
tcaaagagac ttcaaacggg ttatttaacg tttcaaccac                              40

<210> SEQ ID NO 86
<211> LENGTH: 45
<212> TYPE: DNA
<213> ORGANISM: artificial
<220> FEATURE:
<223> OTHER INFORMATION: synthetic molecule constructed according to the
      described algorithm

<400> SEQUENCE: 86
tgaaacgtta ataacccgt ttgaagtctc tttgaaggac ggcgc                         45

<210> SEQ ID NO 87
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 87
aaagatacca ttgcgctggt ggttgaaacg ttaaataacc cgtttgaa                     48

<210> SEQ ID NO 88
<211> LENGTH: 25
<212> TYPE: DNA
<213> ORGANISM: artificial
<220> FEATURE:
<223> OTHER INFORMATION: synthetic molecule constructed according to the
      described algorithm

<400> SEQUENCE: 88
cctcccccca ttcccgggcc gcgct                                              25

<210> SEQ ID NO 89
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 89
ggcccgggaa tgggggagg gatttcaaca gg                                       32

<210> SEQ ID NO 90
<211> LENGTH: 15
<212> TYPE: DNA
<213> ORGANISM: artificial
<220> FEATURE:
<223> OTHER INFORMATION: synthetic molecule constructed according to the
      described algorithm

<400> SEQUENCE: 90
ttcccgggcc gcgct                                                         15

<210> SEQ ID NO 91
<211> LENGTH: 22
<212> TYPE: DNA

```
<213> ORGANISM: artificial
<220> FEATURE:
<223> OTHER INFORMATION: synthetic molecule constructed according to the
      described algorithm

<400> SEQUENCE: 91 tgggggagg gatttcaaca gg                                              22

<210> SEQ ID NO 92
<211> LENGTH: 25
<212> TYPE: DNA
<213> ORGANISM: artificial
<220> FEATURE:
<223> OTHER INFORMATION: synthetic molecule constructed according to the
      described algorithm

<400> SEQUENCE: 92 tgggggagg gatttcaaca ggcag                                           25

<210> SEQ ID NO 93
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 93
tcaaagagac ttcaaacggg ttatttaacg tgctaacc                            38

<210> SEQ ID NO 94
<211> LENGTH: 43
<212> TYPE: DNA
<213> ORGANISM: artificial
<220> FEATURE:
<223> OTHER INFORMATION: synthetic molecule constructed according to the
      described algorithm

<400> SEQUENCE: 94
gcacgttaaa taacccgttt gaagtctctt tgaaggacgg cgc                      43

<210> SEQ ID NO 95
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 95
aaagatacca ttgcgctggt ggttagcacg ttaaataacc cgtttgaa                 48

<210> SEQ ID NO 96
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 96
ccatttcatc ttcttgggcg aacacagcct gt                                  32

<210> SEQ ID NO 97
<211> LENGTH: 813
<212> TYPE: DNA
<213> ORGANISM: artificial
```

```
<220> FEATURE:
<223> OTHER INFORMATION: synthetic molecule constructed according to the
      described algorithm

<400> SEQUENCE: 97
aaagatacca ttgcgctggt ggttagcacg ttaaataacc cgttttttcgt ctctttgaag    60 gacggcgccc agaaagaagc agataaactt ggttataatc tcgtagtgct ggacagtcaa   120
aacaatccag ctaaggagct ggcgaacgtt caggatttaa ctgtccgtgg gacaaaaatc   180
ttgcttataa atcctaccga ctcagatgcc gtaggaaacg cagtgaaaat ggctaatcaa   240
gcgaacattc ccgttatcac gctggatcgc caggccacta agggcgaagt cgtgtcccat   300
attgcatcgg acaatgtact cggtgggaaa atcgctggag attacatagc gaaaaaggcc   360
ggcgagggtg caaaagttat tgaactgcag ggcatcgctg gtacaagcgc ggcccgggaa   420
agaggggagg gatttcaaca ggcagtggcg gctcacaaat tcaacgtctt agcctctcaa   480
ccggcagact ttgatcgaat taagggcctg aatgttatgc agaacttgct taccgcgcat   540
ccagacgtac aggctgtgtt cgcccaaaat gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cacaattgcc ggatcagatc   720
ggtgcgaaag gggtcgaaac agctgataaa gttcttaagg gcgaaaaagt gcaggccaaa   780 tatccccgtag acctgaagtt agttgtgaaa caa                               813

<210> SEQ ID NO 98
<211> LENGTH: 813
<212> TYPE: DNA
<213> ORGANISM: artificial
<220> FEATURE:
<223> OTHER INFORMATION: synthetic molecule constructed according to the
      described algorithm

<400> SEQUENCE: 98
aaagatacca ttgcgctggt ggttgaaacg ttaaatgaac cgtgggaagt ctctttgaag    60
gacggcgccc agaaagaagc agataaactt ggttataatc tcgtagtgct ggacagtcaa   120
aacaatccag ctaaggagct ggcgaacgtt caggatttaa ctgtccgtgg gacaaaaatc   180
ttgcttatag atcctaccga ctcagatgcc gtaggaaacg cagtgaaaat ggctaatcaa   240
gcgaacattc ccgttatcac gctggatgat caggccacta agggcgaagt cgtgtcccat   300
attgcagaag acaatgtact cggtgggaaa atcgctggag attacatagc gaaaaaggcc   360
ggcgagggtg caaaagttat tgaactgcag ggcatcgctg gtacaagcga tgcccgggaa   420 tgggggagg gatttcaaca ggcagtggcg gctcacaaat tcaacgtctt agcctctcaa    480
ccggcagacg atgatcgaat taagggcctg aatgttatgc agaacttgct taccgcgcat   540
ccagacgtac aggctgtgtt cgcccaagaa gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cagaattgcc ggatcagatc   720
ggtgcgaaag gggtcgaaac agctgataaa gttcttaagg gcgaaaaagt gcaggccaaa   780 tatccccgtag acctgaagtt agttgtgaaa caa                               813

<210> SEQ ID NO 99
<211> LENGTH: 813
<212> TYPE: DNA
<213> ORGANISM: artificial
<220> FEATURE:
```

<223> OTHER INFORMATION: synthetic molecule constructed according to the
      described algorithm

<400> SEQUENCE: 99

```
aaagatacca ttgcgctggt ggttgaaacg ttaaatgaac cgtgggaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg acaaaaatc      180
ttgcttatag atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcga tgcccgggaa     420
tgggggagg  gatttcaaca ggcagtggcg gctcacaaat tcaacgtctt agcctctcaa     480
ccggcagacg atgatcgaat taagggcctg aatgttatgc agaacttgct taccgcgcat     540
ccagacgtac aggctgtgtt cgcccaagaa gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cagaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 100
<211> LENGTH: 813
<212> TYPE: DNA
<213> ORGANISM: artificial
<220> FEATURE:
<223> OTHER INFORMATION: synthetic molecule constructed according to the
      described algorithm

<400> SEQUENCE: 100

```
aaagatacca ttgcgctggt ggttgaaacg ttaaatgaac cgtgggaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg acaaaaatc      180
ttgcttataa atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcga tgcccgggaa     420
tgggggagg  gatttcaaca ggcagtggcg gctcacaaat tcaacgtctt agcctctcaa     480
ccggcagacg atgatcgaat taagggcctg aatgttatgc agaacttgct taccgcgcat     540
ccagacgtac aggctgtgtt cgcccaagaa gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cagaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 101
<211> LENGTH: 813
<212> TYPE: DNA
<213> ORGANISM: artificial
<220> FEATURE:
<223> OTHER INFORMATION: synthetic molecule constructed according to the -continued described algorithm

<400> SEQUENCE: 101

```
aaagatacca ttgcgctggt ggttgaaacg ttaaatgaac cgtgggaagt ctctttgaag    60
gacggcgccc agaaagaagc agataaactt ggttataatc tcgtagtgct ggacagtcaa   120
aacaatccag ctaaggagct ggcgaacgtt caggatttaa ctgtccgtgg gacaaaaatc   180
ttgcttataa atcctaccga ctcagatgcc gtaggaaacg cagtgaaaat ggctaatcaa   240
gcgaacattc ccgttatcac gctggatgat caggccacta agggcgaagt cgtgtcccat   300
attgcatcgg acaatgtact cggtgggaaa atcgctggag attacatagc gaaaaaggcc   360
ggcgagggtg caaaagttat tgaactgcag ggcatcgctg gtacaagcga tgcccgggaa   420
tgggggagg gatttcaaca ggcagtggcg gctcacaaat tcaacgtctt agcctctcaa   480
ccggcagacg atgatcgaat taagggcctg aatgttatgc agaacttgct taccgcgcat   540
ccagacgtac aggctgtgtt cgcccaagaa gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cacaattgcc ggatcagatc   720
ggtgcgaaag gggtcgaaac agctgataaa gttcttaagg gcgaaaaagt gcaggccaaa   780
tatcccgtag acctgaagtt agttgtgaaa caa                                 813
```

<210> SEQ ID NO 102
<211> LENGTH: 813
<212> TYPE: DNA
<213> ORGANISM: artificial
<220> FEATURE:
<223> OTHER INFORMATION: synthetic molecule constructed according to the described algorithm

<400> SEQUENCE: 102

```
aaagatacca ttgcgctggt ggttgaaacg ttaaatgaac cgtttgaagt ctctttgaag    60
gacggcgccc agaaagaagc agataaactt ggttataatc tcgtagtgct ggacagtcaa   120
aacaatccag ctaaggagct ggcgaacgtt caggatttaa ctgtccgtgg gacaaaaatc   180
ttgcttataa atcctaccga ctcagatgcc gtaggaaacg cagtgaaaat ggctaatcaa   240
gcgaacattc ccgttatcac gctggatgat caggccacta agggcgaagt cgtgtcccat   300
attgcatcgg acaatgtact cggtgggaaa atcgctggag attacatagc gaaaaaggcc   360
ggcgagggtg caaaagttat tgaactgcag ggcatcgctg gtacaagcga tgcccgggaa   420
tgggggagg gatttcaaca ggcagtggcg gctcacaaat tcaacgtctt agcctctcaa   480
ccggcagacg atgatcgaat taagggcctg aatgttatgc agaacttgct taccgcgcat   540
ccagacgtac aggctgtgtt cgcccaagaa gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cacaattgcc ggatcagatc   720
ggtgcgaaag gggtcgaaac agctgataaa gttcttaagg gcgaaaaagt gcaggccaaa   780
tatcccgtag acctgaagtt agttgtgaaa caa                                 813
```

<210> SEQ ID NO 103
<211> LENGTH: 813
<212> TYPE: DNA
<213> ORGANISM: artificial
<220> FEATURE:
<223> OTHER INFORMATION: synthetic molecule constructed according to the described algorithm

<400> SEQUENCE: 103

```
aaagatacca ttgcgctggt ggttgaaacg ttaaataacc cgtttgaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg gacaaaaatc     180
ttgcttataa atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcga tgcccgggaa     420
tgggggagg gatttcaaca ggcagtggcg gctcacaaat tcaacgtctt agcctctcaa     480
ccggcagacg atgatcgaat taagggcctg aatgttatgc agaacttgct taccgcgcat     540
ccagacgtac aggctgtgtt cgcccaagaa gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cacaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 104
<211> LENGTH: 813
<212> TYPE: DNA
<213> ORGANISM: artificial
<220> FEATURE:
<223> OTHER INFORMATION: synthetic molecule constructed according to the
      described algorithm

<400> SEQUENCE: 104

```
aaagatacca ttgcgctggt ggttgaaacg ttaaataacc cgtttgaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg gacaaaaatc     180
ttgcttataa atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcgc ggcccgggaa     420
tgggggagg gatttcaaca ggcagtggcg gctcacaaat tcaacgtctt agcctctcaa     480
ccggcagacg atgatcgaat taagggcctg aatgttatgc agaacttgct taccgcgcat     540
ccagacgtac aggctgtgtt cgcccaagaa gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cacaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 105
<211> LENGTH: 813
<212> TYPE: DNA
<213> ORGANISM: artificial
<220> FEATURE:
<223> OTHER INFORMATION: synthetic molecule constructed according to the
      described algorithm -continued

<400> SEQUENCE: 105

```
aaagatacca ttgcgctggt ggttagcacg ttaaataacc cgtttgaagt ctctttgaag    60
gacggcgccc agaaagaagc agataaactt ggttataatc tcgtagtgct ggacagtcaa   120
aacaatccag ctaaggagct ggcgaacgtt caggatttaa ctgtccgtgg acaaaaatc   180
ttgcttataa atcctaccga ctcagatgcc gtaggaaacg cagtgaaaat ggctaatcaa   240
gcgaacattc ccgttatcac gctggatgat caggccacta agggcgaagt cgtgtcccat   300
attgcatcgg acaatgtact cggtgggaaa atcgctggag attacatagc gaaaaaggcc   360
ggcgagggtg caaaagttat tgaactgcag ggcatcgctg gtacaagcgc ggcccgggaa   420
tgggggagg gatttcaaca ggcagtggcg gctcacaaat tcaacgtctt agcctctcaa   480
ccggcagacg atgatcgaat taagggcctg aatgttatgc agaacttgct taccgcgcat   540
ccagacgtac aggctgtgtt cgcccaagaa gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cacaattgcc ggatcagatc   720
ggtgcgaaag gggtcgaaac agctgataaa gttcttaagg gcgaaaaagt gcaggccaaa   780
tatcccgtag acctgaagtt agttgtgaaa caa                                813
```

<210> SEQ ID NO 106
<211> LENGTH: 813
<212> TYPE: DNA
<213> ORGANISM: artificial
<220> FEATURE:
<223> OTHER INFORMATION: synthetic molecule constructed according to the
      described algorithm

<400> SEQUENCE: 106

```
aaagatacca ttgcgctggt ggttagcacg ttaaataacc cgtttgaagt ctctttgaag    60
gacggcgccc agaaagaagc agataaactt ggttataatc tcgtagtgct ggacagtcaa   120
aacaatccag ctaaggagct ggcgaacgtt caggatttaa ctgtccgtgg acaaaaatc   180
ttgcttataa atcctaccga ctcagatgcc gtaggaaacg cagtgaaaat ggctaatcaa   240
gcgaacattc ccgttatcac gctggatgat caggccacta agggcgaagt cgtgtcccat   300
attgcatcgg acaatgtact cggtgggaaa atcgctggag attacatagc gaaaaaggcc   360
ggcgagggtg caaaagttat tgaactgcag ggcatcgctg gtacaagcgc ggcccgggaa   420
agaggggagg gatttcaaca ggcagtggcg gctcacaaat tcaacgtctt agcctctcaa   480
ccggcagacg atgatcgaat taagggcctg aatgttatgc agaacttgct taccgcgcat   540
ccagacgtac aggctgtgtt cgcccaagaa gatgaaatgg cactgggtgc gctccgtgct   600
ttacagacgg ccggcaaaag tgatgtcatg gttgtgggtt ttgacgggac ccctgatgga   660
gagaaagcag taaacgacgg caagctggcg gccactatag cacaattgcc ggatcagatc   720
ggtgcgaaag gggtcgaaac agctgataaa gttcttaagg gcgaaaaagt gcaggccaaa   780
tatcccgtag acctgaagtt agttgtgaaa caa                                813
```

<210> SEQ ID NO 107
<211> LENGTH: 813
<212> TYPE: DNA
<213> ORGANISM: artificial
<220> FEATURE:
<223> OTHER INFORMATION: synthetic molecule constructed according to the
      described algorithm

<400> SEQUENCE: 107

-continued

```
aaagatacca ttgcgctggt ggttagcacg ttaaataacc cgtttgaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg acaaaaatc     180
ttgcttataa atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcgc ggcccgggaa     420
agagggagg gatttcaaca ggcagtggcg gctcacaaat tcaacgtctt agcctctcaa     480
ccggcagacg atgatcgaat taagggcctg aatgttatgc agaacttgct taccgcgcat     540
ccagacgtac aggctgtgtt cgcccaaaat gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cacaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 108
<211> LENGTH: 813
<212> TYPE: DNA
<213> ORGANISM: artificial
<220> FEATURE:
<223> OTHER INFORMATION: synthetic molecule constructed according to the described algorithm

<400> SEQUENCE: 108

```
aaagatacca ttgcgctggt ggttagcacg ttaaataacc cgtttgaagt ctctttgaag      60
gacggcgccc agaaagaagc agataaactt ggttataatc tcgtagtgct ggacagtcaa     120
aacaatccag ctaaggagct ggcgaacgtt caggatttaa ctgtccgtgg acaaaaatc     180
ttgcttataa atcctaccga ctcagatgcc gtaggaaacg cagtgaaaat ggctaatcaa     240
gcgaacattc ccgttatcac gctggatgat caggccacta agggcgaagt cgtgtcccat     300
attgcatcgg acaatgtact cggtgggaaa atcgctggag attacatagc gaaaaaggcc     360
ggcgagggtg caaaagttat tgaactgcag ggcatcgctg gtacaagcgc ggcccgggaa     420
agagggagg gatttcaaca ggcagtggcg gctcacaaat tcaacgtctt agcctctcaa     480
ccggcagact tgatcgaat taagggcctg aatgttatgc agaacttgct taccgcgcat     540
ccagacgtac aggctgtgtt cgcccaaaat gatgaaatgg cactgggtgc gctccgtgct     600
ttacagacgg ccggcaaaag tgatgtcatg gttgtgggtt ttgacgggac ccctgatgga     660
gagaaagcag taaacgacgg caagctggcg gccactatag cacaattgcc ggatcagatc     720
ggtgcgaaag gggtcgaaac agctgataaa gttcttaagg gcgaaaaagt gcaggccaaa     780
tatcccgtag acctgaagtt agttgtgaaa caa                                  813
```

<210> SEQ ID NO 109
<211> LENGTH: 29
<212> TYPE: DNA
<213> ORGANISM: artificial
<220> FEATURE:
<223> OTHER INFORMATION: synthetic molecule constructed according to the described algorithm

<400> SEQUENCE: 109

```
ccgaattcgc gacagcagcg cagggaccc                                          29

<210> SEQ ID NO 110
<211> LENGTH: 35
<212> TYPE: DNA
<213> ORGANISM: artificial
<220> FEATURE:
<223> OTHER INFORMATION: synthetic molecule constructed according to the
      described algorithm

<400> SEQUENCE: 110
tggtggccac gtgatgcaca aacatgatca ggaag                                   35

<210> SEQ ID NO 111
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 111
tgtttgtgca tcacgtggcc accatcattc tc                                      32

<210> SEQ ID NO 112
<211> LENGTH: 30
<212> TYPE: DNA
<213> ORGANISM: artificial
<220> FEATURE:
<223> OTHER INFORMATION: synthetic molecule constructed according to the
      described algorithm

<400> SEQUENCE: 112
ccctcgagtc agtcattctt acgatggttg                                         30

<210> SEQ ID NO 113
<211> LENGTH: 35
<212> TYPE: DNA
<213> ORGANISM: artificial
<220> FEATURE:
<223> OTHER INFORMATION: synthetic molecule constructed according to the
      described algorithm

<400> SEQUENCE: 113
gttccttgaa gtcctttctt ttaatgtctg taaac                                   35

<210> SEQ ID NO 114
<211> LENGTH: 48
<212> TYPE: DNA
<213> ORGANISM: artificial
<220> FEATURE:
<223> OTHER INFORMATION: synthetic molecule constructed according to the
      described algorithm

<400> SEQUENCE: 114
cagtttacag acattaaaag aaaggacttc aaggaacaga tcatccac                     48

<210> SEQ ID NO 115
<211> LENGTH: 34
<212> TYPE: DNA
<213> ORGANISM: artificial
<220> FEATURE:
<223> OTHER INFORMATION: synthetic molecule constructed according to the
      described algorithm

<400> SEQUENCE: 115
aagttcaatc atataatagt gataaagccc actt                                    34
```

<210> SEQ ID NO 116
<211> LENGTH: 52
<212> TYPE: DNA
<213> ORGANISM: artificial
<220> FEATURE:
<223> OTHER INFORMATION: synthetic molecule constructed according to the
      described algorithm

<400> SEQUENCE: 116
ttcaagtggg ctttatcact attatatgat tgaactttcc ttctactggt cc           52

<210> SEQ ID NO 117
<211> LENGTH: 31
<212> TYPE: DNA
<213> ORGANISM: artificial
<220> FEATURE:
<223> OTHER INFORMATION: synthetic molecule constructed according to the
      described algorithm

<400> SEQUENCE: 117
gcaatcagat aaaatgtgaa tctccacatg c                                  31

<210> SEQ ID NO 118
<211> LENGTH: 46
<212> TYPE: DNA
<213> ORGANISM: artificial
<220> FEATURE:
<223> OTHER INFORMATION: synthetic molecule constructed according to the
      described algorithm

<400> SEQUENCE: 118
gcatgtggag attcacattt tatctgattg ccttcattgc cggcat                  46

<210> SEQ ID NO 119
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 119
ccctcgagtt actcttcagc ccagtagctg cctcccat                           38

<210> SEQ ID NO 120
<211> LENGTH: 37
<212> TYPE: DNA
<213> ORGANISM: artificial
<220> FEATURE:
<223> OTHER INFORMATION: synthetic molecule constructed according to the
      described algorithm

<400> SEQUENCE: 120
atatacataa gtaaaatgtg aatctccagc tggcttc                            37

<210> SEQ ID NO 121
<211> LENGTH: 52
<212> TYPE: DNA
<213> ORGANISM: artificial
<220> FEATURE:
<223> OTHER INFORMATION: synthetic molecule constructed according to the
      described algorithm

<400> SEQUENCE: 121
agccagctgg agattcacat tttacttatg tatattctgc tatggaatta ga           52

<210> SEQ ID NO 122
<211> LENGTH: 30
<212> TYPE: DNA
<213> ORGANISM: artificial
<220> FEATURE:
<223> OTHER INFORMATION: synthetic molecule constructed according to the
described algorithm

<400> SEQUENCE: 122
ccgaattcct ccagaccttg tatgattact                              30

<210> SEQ ID NO 123
<211> LENGTH: 24
<212> TYPE: DNA
<213> ORGANISM: artificial
<220> FEATURE:
<223> OTHER INFORMATION: synthetic molecule constructed according to the
described algorithm

<400> SEQUENCE: 123
cggtcctggt tcctccgatg gcga                                    24

<210> SEQ ID NO 124
<211> LENGTH: 32
<212> TYPE: DNA
<213> ORGANISM: artificial
<220> FEATURE:
<223> OTHER INFORMATION: synthetic molecule constructed according to the
described algorithm

<400> SEQUENCE: 124
cgccatcgga ggaaccagga ccggcccagt ct                           32

<210> SEQ ID NO 125
<211> LENGTH: 22
<212> TYPE: DNA
<213> ORGANISM: artificial
<220> FEATURE:
<223> OTHER INFORMATION: synthetic molecule constructed according to the
described algorithm

<400> SEQUENCE: 125
ccgaattcct ccagaccttg ta                                      22

<210> SEQ ID NO 126
<211> LENGTH: 53
<212> TYPE: DNA
<213> ORGANISM: artificial
<220> FEATURE:
<223> OTHER INFORMATION: synthetic molecule constructed according to the
described algorithm

<400> SEQUENCE: 126
gatacttctt tgagcgatac gtggctacac cactggctgc cctcttgaac ata     53

<210> SEQ ID NO 127
<211> LENGTH: 33
<212> TYPE: DNA
<213> ORGANISM: artificial
<220> FEATURE:
<223> OTHER INFORMATION: synthetic molecule constructed according to the
described algorithm

<400> SEQUENCE: 127
ccctcgagtc agtcattctt acgatggttg tta                          33

```
<210> SEQ ID NO 128
<211> LENGTH: 32
<212> TYPE: DNA
<213> ORGANISM: artificial
<220> FEATURE:
<223> OTHER INFORMATION: synthetic molecule constructed according to the
      described algorithm

<400> SEQUENCE: 128
agccacgtat cgctcaaaga agtatcgaac ga                                32

<210> SEQ ID NO 129
<211> LENGTH: 26
<212> TYPE: DNA
<213> ORGANISM: artificial
<220> FEATURE:
<223> OTHER INFORMATION: synthetic molecule constructed according to the
      described algorithm

<400> SEQUENCE: 129
ccacaatgac tctcatgccg gcaatg                                       26

<210> SEQ ID NO 130
<211> LENGTH: 38
<212> TYPE: DNA
<213> ORGANISM: artificial
<220> FEATURE:
<223> OTHER INFORMATION: synthetic molecule constructed according to the
      described algorithm

<400> SEQUENCE: 130
ttgccggcat gagagtcatt gtggataaac cctggttc                          38

<210> SEQ ID NO 131
<211> LENGTH: 43
<212> TYPE: DNA
<213> ORGANISM: artificial
<220> FEATURE:
<223> OTHER INFORMATION: synthetic molecule constructed according to the
      described algorithm

<400> SEQUENCE: 131
gatacttctt tgagcgatac gtggctacac cactggctgc cct                    43

<210> SEQ ID NO 132
<211> LENGTH: 19
<212> TYPE: DNA
<213> ORGANISM: artificial
<220> FEATURE:
<223> OTHER INFORMATION: synthetic molecule constructed according to the
      described algorithm

<400> SEQUENCE: 132
tctcatgccg gcaatgaag                                               19

<210> SEQ ID NO 133
<211> LENGTH: 33
<212> TYPE: DNA
<213> ORGANISM: artificial
<220> FEATURE:
<223> OTHER INFORMATION: synthetic molecule constructed according to the
      described algorithm

<400> SEQUENCE: 133
tagccacgta tcgctcaaag aagtatcgaa cga                               33

<210> SEQ ID NO 134
```

```
<211> LENGTH: 1176
<212> TYPE: DNA
<213> ORGANISM: artificial
<220> FEATURE:
<223> OTHER INFORMATION: synthetic molecule constructed according to the
      described algorithm

<400> SEQUENCE: 134
gcgacagcag cgcagggacc cctaagcttg ctgtggggct ggctgtggag cgagcgcttc      60
tggctacccg agaacgtgag ctgggctgat ctggaggggc cggccgacgg ctacggttac     120
ccccgcggcc ggcacatcct ctcggtgttc ccgctggcgg cgggcatctt cttcgtgagg     180
ctgctcttcg agcgatttat tgccaaaccc tgtgcactct gtattggcat cgaggacagt     240
ggtccttatc aggcccaacc caatgccatc cttgaaaagg tgttcatatc tattaccaag     300
tatcctgata agaaaaggct ggagggcctg tcaaagcagc tggattggaa tgtccgaaaa     360
atccaatgct ggtttcgcca tcggaggaat caggacaagc ccccaacgct tactaaattc     420
tgtgaaagca tgtggagatt cacattttat ttatgtatat tctgctatgg aattagattt     480
ctctggtcgt caccttggtt ctgggacatc cgacagtgct ggcataacta tccatttcag     540 cctcttttcaa gtgggcttta tcactattat atcatggaat tggccttcta ttggtccctt    600
atgttttctc agtttacaga cattaaaaga aaggacttcc tgatcatgtt tgtgcatcac     660
ttggtcacca ttgggcttat ctccttctcc tacatcaaca atatggttcg agtgggaact     720
ctgatcatgt gtctacatga tgtctcagac ttcttgctgg aggcagccaa actggccaat     780
tatgccaagt atcagcggct ctgtgacacc cttttttgtga tcttcagtgc tgtttttatg     840
gttacacgac taggaatcta tccattctgg attctgaaca cgaccctctt tgagagttgg     900
gagataatcg ggccttatgc ttcatggtgg ctcctcaatg gctgctgct gaccctacag     960 cttctgcatg tcatctggtc ctacctaatt gcacggattg ctttgaaagc cttgatcagg    1020
ggaaaggtat cgaaggatga tcgcagtgat gtggagagca gctcagagga agaagatgtg    1080
accacctgca caaaaagtcc ctgtgacagt agctccagca atggtgccaa tcgggtgaat    1140
ggtcacatgg gaggcagcta ctgggctgaa gagtaa                              1176

<210> SEQ ID NO 135
<211> LENGTH: 1140
<212> TYPE: DNA
<213> ORGANISM: artificial
<220> FEATURE:
<223> OTHER INFORMATION: synthetic molecule constructed according to the
      described algorithm

<400> SEQUENCE: 135
ctccagacct tgtatgatta cttctggtgg gaacgtctgt ggctgcctgt gaacttgacc      60
tgggccgatc tagaagaccg agatggacgt gtctacgcca aagcctcaga tctctatatc     120
acgctgcccc tggccttgct cttcctcatc gttcgatact tctttgagct gtacgtggct     180
acaccactgg ctgccctctt gaacataaag gagaaaactc ggctgcgggc acctcccaac     240
gccaccttgg aacatttcta cctgaccagt ggcaagcagc ccaagcaggt ggaagtagag     300
cttttgtccc ggcagagcgg gctctctggc cgccaggtag agcgttggtt ccgtcgccgc     360
cgcaaccagg accggcccag tctcctcaag aagttccgag aagccagctg gagattcaca     420
ttttacctga ttgccttcat tgccggcatg gccgtcattg tggataaacc ctggttctat     480
gacatgaaga agtttgggga gggatatccc atacagagca ctatcccttc ccagtattgg     540
tactacatga ttgaactttc cttctactgg tccctgctct tcagcattgc ctctgatgtc     600
```

```
aagcgaaagg atttcaagga acagatcatc caccatgtgg ccaccatcat tctcatcagc    660
ttttcctggt tgccaatta catccgagct gggactctaa tcatggctct gcatgactct    720
tccgattacc tgctggagtc agccaagatg tttaactacg cgggatggaa gaacacctgc    780
aacaacatct tcatcgtctt cgccattgtt tttatcatca cccgactggt catcctgccc    840
ttctggatcc tgcattgcac cctggtgtac ccactggagc tctatcctgc cttctttggc    900
tattacttct tcaattccat gatgggagtt ctacagctgc tgcatatctt ctgggcctac    960
ctcattttgc gcatggccca aagttcata actggaaagc tggtagaaga tgaacgcagt   1020
gaccgggaag aaacagagag ctcagagggg aggaggctg cagctggggg aggagcaaag    1080
agccggcccc tagccaatgg ccaccccatc ctcaataaca accatcgtaa gaatgactga   1140
```

<210> SEQ ID NO 136
<211> LENGTH: 1180
<212> TYPE: DNA
<213> ORGANISM: artificial
<220> FEATURE:
<223> OTHER INFORMATION: synthetic molecule constructed according to the
      described algorithm

<400> SEQUENCE: 136

```
ccgaattcgc gacagcagcg cagggacccc taagcttgct gtggggctgg ctgtggagcg     60
agcgcttctg gctacccgag aacgtgagct gggctgatct ggaggggccg ccgacggct    120 acggttaccc ccgcggccgg cacatcctct cggtgttccc gctggcggcg ggcatcttct    180
tcgtgaggct gctcttcgag cgatttattg ccaaaccctg tgcactctgt attggcatcg    240
aggacagtgg tccttatcag gcccaaccca atgccatcct tgaaaaggtg ttcatatcta    300
ttaccaagta tcctgataag aaaaggctgg agggcctgtc aaagcagctg gattggaatg    360
tccgaaaaat ccaatgctgg tttcgccatc ggaggaatca ggacaagccc caacgctta    420 ctaaattctg tgaaagcatg tggagattca cattttattt atgtatattc tgctatggaa    480
ttagatttct ctggtcgtca ccttggttct gggacatccg acagtgctgg cataactatc    540
catttcagcc tctttcaagt gggctttatc actattatat catggaattg gccttctatt    600
ggtcccttat gttttctcag tttacagaca ttaaaagaaa ggacttcctg atcatgtttg    660
tgcatcacgt ggccaccatc attctcatca gcttttcctg gtttgccaat tacatccgag    720
ctgggactct aatcatggct ctgcatgact cttccgatta cctgctggag tcagccaaga    780
tgtttaacta cgcgggatgg aagaacacct gcaacaacat cttcatcgtc ttcgccattg    840
tttttatcat cacccgactg gtcatcctgc ccttctggat cctgcattgc acccctggtgt    900 acccactgga gctctatcct gccttctttg gctattactt cttcaattcc atgatgggag    960
ttctacagct gctgcatatc ttctgggcct acctcatttt gcgcatggcc cacaagttca   1020
taactggaaa gctggtagaa gatgaacgca gtgaccggga agaaacagag agctcagagg   1080
gggaggaggc tgcagctggg ggaggagcaa agagccggcc cctagccaat ggccacccca   1140
tcctcaataa caaccatcgt aagaatgact gactcgaggg                         1180
```

<210> SEQ ID NO 137
<211> LENGTH: 1180
<212> TYPE: DNA
<213> ORGANISM: artificial
<220> FEATURE:
<223> OTHER INFORMATION: synthetic molecule constructed according to the
      described algorithm

<400> SEQUENCE: 137

```
ccgaattcgc gacagcagcg cagggacccc taagcttgct gtggggctgg ctgtggagcg      60
agcgcttctg gctacccgag aacgtgagct gggctgatct ggaggggccg gccgacggct     120
acggttaccc ccgcggccgg cacatcctct cggtgttccc gctggcggcg ggcatcttct     180
tcgtgaggct gctcttcgag cgatttattg ccaaaccctg tgcactctgt attggcatcg     240
aggacagtgg tccttatcag gcccaaccca atgccatcct tgaaaaggtg ttcatatcta     300
ttaccaagta tcctgataag aaaaggctgg agggcctgtc aaagcagctg gattggaatg     360
tccgaaaaat ccaatgctgg tttcgccatc ggaggaatca ggacaagccc caacgctta      420
ctaaattctg tgaaagcatg tggagattca cattttattt atgtatattc tgctatggaa     480
ttagatttct ctggtcgtca ccttggttct gggacatccg acagtgctgg cataactatc     540
catttcagcc tctttcaagt gggctttatc actattatat catggaattg gccttctatt     600
ggtcccttat gttttctcag tttacagaca ttaaaagaaa ggacttcaag gaacagatca     660
tccaccatgt ggccaccatc attctcatca gcttttcctg gttgccaat tacatccgag      720
ctgggactct aatcatggct ctgcatgact cttccgatta cctgctggag tcagccaaga     780
tgtttaacta cgcgggatgg aagaacacct gcaacaacat cttcatcgtc ttcgccattg     840
tttttatcat cacccgactg gtcatcctgc ccttctggat cctgcattgc accctggtgt     900
acccactgga gctctatcct gccttctttg gctattactt cttcaattcc atgatgggag     960
ttctacagct gctgcatatc ttctgggcct acctcatttt gcgcatggcc cacaagttca    1020
taactggaaa gctggtagaa gatgaacgca gtgaccggga agaaacagag agctcagagg    1080
ggaggaggc tgcagctggg ggaggagcaa agagccggcc cctagccaat ggccacccca     1140
tcctcaataa caaccatcgt aagaatgact gactcgaggg                         1180
```

<210> SEQ ID NO 138
<211> LENGTH: 1180
<212> TYPE: DNA
<213> ORGANISM: artificial
<220> FEATURE:
<223> OTHER INFORMATION: synthetic molecule constructed according to the described algorithm

<400> SEQUENCE: 138

```
ccgaattcgc gacagcagcg cagggacccc taagcttgct gtggggctgg ctgtggagcg      60
agcgcttctg gctacccgag aacgtgagct gggctgatct ggaggggccg gccgacggct     120
acggttaccc ccgcggccgg cacatcctct cggtgttccc gctggcggcg ggcatcttct     180
tcgtgaggct gctcttcgag cgatttattg ccaaaccctg tgcactctgt attggcatcg     240
aggacagtgg tccttatcag gcccaaccca atgccatcct tgaaaaggtg ttcatatcta     300
ttaccaagta tcctgataag aaaaggctgg agggcctgtc aaagcagctg gattggaatg     360
tccgaaaaat ccaatgctgg tttcgccatc ggaggaatca ggacaagccc caacgctta      420
ctaaattctg tgaaagcatg tggagattca cattttattt atgtatattc tgctatggaa     480
ttagatttct ctggtcgtca ccttggttct gggacatccg acagtgctgg cataactatc     540
catttcagcc tctttcaagt gggctttatc actattatat gattgaactt ccttctact      600
ggtcctgct cttcagcatt gcctctgatg tcaagcgaaa ggatttcaag gaacagatca     660
tccaccatgt ggccaccatc attctcatca gcttttcctg gttgccaat tacatccgag      720
ctgggactct aatcatggct ctgcatgact cttccgatta cctgctggag tcagccaaga     780
```

| | |
|---|---|
| tgtttaacta cgcgggatgg aagaacacct gcaacaacat cttcatcgtc ttcgccattg | 840 |
| tttttatcat cacccgactg gtcatcctgc ccttctggat cctgcattgc accctggtgt | 900 |
| acccactgga gctctatcct gccttctttg gctattactt cttcaattcc atgatgggag | 960 |
| ttctacagct gctgcatatc ttctgggcct acctcatttt gcgcatggcc cacaagttca | 1020 |
| taactggaaa gctggtagaa gatgaacgca gtgaccggga agaaacagag agctcagagg | 1080 |
| gggaggaggc tgcagctggg ggaggagcaa agagccggcc cctagccaat ggccacccca | 1140 |
| tcctcaataa caaccatcgt aagaatgact gactcgaggg | 1180 |

<210> SEQ ID NO 139
<211> LENGTH: 1180
<212> TYPE: DNA
<213> ORGANISM: artificial
<220> FEATURE:
<223> OTHER INFORMATION: synthetic molecule constructed according to the
described algorithm

<400> SEQUENCE: 139

| | |
|---|---|
| ccgaattcgc gacagcagcg cagggacccc taagcttgct gtggggctgg ctgtggagcg | 60 |
| agcgcttctg gctacccgag aacgtgagct gggctgatct ggaggggccg gccgacggct | 120 |
| acggttaccc ccgcggccgg cacatcctct cggtgttccc gctggcggcg ggcatcttct | 180 |
| tcgtgaggct gctcttcgag cgatttattg ccaaaccctg tgcactctgt attggcatcg | 240 |
| aggacagtgg tccttatcag gcccaaccca atgccatcct tgaaaaggtg ttcatatcta | 300 |
| ttaccaagta tcctgataag aaaaggctgg agggcctgtc aaagcagctg gattggaatg | 360 |
| tccgaaaaat ccaatgctgg tttcgccatc ggaggaatca ggacaagccc caacgctta | 420 |
| ctaaattctg tgaaagcatg tggagattca cattttatct gattgccttc attgccggca | 480 |
| tggccgtcat tgtggataaa ccctggttct atgacatgaa gaaagtttgg gagggatatc | 540 |
| ccatacagag cactatccct tcccagtatt ggtactacat gattgaactt tccttctact | 600 |
| ggtccctgct cttcagcatt gcctctgatg tcaagcgaaa ggatttcaag gaacagatca | 660 |
| tccaccatgt ggccaccatc attctcatca gcttttcctg gtttgccaat tacatccgag | 720 |
| ctgggactct aatcatggct ctgcatgact cttccgatta cctgctggag tcagccaaga | 780 |
| tgtttaacta cgcgggatgg aagaacacct gcaacaacat cttcatcgtc ttcgccattg | 840 |
| tttttatcat cacccgactg gtcatcctgc ccttctggat cctgcattgc accctggtgt | 900 |
| acccactgga gctctatcct gccttctttg gctattactt cttcaattcc atgatgggag | 960 |
| ttctacagct gctgcatatc ttctgggcct acctcatttt gcgcatggcc cacaagttca | 1020 |
| taactggaaa gctggtagaa gatgaacgca gtgaccggga agaaacagag agctcagagg | 1080 |
| gggaggaggc tgcagctggg ggaggagcaa agagccggcc cctagccaat ggccacccca | 1140 |
| tcctcaataa caaccatcgt aagaatgact gactcgaggg | 1180 |

<210> SEQ ID NO 140
<211> LENGTH: 1168
<212> TYPE: DNA
<213> ORGANISM: artificial
<220> FEATURE:
<223> OTHER INFORMATION: synthetic molecule constructed according to the
described algorithm

<400> SEQUENCE: 140

| | |
|---|---|
| ccgaattcct ccagaccttg tatgattact tctggtggga acgtctgtgg ctgcctgtga | 60 |
| acttgacctg ggccgatcta gaagaccgag atggacgtgt ctacgccaaa gcctcagatc | 120 |

```
tctatatcac gctgcccctg gccttgctct tcctcatcgt tcgatacttc tttgagctgt    180
acgtggctac accactggct gccctcttga acataaagga gaaaactcgg ctgcgggcac    240
ctcccaacgc caccttggaa catttctacc tgaccagtgg caagcagccc aagcaggtgg    300
aagtagagct tttgtcccgg cagagcgggc tctctggccg ccaggtagag cgttggttcc    360
gtcgccgccg caaccaggac cggcccagtc tcctcaagaa gttccgagaa gccagctgga    420
gattcacatt ttacttatgt atattctgct atggaattag atttctctgg tcgtcacctt    480
ggttctggga catccgacag tgctggcata actatccatt tcagcctctt tcaagtgggc    540
tttatcacta ttatatcatg gaattggcct tctattggtc ccttatgttt tctcagttta    600
cagacattaa agaaaggac ttcctgatca tgtttgtgca tcacttggtc accattgggc    660
ttatctcctt ctcctacatc aacaatatgg ttcgagtggg aactctgatc atgtgtctac    720
atgatgtctc agacttcttg ctggaggcag ccaaactggc caattatgcc aagtatcagc    780
ggctctgtga caccttttt gtgatcttca gtgctgtttt tatggttaca cgactaggaa    840
tctatccatt ctggattctg aacacgaccc tctttgagag ttgggagata tcgggccttt    900
atgcttcatg gtggctcctc aatggcctgc tgctgaccct acagcttctg catgtcatct    960
ggtcctacct aattgcacgg attgctttga agccttgat caggggaaag gtatcgaagg   1020
atgatcgcag tgatgtggag agcagctcag aggaagaaga tgtgaccacc tgcacaaaaa   1080
gtccctgtga cagtagctcc agcaatggtg ccaatcgggt gaatggtcac atgggaggca   1140
gctactgggc tgaagagtaa ctcgaggg                                     1168

<210> SEQ ID NO 141
<211> LENGTH: 1180
<212> TYPE: DNA
<213> ORGANISM: artificial
<220> FEATURE:
<223> OTHER INFORMATION: synthetic molecule constructed according to the
      described algorithm

<400> SEQUENCE: 141
ccgaattcgc gacagcagcg cagggacccc taagcttgct gtggggctgg ctgtggagcg     60
agcgcttctg gctacccgag aacgtgagct gggctgatct ggaggggccg ccgacggct    120 acggttaccc ccgcggccgg cacatcctct cggtgttccc gctggcggcg ggcatcttct    180
tcgtgaggct gctcttcgag cgatttattg ccaaaccctg tgcactctgt attggcatcg    240
aggacagtgg tccttatcag gcccaaccca atgccatcct tgaaaaggtg ttcatatcta    300
ttaccaagta tcctgataag aaaaggctgg agggcctgtc aaagcagctg gattggaatg    360
tccgaaaaat ccaatgctgg tttcgccatc ggaggaacca ggaccggccc agtctcctca    420
agaagttccg agaagccagc tggagattca cattttacct gattgccttc attgccggca    480
tggccgtcat tgtggataaa ccctggttct atgacatgaa gaaagtttgg gagggatatc    540
ccatacagag cactatccct tcccagtatt ggtactacat gattgaactt tccttctact    600
ggtccctgct cttcagcatt gcctctgatg tcaagcgaaa ggatttcaag gaacagatca    660
tccaccatgt ggccaccatc attctcatca gcttttcctg gtttgccaat tacatccgag    720
ctgggactct aatcatggct ctgcatgact cttccgatta cctgctggag tcagccaaga    780
tgtttaacta cgcgggatgg aagaacacct gcaacaacat cttcatcgtc ttcgccattg    840
tttttatcat caccccgactg gtcatcctgc ccttctggat cctgcattgc acctggtgt    900 acccactgga gctctatcct gccttctttg gctattactt cttcaattcc atgatgggag    960
```

```
ttctacagct gctgcatatc ttctgggcct acctcatttt gcgcatggcc cacaagttca    1020
taactggaaa gctggtagaa gatgaacgca gtgaccggga agaaacagag agctcagagg    1080
gggaggaggc tgcagctggg ggaggagcaa agagccggcc cctagccaat ggccacccca    1140
tcctcaataa caaccatcgt aagaatgact gactcgaggg                          1180
```

<210> SEQ ID NO 142
<211> LENGTH: 1156
<212> TYPE: DNA
<213> ORGANISM: artificial
<220> FEATURE:
<223> OTHER INFORMATION: synthetic molecule constructed according to the
      described algorithm

<400> SEQUENCE: 142

```
ccgaattcct ccagaccttg tatgattact tctggtggga acgtctgtgg ctgcctgtga     60
acttgacctg ggccgatcta aagaccgag atggacgtgt ctacgccaaa gcctcagatc    120
tctatatcac gctgcccctg gccttgctct tcctcatcgt tcgatacttc tttgagcgat    180
acgtggctac accactggct gccctcttga acataaagga gaaaactcgg ctgcgggcac    240
ctcccaacgc caccttggaa catttctacc tgaccagtgg caagcagccc aagcaggtgg    300
aagtagagct tttgtcccgg cagagcgggc tctctggccg ccaggtagag cgttggttcc    360
gtcgccgccg caaccaggac cggcccagtc tcctcaagaa gttccgagaa gccagctgga    420
gattcacatt ttacctgatt gccttcattg ccggcatggc cgtcattgtg gataaaccct    480
ggttctatga catgaagaaa gtttgggagg gatatcccat acagagcact atcccttccc    540
agtattggta ctacatgatt gaactttcct tctactggtc cctgctcttc agcattgcct    600
ctgatgtcaa gcgaaaggat ttcaaggaac agatcatcca ccatgtggcc accatcattc    660
tcatcagctt ttcctggttt gccaattaca tccgagctgg gactctaatc atggctctgc    720
atgactcttc cgattacctg ctggagtcag ccaagatgtt taactacgcg ggatggaaga    780
acacctgcaa caacatcttc atcgtcttcg ccattgtttt tatcatcacc cgactggtca    840
tcctgccctt ctggatcctg cattgcaccc tggtgtaccc actggagctc tatcctgcct    900
tctttggcta ttacttcttc aattccatga tgggagttct acagctgctg catatcttct    960
gggcctacct catttttgcgc atggcccaca agttcataac tggaaagctg gtagaagatg   1020
aacgcagtga ccgggaagaa acagagagct cagaggggga ggaggctgca gctggggag    1080 gagcaaagag ccggccccta gccaatggcc accccatcct caataacaac catcgtaaga   1140
atgactgact cgaggg                                                    1156
```

<210> SEQ ID NO 143
<211> LENGTH: 1156
<212> TYPE: DNA
<213> ORGANISM: artificial
<220> FEATURE:
<223> OTHER INFORMATION: synthetic molecule constructed according to the
      described algorithm

<400> SEQUENCE: 143

```
ccgaattcct ccagaccttg tatgattact tctggtggga acgtctgtgg ctgcctgtga     60
acttgacctg ggccgatcta aagaccgag atggacgtgt ctacgccaaa gcctcagatc    120
tctatatcac gctgcccctg gccttgctct tcctcatcgt tcgatacttc tttgagcgat    180
acgtggctac accactggct gccctcttga acataaagga gaaaactcgg ctgcgggcac    240
```

-continued

```
ctcccaacgc caccttggaa catttctacc tgaccagtgg caagcagccc aagcaggtgg      300
aagtagagct tttgtcccgg cagagcgggc tctctggccg ccaggtagag cgttggttcc      360
gtcgccgccg caaccaggac cggcccagtc tcctcaagaa gttccgagaa gccagctgga      420
gattcacatt ttacctgatt gccttcattg ccggcatgag agtcattgtg gataaaccct      480
ggttctatga catgaagaaa gtttgggagg gatatcccat acagagcact atcccttccc      540
agtattggta ctacatgatt gaactttcct tctactggtc cctgctcttc agcattgcct      600
ctgatgtcaa gcgaaaggat ttcaaggaac agatcatcca ccatgtggcc accatcattc      660
tcatcagctt ttcctggttt gccaattaca tccgagctgg gactctaatc atggctctgc      720
atgactcttc cgattacctg ctggagtcag ccaagatgtt taactacgcg ggatggaaga      780
acacctgcaa caacatcttc atcgtcttcg ccattgtttt tatcatcacc cgactggtca      840
tcctgccctt ctggatcctg cattgcaccc tggtgtaccc actggagctc tatcctgcct      900
tctttggcta ttacttcttc aattccatga tgggagttct acagctgctg catatcttct      960
gggcctacct cattttgcgc atggcccaca agttcataac tggaaagctg gtagaagatg     1020
aacgcagtga ccgggaagaa acagagagct cagaggggga ggaggctgca gctgggggag     1080
gagcaaagag ccggccccta gccaatggcc acccatcct caataacaac catcgtaaga      1140
atgactgact cgaggg                                                     1156
```

SYSTEM AND METHOD FOR EDITING AND MANIPULATING DNA

CROSS-REFERENCE TO RELATED APPLICATIONS

This application is the U.S. national phase application of PCT International Application No. PCT/IL2008/001629, filed on Dec. 17, 2008, which claims the benefit of U.S. Provisional Application Ser. No. 61/006,042, filed on Dec. 17, 2007, all of which are hereby incorporated by reference in their entirety.

FIELD OF THE INVENTION

The present invention relates to a system and a method for manipulating, processing and editing DNA molecules, and in particular, to such a system and method in which a protocol for synthesizing target DNA molecule is abstracted utilizing a core operation on a given input DNA molecule.

BACKGROUND OF THE INVENTION

Composition and manipulation of DNA molecules are important tasks for molecular biology in both research and industrial applications. While the problem of de novo DNA composition has been addressed systematically (5,10-12,16, 17), no general method for editing DNA molecules is available, and specific editing tasks are presently addressed by specialized labor-intensive methods such as site-directed mutagenesis (1-3) and/or methods relying on the use of restriction enzymes (6, 7).

Biology labs engage daily in manual labor-intensive DNA processing—the creation of variations and combinations of existing DNA—using a plethora of methods such as site-directed mutagenesis (1,2,3), error-prone PCR (4), assembly PCR (5), cleavage and ligation (6,7), homologous recombination (8,9), and others (10,11,12,13,14,15). So far no uniform method for DNA processing has been proposed and, consequently, no engineering discipline has been able to eliminate the manual labor associated with DNA processing.

DNA composition, also called de novo DNA synthesis, is typically achieved by assembling synthetic oligonucleotides into ever longer pieces using one of several methods (17, 18). Although much progress has been made in achieving uniform, efficient and automated methods for performing de novo DNA synthesis, for example by avoiding cloning steps (17), while others use DNA microchips to reduce costs and errors (18) which occur very frequently in these de novo synthesis methods, still these methods suffer from many drawbacks. DNA editing, on the other hand, has no systematic solution to date, and the various editing tasks are performed by a plethora of labor-intensive methods (1-3). Site-directed mutagenesis generates targeted changes including single or multiple nucleotide insertions, deletions or substitutions, generally via the use of an oligonucleotide primer that introduces the desired modification. These fall into two major categories: those based on primer extension on a plasmid template (1-3), and PCR-based methods (13). Other methods use a restriction enzyme to cut the DNA molecule at specific preplanned sites of specific sequence and enable the ligation of a DNA fragment that contains the matching sites on its ends. In this method the short restriction sites must be specific and unique in the sequence to avoid undesired restrictions. Other methods generate random mutations using error-prone PCR, incremental truncation or random DNA shuffling. DNA shuffling performs in vitro homologous recombination of pools of selected homological DNA fragments by random fragmentation and PCR reassembly. However, this methodology is inefficient if multiple non-random sequence manipulations are required, as it requires iterative stages of mutagenesis, cloning, sequencing and selection. Therefore, current DNA processing methods do not provide for seamless DNA editing and manipulations that allow for the abstraction and creation of custom made, designer DNA molecules.

SUMMARY OF THE INVENTION

There is an unmet need for, and it would be highly useful to have, a system and a method for seamless manipulating and editing of existing DNA strands for the purpose of creating customized and/or designer DNA strands. The background art does not teach or suggest a DNA editor, which enables both composition and editing of DNA strands.

The present invention overcomes the drawbacks of the background art by providing a system and method for DNA editing based on a core operation. The core operation according to a preferred embodiment of the present invention enables the system and method of the present invention by providing for seamless DNA editing and manipulation preferably by optimizing the number of core operations required to create the targeted DNA strand.

Representation of a DNA molecule is accomplished by the use of a continuing sequence using a 4 letter code. Each letter of the 4 letter code represents a different nucleic acid found in a DNA strand, namely, A for adenine, T for thymine, C for cytosine and G for Guanine. Therefore, DNA strands, no matter how long may be represented in a textual manner using a running sequence of the 4 letter code. Although a text editor such as MS Word allows composing new text and editing an existing piece of text within the same framework, no such DNA composition, apparatus or system has been made available that allows one to manipulate, edit, visualize or otherwise electronically manipulate DNA strands. Moreover, the background art does not teach or suggest a system or method for the automated production of DNA based on its sequence representation for longer strands. Proof of concept systems have demonstrated the construction of 15 kbp DNA fragments (18), yet such systems still suffer from many drawbacks, including difficulty of use, expense and the potential for introduction of errors.

Therefore an efficient DNA editing method, such as that provided by the present invention, enables extensive manipulation of a DNA molecule while maximizing the use of existing DNA components, similarly to the way a text editor enables efficient editing of an existing text using operation such as insert, delete, substitute, cut, copy and paste. However, no such system, device or method has been offered or made apparent in the background art. The present invention overcomes these drawbacks of the background art and in addition, in at least some embodiments, preferably provides an error free or at least a substantially error free method for such editing, wherein "substantially error free" refers to an error rate of at least less than about 5%, preferably less than about 3%, more preferably less than about 2% and most preferably less than about 1%.

Within the context of this application the term "core operation", "core function", "Y operation", "core Y operation", "Y function", "Y", may be used interchangeably to refer to a process wherein DNA is manipulated, preferably wherein two DNA fragments are concatenated into a single DNA molecule.

Within the context of this application the term editor, DNA editor, DNA processor, DNA manipulation, interchangeably refer to a system and method for editing DNA molecule according to a preferred embodiment of the present invention.

Within the context of this application the term edit, editing, processing or the like collectively refers to at least one or more process, step, reaction or the like measure taken to manipulate DNA for example including but not limited to at least one or more cut, copy, paste, insert, delete, replace, substitute, cut and paste, copy and paste, taken alone or in any combination thereof.

Within the context of this application the term "target", "target molecule", target DNA strand, refers to a DNA molecule that is created by an optional operation of editing an existing DNA molecule according to an optional embodiment of the system and method of the present invention.

Within the context of this application the term "input", "input fragment", "input molecule", "input DNA strand", "input DNA fragment" may be interchangeably used in referring to at least one or more initial DNA molecules used by the system and method of the present invention to create a targeted DNA molecule.

Within the context of this application the terms "DNA fragment", "DNA strand", "DNA molecule", "DNA sequence", may be used interchangeably to refers to an oligonucleic acid sequence.

Within the context of this application the term "division point" refers to any point within a DNA fragment that may be potentially useful for implementing a core Y operation. Preferably, a division point defines a point within a DNA fragment from which at least two, a left and right, flanking sub-sequences may be defined. Most preferably, a core Y operation is utilized to concatenate two different flanking sub-sequences.

According to a preferred embodiment of the present invention, the present invention provides for DNA manipulation and/or editing through the use of a core operation interchangeably referred to a "Y" operation. Most preferably, the Y operation provides for DNA manipulation by joining two double stranded DNA fragments into one double stranded DNA molecule. The core operation according to the present invention may be applied to a plurality of DNA molecules, and is preferably independent of the DNA sequence itself therefore not limiting the core operation to particular DNA sequence.

Preferably, the core operation is independent of the DNA sequence size and may be applied to DNA molecules of varying size. Most preferably, a DNA molecule undergoing a Y operation is amenable to amplification, also most preferably by PCR. Optionally, other amplification techniques as may be implemented with the Y operation according to the present invention. Amplification with PCR provides for a Y operation to be carried out on a DNA molecule of varying size optionally up to 6 kbp, optionally up to 5 kbp, preferably up to 4 kbp, optionally and preferably up to 3 kbp, and most preferably from about 100 bp to about 4 kbp. Optionally and preferably the DNA molecule's size limitation is depicted by the amplification technique utilized.

The core function according to the present invention may optionally and preferably be applied in at least one or more sequences, for example including but not limited to a stepwise manner, in series, in parallel, in sequence, in a loop, or in any repeated manner to provide for DNA editing functions. DNA editing functions may for example include but are not limited to at least one or more of cut, copy, paste, insert, delete, replace, substitute, cut and paste, copy and paste, taken alone or in any combination. Most preferably, a plurality of core operations may be combined together to form a protocol for editing, abstracting, customizing DNA strands.

Among the advantages of the core Y operation, over background art methods, is the independence from site specific restriction enzymes relating to a particular sequence that is that such primers and overlap regions may be defined based on the target region and therefore may be defined for almost any location on a DNA sequence, unlike the use of restriction enzymes which require that a specific restriction site be uniquely embedded within a target DNA fragment.

Most preferably the primers utilized for individual core operation may be designed and optionally selected from an available DNA library. Most preferably the primers are depicted based on the edit protocol performed by at least one Y operation. Primer selection and/or design is optionally dependent on the amplification technique utilized as described above. Optionally the primer utilized comprises up to about 100 bp, more preferably the primers comprise up to about 80 bp in length.

According to a further embodiment, the present invention provides for a method for implementing the core function to produce customized DNA molecules. Preferably, the method according to the present invention utilizes at least one or more input DNA molecules to abstract a protocol applying the core function, according to the present invention, that would produce at least one or more target DNA molecules. Most preferably the abstracted protocol maps a customized targeted DNA molecule that may be composed of at least one or more input DNA molecules by implementing at least one or more core operation according to the present invention. Optionally and preferably, an abstracted protocol may be optimized according to at least one or more controllable factors for example including but not limited to the number of core operations required, the input molecules used, the number of intermediate steps, the number of de novo sequencing steps or processes required, primer's required, primer length, use of shorter primers, use of longer primers, primer melting point (Tm), or the like controllable factors According to some embodiments of the present invention, a method for optimizing the abstracted protocol is provided. Preferably, a Divide-and-Conquer (D&C) DNA editing algorithm is used for determining a protocol of core operations for composing a target DNA molecule from at least one or more available input DNA molecules preferably available in a DNA library.

Most preferably, the method for optimizing and abstracting the protocol comprises: initially defining a target and DNA input library. Next there is preferably a preprocessing phase wherein all potential input DNA fragments, comprising a DNA input library, are evaluated in light of the targeted DNA sequence molecule. Most preferably, the evaluation process provides for the identification of targeted DNA fragment sequences within at least one or more input DNA molecule.

Next, preferably a process is performed to identify and mark all the middle points and end points in the target DNA molecule, defining potential division points based on individual optional DNA input sequences. Next preferably the process involves implementing a recursive protocol planning procedure, which preferably utilizes the divide-and-conquer strategy, wherein each recursive application of the planning procedure, the marked input sequence is divided into two adjacent parts at a selected point defining at least one or more division points. Preferably, a division point is chosen by comparing the target fragment to all input fragments identifying identical subsequences (referred to as NF). Next, the boundaries of each NF are marked.

Next, all potential division points are optionally and preferably considered and scored according to three rules:

a. First, each division point earns a score that is proportional to the sum of the sizes of the largest NFs that are wholly found on both sides of the division point. the larger the target the score. Preferably this is to prevent dividing a large NF in two instead of using it as is.
b. Second, each point is given a penalty that is proportional to the distance from the boundary from the closest NF as this causes the use of synthetic fragments and it is preferable to minimize this.
c. Third, a point is given a small penalty for the distance from the center of the fragment. Given two identical points the construction tree is preferably balanced.

The points are then sorted from high to low score and are considered sequentially. Once the candidate division points are sorted, the best division point is selected and the algorithm tries to plan a basic stage reaction that will combine the two sub-fragments induced by the division point into the target molecule:
a. The necessary primers are planned and validated for specificity, affinity (Tm), dimerization and length constraints for both PCR amplification and Elongation reactions of the basic stage.
b. If valid primers are not found the algorithm continues with the next potential division point.
c. In the case that a valid division point is found the procedure is called recursively on both the left sub-fragment and the right sub-fragment.
d. If a protocol for one of the sub-fragments could not be found the procedure tries the next potential division point.
e. If no possible division is found the recursive procedure call returns with failure value, which causes the calling procedure to try the next best division point.

The recursive division ends when the input to a recursive call can be extracted from one of the input fragments or when it is small enough to be produced as a synthetic oligo.

As output, the algorithm returns the editing protocol in the form of a binary tree. The leaves are either existing DNA fragments (with valid PCR primers) or synthetic oligos. Each internal node corresponds to a dsDNA intermediate product that can be built using a Y operation from its two sons, which result a simple iterative protocol. The root of the tree is the target molecule T. The output of the algorithm also provides the list of primers needed to execute the protocol.

In the absence of relevant input fragments the system preferably defaults to automatic recursive composition of the target molecule from synthetic oligonucleotides.

A further embodiment of the present invention provides for a system that automatically synthesize and edit DNA molecules preferably comprising a user interface for abstracting the protocol for synthesizing a target DNA fragment from existing DNA molecules, at least one or more input DNA fragments to be edited or combined for creating the target DNA fragment, a DNA synthesizer for synthesizing oligonucleotides for performing the editing steps in producing the target DNA molecule by implementing the core function of the abstracted protocol according to the present invention, a PCR machine for carrying out enzymatic reactions. Optionally and preferably the system according to an optional embodiment may further comprise an automatic sequencer preferably for determining, testing and repairing the produced target sequences Unless otherwise defined the various embodiment of the present invention may be provided to an end user in a plurality of formats, platforms, and may be outputted to at least one of an assembly line, a robot, a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B are schematic diagrams illustrating exemplary embodiments of the core operation according to the present invention.

FIGS. 2A-I are exemplary molecular DNA editing functions made possible by implementing the core operation of FIGS. 1A-1B.

DESCRIPTION OF THE PREFERRED EMBODIMENTS

Figures 2F, 2G:
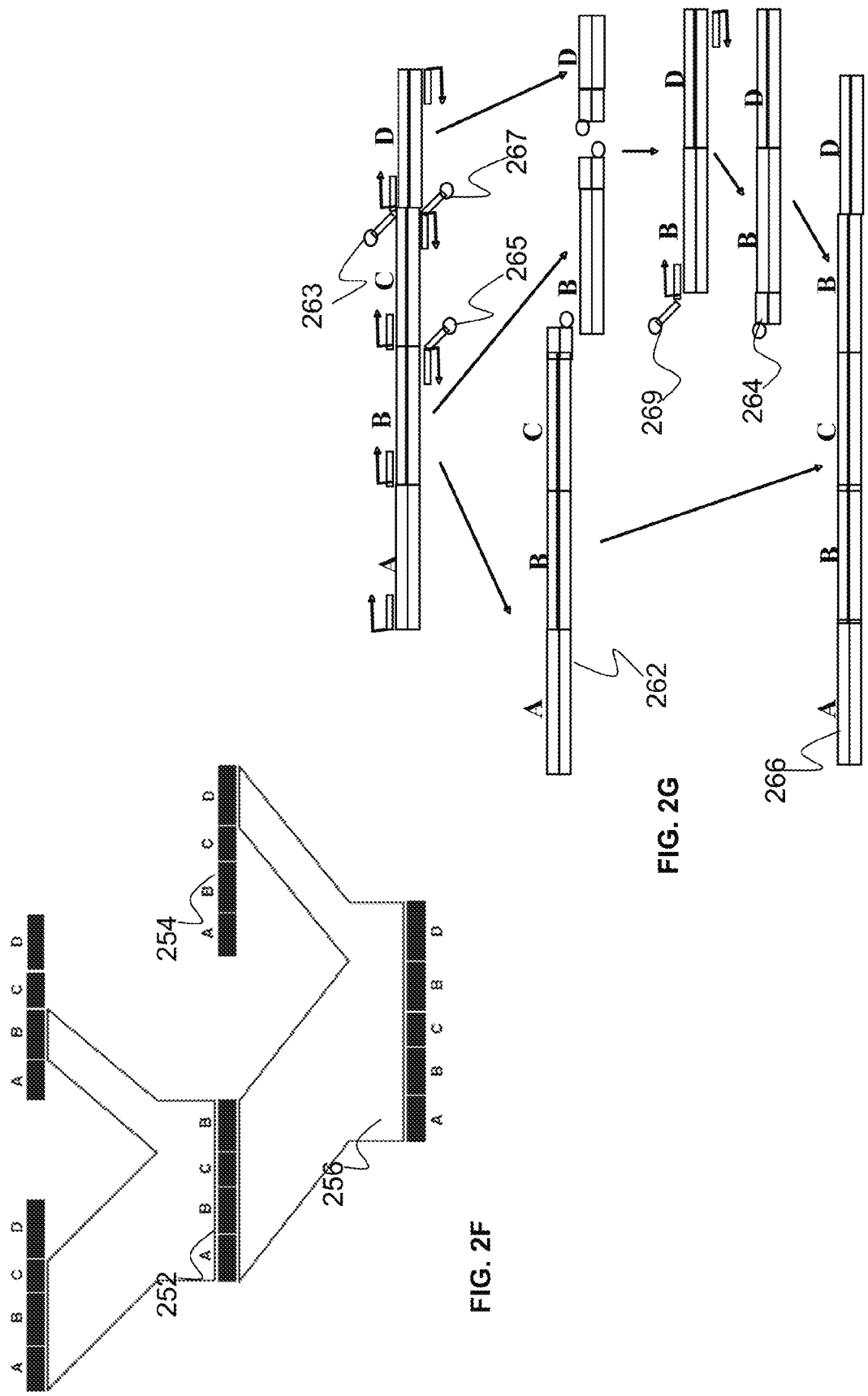

The present invention is of a system and a method creating customized targeted DNA molecules from existing input DNA molecules. Targeted DNA sequences are preferably obtained by manipulating and editing exiting DNA molecules therein saving the costs, effort and errors associated with de-novo synthesis of DNA sequences. Most preferably the DNA editor according to the present invention rely on a core operation that when implemented in various combination on different DNA molecules may bring about more complex editing operation. The present invention relates to a system and a method for manipulating, processing and editing DNA molecules, and in particular, to such a system and method in which a protocol for synthesizing target DNA molecule most preferably from existing input DNA molecules is abstracted utilizing a core operation on a given input DNA molecule.

The principles and operation of the present invention may be better understood with reference to the drawings and the accompanying description.

FIG. 1A provides a schematic diagram of the core operation according to the present invention wherein a first DNA input fragment A is concatenated with a second DNA input fragment B to form a targeted DNA fragment AB, that is preferably and optionally a concatenated DNA molecule of the input DNA fragments.

Most preferably, the core Y operation may be utilized to edit DNA in a plurality of ways for example providing for edit operations for example including but not limited to at least one or more cut, copy, paste, insert, delete, replace, substitute, cut and paste, copy and paste, taken alone or in any combination thereof. Preferably, the core Y operation may be implemented on a plurality of DNA forms for example including but not limited to single stranded, double stranded or partially hybridized DNA, or the like.

Optionally, at least one or more of the input fragments may be found within a common DNA fragments. Optionally, at least one or more of the input fragments may be found on individual DNA fragments.

FIG. 1B depicts the method by which the core Y operation depicted in FIG. 1A is most preferably implemented. In stage 110 DNA fragments A and B form are defined as an input DNA fragment A and B which are to be concatenated. In stage 112, DNA input fragments A and B are amplified, preferably using PCR, with primers 114 preferably comprising an overhang to produce overlapping dsDNA 112. Most preferably primers 114 are phosphorylated at their 5' end, most preferably comprising up to about 80 bp. Most preferably stage 112 produces a phosphorylated double stranded primer extended input DNA molecule 116. In stage 118 the phosphorylated double stranded primer extended input DNA molecules 116 are digested, preferably producing two overlapping single stranded DNA 120. Preferably, the digestion is undertaken with an exonuclease for example including but not limited to a λ-exonuclease. Most preferably the overlap region enables each of the single stranded DNA 120 to anneal and associate with one another forming complex 122. Most preferably the overlapping region of complex 122 is corresponds to primer 114. In stage 124 complex 122 is preferably elongated producing the targeted DNA sequence 124, most preferably a concatenated sequence comprising the input DNA fragments A and B. Most preferably, elongation is achieved with a mutual elongation with a DNA polymerase. Optionally and preferably, the polymerase used in stage 124 is in quasi-equilibrium, wherein the PCR process is amended to provide slow heating and cooling processes preferably improving the energetic efficiency of the reaction.

FIGS. 1A and 1B provide a depiction of the core Y operation according to the present invention. However, for the core Y operation to be successful it must be appropriately planned according to a preferred embodiment of the present invention. Most preferably, the core operation must be planned due to chemical constraints that allow for the concatenation of individual input DNA fragments. For example, primer 114 and overlap specificity are chemical constraints that must be addressed to ensure the success of the core Y operation. However, the chemical constraints provide the strength and flexibility of the preferred embodiment of the present invention. Among the advantages of the core Y operation, over background art methods, is the targeted approach, allowing it to be independent of limitations associated with background art methods comprising the use of site specific restriction enzymes that must be related to a particular sequence within a targeted DNA molecule. Moreover, the targeted design provided by the system and method of the present invention is such that primers and overlap regions may be defined based on the target region and therefore may be defined for almost any location on a given DNA sequence.

FIG. 2A-I depicts a plurality of optional editing functions provided for by the implementation of the core Y operation, for example including but not limited to at least one or more of cut, copy, paste, insert, delete, replace, substitute, cut and paste, copy and paste, taken alone or in any combination thereof. The edit operations depicted in FIGS. 2A-I are made possible with the implementation of a plurality of performances, in varying combinations, of the basic core Y operation.

FIG. 2A depicts the paste operation of wherein input DNA sequences A, B, C and D are concatenated to form the targeted DNA strand ABCD. Optionally, the core operation depicted in FIG. 1A may be applied in 3 instances to form the targeted sequence 206. Optionally, a first Y operation may be implemented wherein input DNA fragment A is concatenated with input DNA fragment B to form an intermediate DNA fragment AB 202. Similarly a second core Y operation may be implemented wherein input DNA fragment C is concatenated with input DNA fragment D to form an intermediate DNA fragment CD 204. A third core Y operation may be implemented to concatenate intermediate DNA fragments AB 202 and intermediate DNA fragments CD 204 to form the targeted DNA fragment 206. The target DNA molecule 206 may be formed in a plurality of optional combination of using at least one or more core operation. A preferred embodiment of the present invention provides for the identification of the optimized use of the Y operation in creating a protocol map specific to a target DNA molecule based on the available input DNA sequences.

FIG. 2B depicts the insert operation wherein a first input DNA sequence C is inserted in a second input DNA sequence AB to form the target DNA molecule ACB 216. Optionally, the core operation depicted in FIG. 1A may be applied in 2 instances to form the targeted sequence 216. Optionally, a first Y operation may be implemented wherein an input DNA fragment AB is manipulated to delete a subsection B of the input DNA fragment while replacing it by concatenating with input DNA fragment C to form an intermediate DNA fragment AC 212. Therein a single Y operation subsequence B of the input DNA fragment was deleted and replaced by the second input DNA fragment. Similarly a second core Y operation may be implemented wherein input DNA fragment AB is selectively manipulated to delete a subsection A while associating with associated with intermediate DNA fragments AC 212 to form the targeted DNA fragment 216.

FIG. 2C depicts the delete operation wherein a single Y operation may be utilized to provide a target sequence AC 226 from two copies of a single input sequence ABC. The move from the input sequence ABC to the target sequence AC may be provided with a single Y core operation where proper primer selection and planning could provide to concatenate two subsection namely A and C originating from the same input DNA sequence ABC. The primer selection providing such an edit operation would be specific for the A subsection of the input molecule and the C subsection of the input molecule. Therein two copies of the input DNA molecule ABC are selectively concatenated to form the target DNA molecule AC 226 therein effectively deleting the B subsection of the input DNA molecule.

FIG. 2D provides an example of a replace edit function, wherein a particular sequence B within an input sequence of ABC is replaced to form the targeted DNA strand ADC. A first Y operation is performed to produce an intermediate DNA sequence AD that is then associated with the input DNA sequence ABC, however careful primer selection provides for specifically concatenation subsection C of input DNA sequence ABC with the intermediate DNA sequence AD forming the targeted sequence ADC.

FIG. 2E depicts an optional protocol to carry out a cut and past edit function utilizing the core operation depicted in FIG. 1A. For example, an input DNA sequence ABCD may undergo editing to form the target sequence ACBD 246 by cutting the B subsection of the ABCD input sequence and pasting it prior to the D subsection. Optionally, a variety of Y operations may be implemented to synthesize the target molecule from the input molecule. For example, a first Y operation may provide an intermediate DNA strand 242 comprising the sequence equivalent to AC by cutting out both the B sub-sequence and the D sub-sequence of the input molecule. Most preferably this first Y operation is accomplished by utilizing primers that are specific to the A and C sub-sequences. A second Y operation may be implemented to provide intermediate DNA strand 244 comprising the sequence equivalent to BD by cutting out both the A sub-sequence and the C sub-sequence of the input molecule. Most preferably this second Y operation is accomplished by utilizing primers that are specific to the B and D sub-sequences, effectively joining the two sub-sequences. A third Y operation is implemented to provide the targeted molecule ACBD 246 most preferably by concatenating the two intermediate DNA strands AC 242 and BD 244. Most preferably, concatenation of the two intermediate strands is implemented with a Y operation as described in FIGS. 2A and 1B wherein primers are selected for the overlap region or fusion point wherein subsequence C and B intersect to form the target molecule ACBD 246.

FIGS. 2F and 2G depict optional protocols to carry out a copy and paste edit function utilizing the core operation depicted in FIG. 1A both based on the same input sequence ABCD and forming the target sequence ABCBD. FIG. 2F shows input DNA sequence ABCD may undergo editing to form the target sequence ABCBD by copying the B subsection of the input sequence and pasting it prior to the D subsection. Optionally a variety of Y operations may be implemented to synthesize the target molecule from the input molecule. For example, a first Y operation may provide an intermediate DNA strand 252 comprising the sequence equivalent to ABCB by providing a copy of the B sub-sequence and replacing the D sub-sequence. A second Y operation may be implemented to provide the target molecule ABCBD 256 by utilizing a Y operation between intermediate sequence 252 and the input sequence ABCD 254 to paste the D sub-sequence onto the intermediate sequence 252 forming the target sequence ABCBD 256.

FIG. 2G depicts the same input DNA molecule ABCD and target sequences ABCBD, however utilizing a different set of Y operations based on different primers. The core Y operations are utilized to create intermediate sequences ABC 262 and BD 264 that are concatenated in a final Y operation to produce the targeted sequence ABCBD 266. The primers used to obtain the intermediates define the Y operation utilized to bring about the target sequence. For example, complementary primers 263 and 265 provide for the Y operation that links the D sub-sequence with the B subsequence that gives rise to the BD 264 intermediate. Similarly, complementary primers 267 and 269, wherein primer 267 comprises a B sub-sequence overhand with a C sub-sequence, will eventually provide for the Y operation that concatenates the two intermediates 262 and 264 to create the target sequence ABCBD.

Figures 2H, 2I:
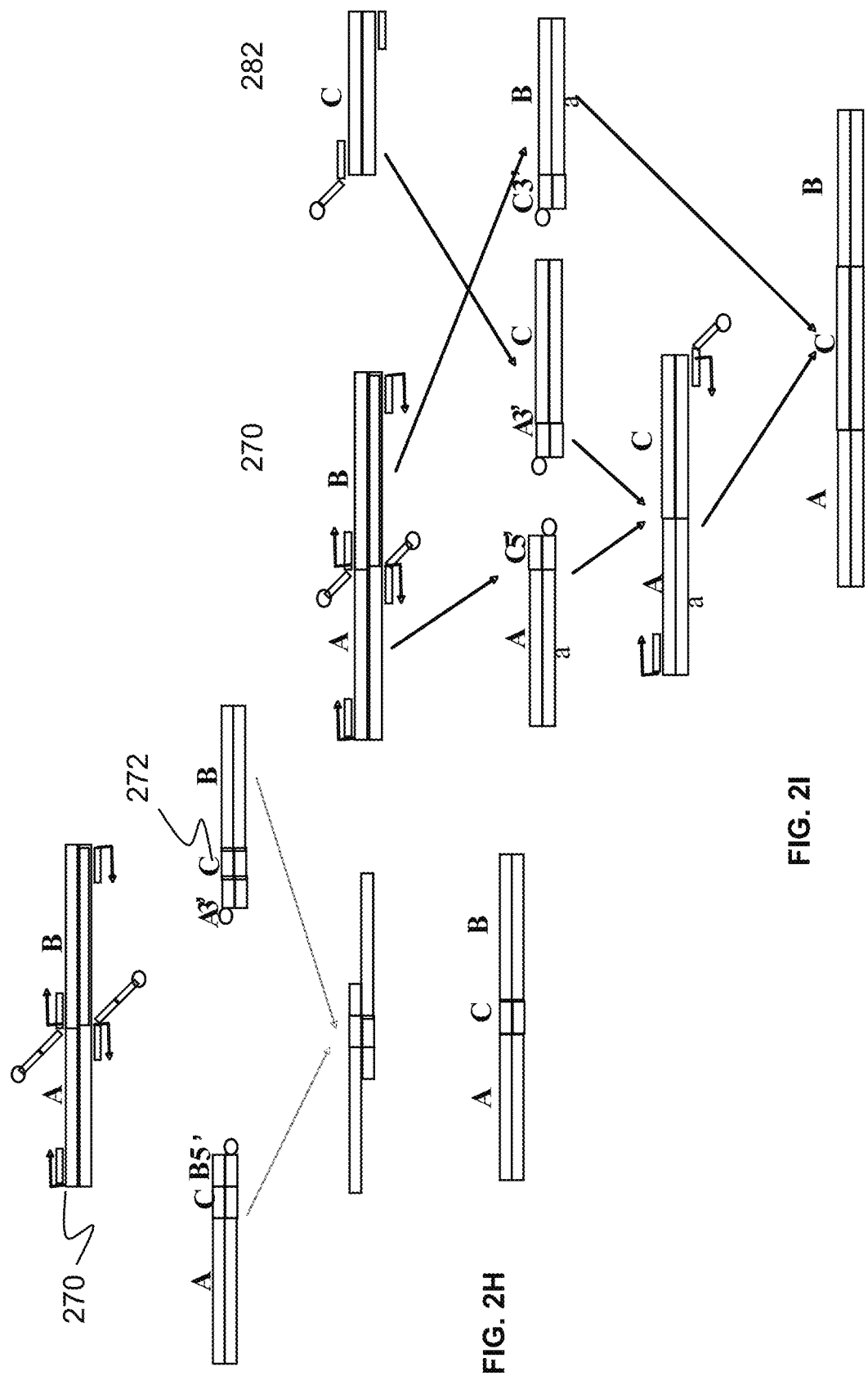

The difference between FIGS. 2F and 2G is the protocol utilized to obtain the target sequence from the input sequence. Optionally, either protocol may be used however the method according to a preferred embodiment of the present invention may prefer one or the other depending on at least one or more optimization factors, for example including optimizing the use of available primers, time, number core operations required, use of intermediate products for parallel use, relative size of the fragments that are concatenated or the like optimization factors FIGS. 2H and 2I further depict how primer optimization, target sequence and available input molecules determine the number of Y operations required to perform a the same editing task. For example, FIG. 2H depicts a single Y operation required to insert a short DNA sequence C 272 into an input sequence AB 270. Similarly, FIG. 2I depicts an insertion edit operation into the same input sequence AB 270 however the DNA sequence C 282 inserted is a larger one. Optionally, for small enough insertion sequences a single Y operation may be utilized, through primer extension, as depicted in FIG. 2H. For small sequence insertions the primer utilized is optionally up to about 100 bp and most preferably up to about 80 bp, including the insertion sequence itself. Primer size limitation is dependent on the amplification process utilized for example including but not limited to PCR. Most preferably, the size limitation of the small insert is dependent on the primer utilized, most preferably up to about 80 bp. For a larger insertion sequence, as depicted in FIG. 2I, a plurality of Y operations and a larger number of primers are required to bring about the insert edit function.

Optionally, when implementing small insertion or deletion sequences, for example up to five codon sequences or 15 bases the edit may be implemented through a single Y operation by effectively choosing the appropriate primer related to the insertion or deleted sequence.

Figures 3A, 3B:
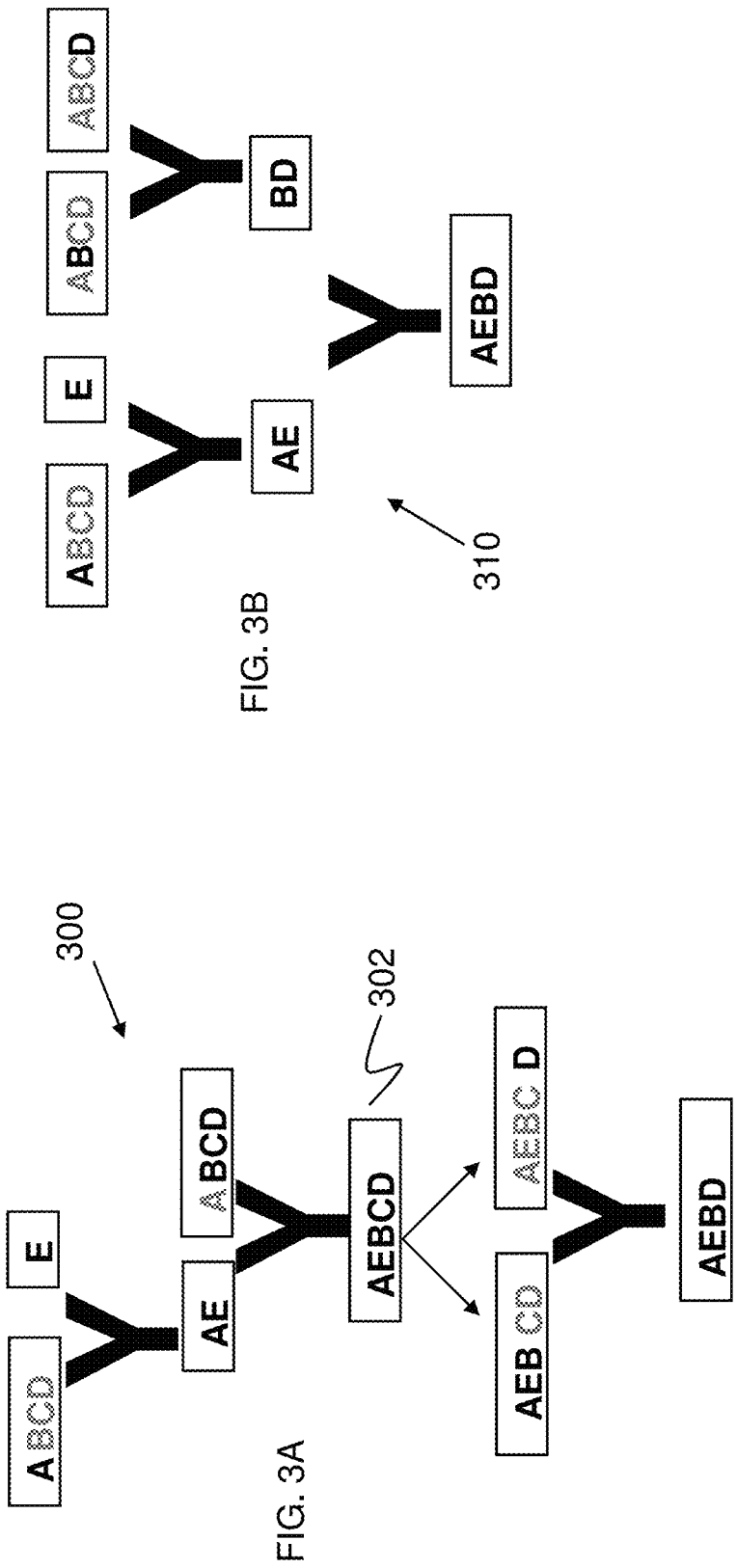
FIGS. 3A-B are exemplary optional insert edit function protocols according to the present invention wherein the same input and target molecules are utilized however using a different pathway and intermediates.

FIGS. 3A and 3B further provides a depiction of the two different pathways that may be utilized to obtain the same target DNA sequence from the same input DNA sequence. Optimization preferably provided by the system and method of the present invention could be based on the primers available, intermediate sequences required elsewhere in the process, chemical constraints or the like factors and or variables that may be optimized. For example, in some situation protocol 310 depicted in FIG. 3B may be preferred as it utilized parallel Y operations. While in other situation protocol 300 of FIG. 3A would be preferred because of the need for the AEBCD intermediate sequence 302 elsewhere in a parallel process (not shown).

Figure 4:
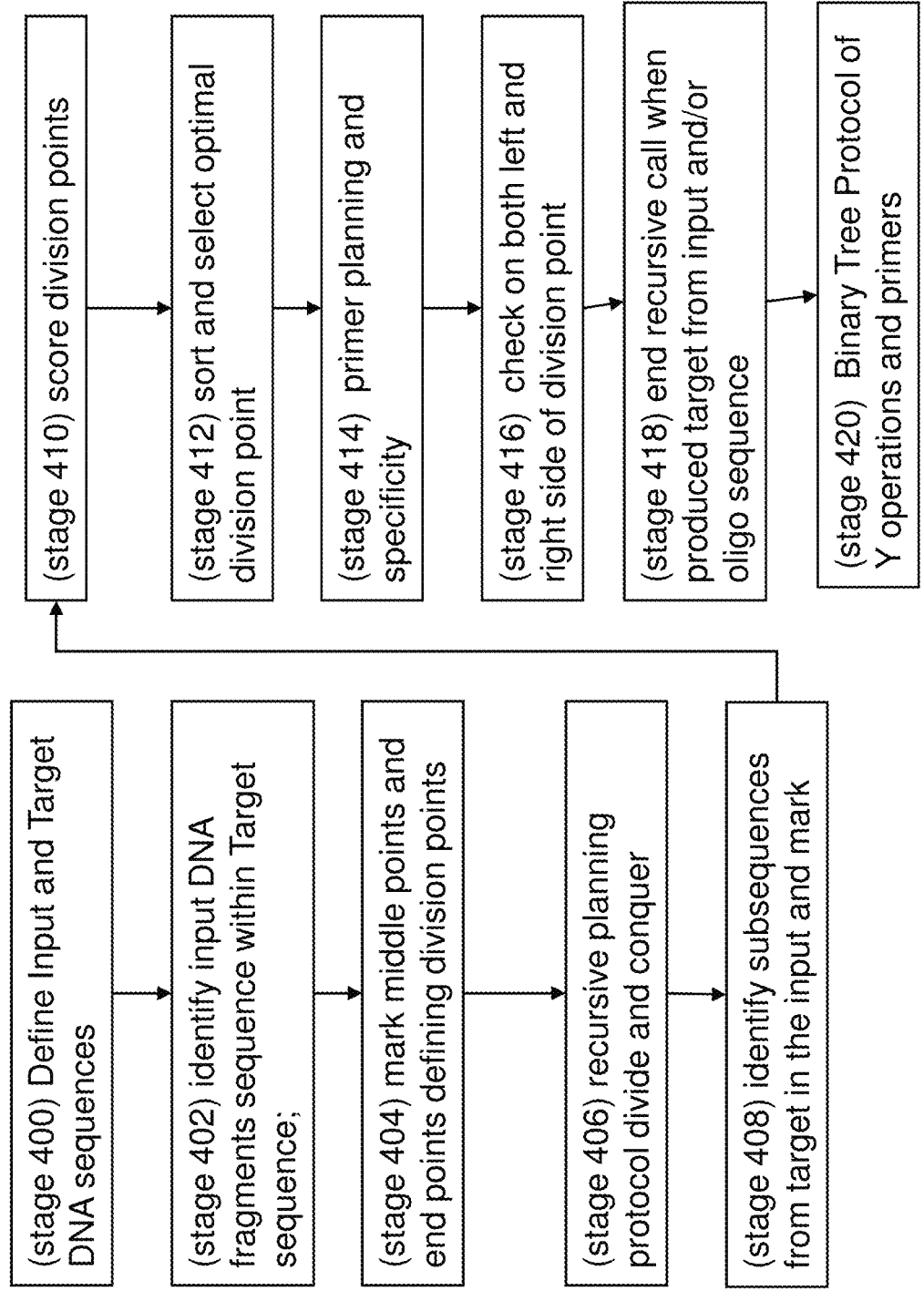
FIG. 4 is a flow chart of a method according to exemplary embodiments of the present invention for abstracting an editing protocol using core operation.

FIG. 4 depict an exemplary embodiment of the optimization method according to the present invention where an editing protocol is devised based on a targeted DNA sequences and available input DNA sequences. The method according to an optional embodiment is preferably used to determine which of available editing sequences are to be used for example as shown in FIG. 3A and FIG. 3B by optimization at least one or more factors for example including but not limited to available input DNA sequences, available primers, intermediate sequences required, chemical constraints, sequence of events performed in parallel versus sequential core operations, number of core operations, the amount of input fragments reuse or the like.

In stage 400 at least one or more target DNA sequences and input DNA sequences are preferably defined. Optionally and preferably, available input sequences are chosen from a library or repository of DNA sequences, for example including but not limited to available DNA sequences, primers, enzymes, known genes, commercial sources of DNA, known genomes and the like.

Next in stage 402, a preprocessing phase is performed wherein all input DNA fragments in the target DNA molecule are identified. In stage 404 all input DNA fragments identified in stage 402 are marked preferably at various points along the input sequence for example including but not limited to at least one or more middle points and/or end points that correspond and correlate the input and target DNA sequences.

In stage 406, a recursive protocol planning procedure is implemented, preferably utilizing the divide-and-conquer strategy. Preferably, the marked input sequence is divided into two adjacent parts, namely the left sub-sequence and the right sub-sequence, at a selected point defining at least one or more division points. Preferably, a division point is chosen according to at least one or more criteria for example including but not limited to input fragment use, sequence of events performed in parallel versus sequential core operations and balancing the size of the left sub-sequence and the right sub-sequence or the like.

In stage 408 input fragments which are relevant to each sub-sequence or sub-target are identified (referred to as NF) and marking the boundaries of each NF within the context of the subsequence.

In stage 410 all potential division points are considered and scored according to at least three preferred rules. A first rule is optionally wherein division point earns a score that is preferably proportional to the sum of the sizes of the largest NFs that are wholly found on both sides of the division point; more preferably, the larger the NF within the target, the larger the score. This rule prevents dividing a large NF in two instead of using it as whole.

A second rule is preferably implemented to minimize the number of fragments not found within the input DNA fragment library. Each point is given a penalty that is more preferably proportional to the distance from the boundary of the closest NF. A third rule occurs wherein a division point is given a small penalty, preferably proportional to the distance from the center of the NF. Preferably, the third rule enables a decision to be made between two optional protocols associated with two identical division points. Most preferably the third rule provides for selecting a more preferable and balanced editing protocol tree.

Once scored, individual division points are then sorted in stage 412, most preferably in a descending order based on a score, from high to low score. Each division point is preferably then considered sequentially.

In stage 414, the method according to the present invention most preferably attempts to abstract and/or map at least one or more core Y operation that will combine the two sub-fragments (NF) induced by the division point into the target molecule. Preferably, in stage 414 the necessary primers are planned and validated according to at least one or more factors, for example including but not limited to specificity, affinity, melting temperature Tm, nonspecific dimerization with themselves, nonspecific dimerization with other primers and length constraints. Elongation overlap is also evaluated at this stage including overlap specificity, affinity (Tm), nonspecific dimerization with themselves, nonspecific dimerization with other single stranded fragments and length constraint. Most preferably, primer and overlap validation is performed for both PCR amplification and elongation reactions of the core Y operation. Optionally and preferably, if valid primers are not found the method continues to evaluate the next potential division point, preferably returning to stage 412.

Optionally and preferably, if valid primers are found for a division point, the procedure is called recursively in stage 416 on both the left sub-fragment and the right sub-fragment, preferably returning to stage 408 for each subsequence. Optionally and preferably, if a protocol for at least one of the sub-fragments is not found the procedure attempts the next potential division point, preferably returning to stage 412. Optionally and preferably, if no possible valid division point is found, most preferably the recursive procedure call returns with failure value preferably which causing the calling procedure to try the next best division point.

In stage 418, preferably the recursive division ends when the input to a recursive call can be extracted from one of the input fragments or when it is small enough to be produced in the preferable method of de novo DNA synthesis, preferably cheaply using DNA synthesis machine.

In stage 420 preferably the editing protocol is returned, based upon the output of the above stages, most preferably in the form of a binary tree, as depicted in FIG. 5. Optionally, the protocol may be provided in a plurality of formats for example as a set of instructions to an entity including but not limited to a user, a computer, a robot in at least one or more optional formats for example comprising but not limited to an assembly line, a robot, a computer readable memory, a computer display device, a printer, another computer on a network or a user. A further output of the algorithm comprises a list of primers needed to execute the protocol.

Figure 5A:
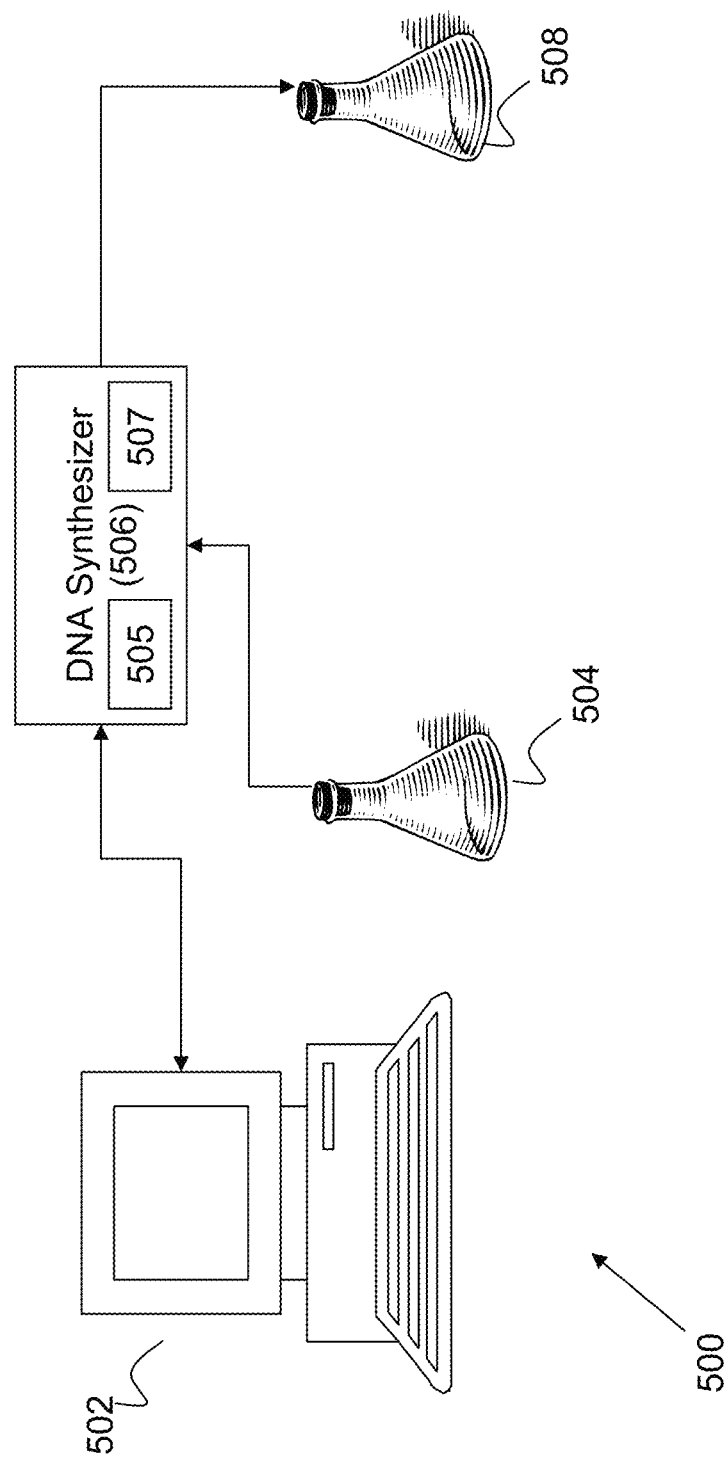
FIGS. 5A-B are schematic block diagrams of an exemplary system according to some embodiments of the present invention for producing targeted DNA molecules by implementing the core operation.

FIG. 5A depicts an optional embodiment of the present invention with a system 500 that preferably automatically synthesizes and edits DNA molecules from a library of input DNA molecules. System 500 preferably comprises a user interface 502 for abstracting the protocol for synthesizing a target DNA fragment most preferably from an existing library DNA molecules 504, at least one or more input DNA fragments to be edited or combined for creating the target DNA fragment 508, and a DNA synthesizer 506 for synthesizing performing the editing steps in producing the target DNA molecule by implementing the core function of the abstracted protocol according to the present invention. Optionally and preferably, system 500 may further comprise a PCR machine 505 for carrying out the enzymatic reactions. Optionally and preferably system 500 according to an optional embodiment may further comprise an automatic sequencer 507 preferably for determining, testing and repairing the produced target sequences.

As described in the Examples below, the experimental methods were preferably performed by using a laboratory robot. As an illustrative, non-limiting example only, the Tecan Genesis Laboratory Robot can be used. This robot is a modular and programmable open platform. It consists of a modular table space and two robotic arms. The table can be equipped with various carriers and racks for tubes, microplates, tips and reagents, as well as external integrated equipment such as a PCR machine, vacuum manifold, plate readers, etc. One of the robot arms is the liquid handling arm or LIHA, which features 8 disposable-tip pipettes. Each pipette is connected to a different syringe and is thus capable of handling different volumes simultaneously. The LIHA can detect the liquid level in each tube automatically using the robot's disposable tips and can set each pipette to a different height accordingly. A second robot arm is the Robotic Manipulation Arm (ROMA) which can handle square shaped objects such as microplates, and can load or unload them onto the robot's integrated devices. The robot is controlled by a personal computer (PC) using a software program called Gemini (developed by Tecan Group Ltd.). This program enables the user to run robot scripts called GEM files. The GEM files are in fact files written in the robot assembly language that includes information regarding the robot table organization as well as the script flow. Gemini also supplies the user with a graphic user interface environment for the development of GEM file scripts.

Another role of Gemini is to maintain the system definitions. The definitions include the properties of standard carriers and racks for tubes and microplates and liquid handling policies for various types of liquids and tips. This set of definitions can be extended by an advanced user to integrate new equipment to the robot system.

Figure 5B:
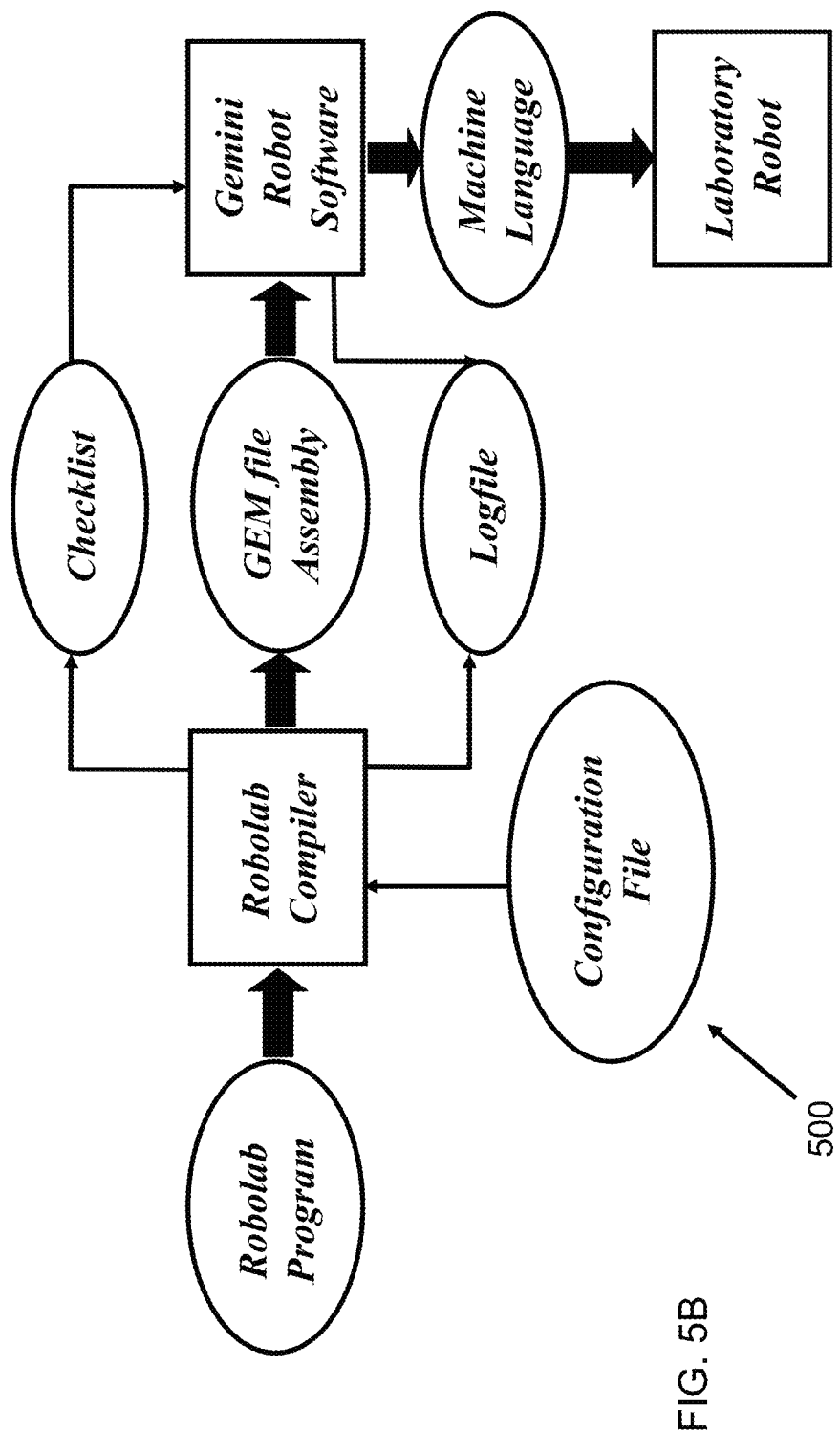

Actual development of scripts and performance of the experiments was done through the Robolab development environment, shown in more detail in FIG. 5B. The Robolab environment includes several processing units, the compiler, the Gemini Software and the Robot.

A Robolab experiment program is written as a text file and is compiled using a compiler called robocom.pl (The compiler is implemented in Perl). The compiler compiles the Robolab experiment program into a GEM file. The GEM file, which is written in the robot assembly language can be executed by the Gemini software, and performs the experiment automatically. The compiler also validates correctness of the program and reports when errors are detected. For this purpose it uses a system configuration file that contains description of the table organization and other pre-defined system information. This enables the compiler to validate that the program may run on the current configured system. Besides the GEM file, the compiler produces a checklist which is used during the actual run-time of the compiled script and is aimed to validate the precondition of the system. In addition, the compiler produces a log file which documents the experiment. This log file is further updated during run-time logging events as they are happening. The Robolab program file and all other files produced by the compiler are located in the user experiment directory which helps the user to track their many experiments more easily. The system global configuration files and the code are located in a global area and thus make the maintenance of the system and its environment easier.

EXAMPLE 1

Experimental Implementation

To check the viability of the Y operation to implement basic editing operations, the editing steps depicted in FIG. 2 were applied to the editing of a 700 bp molecule containing the Gal10 promoter in yeast into 5 variants (Table 1). The planning and validation of the chemical constraint validation were performed the using DNA Editor software constructed according to the present invention. The output included the required primers (Table 2) and a target construction plan as described in greater detail below, which graphically specify assembly process and the resulting reactions plan. The sequence of the desired edit target (see target sequences in Table 1) was achieved within the first iteration of the protocol with no need for error correction. Simple de novo synthesis is expected to yield an error rate of about 1/400 (starting from purified oligos which result in additional cost) in the first iteration, which will require about 20 clones for each of the target sequences in order to achieve error-free sequence with probability of 95%. Thus the results demonstrate that editing an existing DNA molecule one can significantly improve the time of production, the cost of reagents and the effort involved in error-correction compared to de novo DNA synthesis.

Synthetic Process Description—

Figure 6A:
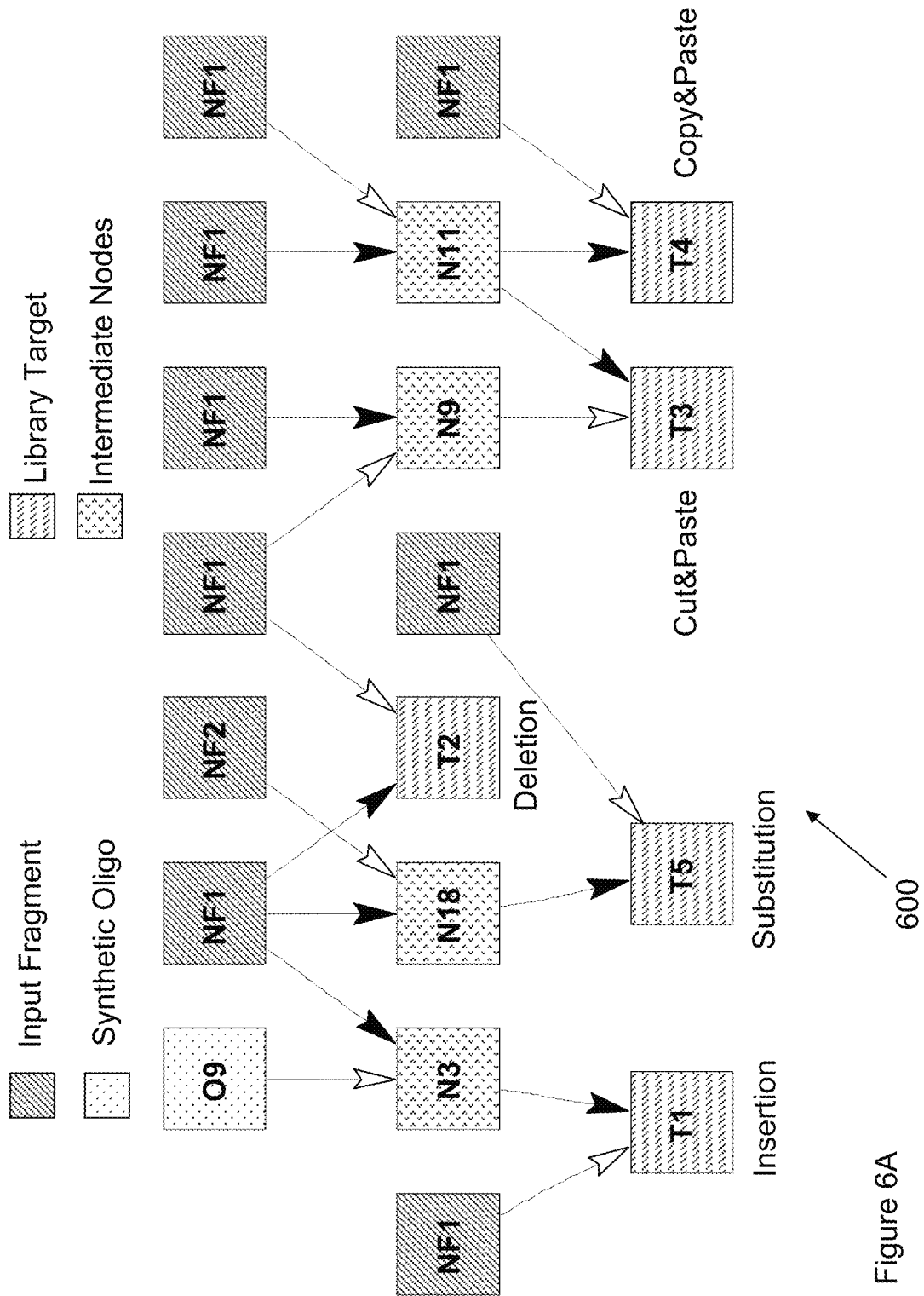
FIG. 6A provides an exemplary editing protocol map according to the system and method of the present invention in the form of a binary tree, as illustrated in Example 1.

FIG. 6A depicts an exemplary editing protocol map in the form of a binary tree 600 as provided by a preferred embodiment of the system and method of the present invention, for performing the edit processes described in this Example. Optionally and preferably, the leaves of the binary protocol tree comprise either existing DNA input fragments NF1, preferably having valid PCR primers, or synthetic oligos DNA input sequence O9. Each internal node corresponds to a dsDNA intermediate N3, N18, N9, N11 product that can be built using a Y operation, as described above, from its two sons, which result in a simple iterative protocol. The root of the tree is the target molecule optionally comprising at least one or more targets T1, T2, T3, T4, T5. Boxes comprising a light upward diagonal pattern represent certain parts of a given input molecule. The dotted patterned box represents an oligonucleotide which is used to insert a sequence which is not available in the input molecules and divot patterned boxes represent intermediate nodes used solely for the construction. The arrow color (white or black) indicates whether the source molecule (located at the tail of the arrow) is composed as the left or the right side in the target molecule (located at the head).

Figure 6B:
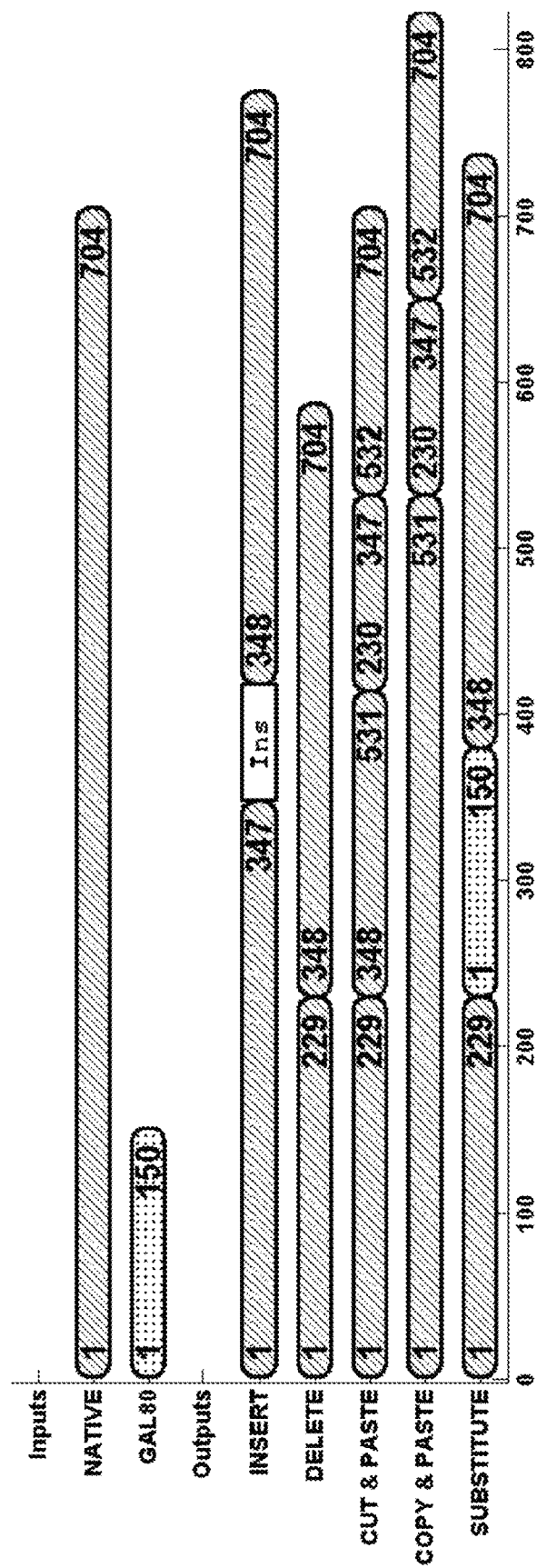
FIG. 6B provides a schematic diagram of the input and output DNA molecules provided for by the editing protocol binary tree of FIG. 6A as non-limiting examples only.

FIG. 6B is of a diagram depicting various editing operations performed on the input molecule NATIVE (see table 1). An additional input molecule, GAL80 (see table 1), is used to demonstrate substitution. In the output section, five editing operations are demonstrated. Each colored ellipse designates a part of an input molecule, identified by the color, and the numbers are coordinates inside the input molecule, in nucleotides.

Materials & Methods

Phosphorylation:

300 pmol of single stranded DNA in a 50 µl reaction containing 70 mM Tris-HCl, 10 mM $MgCl_2$, 7 mM dithiothreitol, pH 7.6 at 37° C., 1 mM ATP & 10 units T4 Polynucleotide Kinase (NEB). Reaction is incubated at 37° C. for 30 min, then at 42° C. for 10 min and inactivated at 65° C. for 20 min.

Elongation:

1 pmol of single stranded DNA of each progenitor in a 25 µl reaction containing 25 µl of 10× ABGene Thermo-Start Standard Buffer (no $MgCl_2$), 1.5 mM $MgCl_2$, 200 µM of each of dNTPs, 4 units Thermo-Start DNA Polymerase (ABGene). Thermal Cycler program is: Enzyme activation at 95° C. for 15 min, cooling at 0.1° C./sec to 62° C., and holding for 10 sec, elongation at 72° C. for 10 min.

PCR:

1-0.1 fmol template, 10 pmol of each primer in a 32.5 µl reaction containing 60 mM TRIS-Cl, 6 mM $(NH_4)_2SO_4$, 10 mM KCl, 2 mM $MgSO_4$, 250 µM of each of dNTPs, 1.875 U of AccuSure DNA Polymerase (BioLine), SYBR Green diluted 1:50,000. Thermal Cycler program is: 1× Enzyme activation at 95° C. 10 min. 20× Denaturation 95° C. for 10 sec, Annealing at Tm of primers for 30 sec, Extension 72° C. for 1 min per kbp of template.

Digestion by Lambda Exonuclease:

1-5 pmol of 5' phosphorylated DNA termini in a 30 µl reaction containing 67 mM Glycine-KOH, 2.5 mM $MgCl_2$, 0.01% Triton X-100, 5 mM 1,4-Dithiothreitol, 5.5 units Lambda Exonuclease (Epicentre) and SYBR Green diluted 1:50,000. Thermal Cycler program is 37° C. for 15 min, 42° C. for 10 min, Enzyme inactivation at 65° C. for 10 min.

Mixes Preparation

Premade mixes, prepared according to the above recipes, for Phosphorylation, Elongation, PCR and Lambda Exonuclease Digestion (including enzymes and buffers) were mixed at a 5× concentration and added to the reaction.

Chemical Oligonucleotide Synthesis

Oligonucleotides for all experiments were ordered by IDT or from Weizmann in-house oligonucleotides synthesis unit. All oligonucleotides undergo standard desalting.

Automated DNA Purification:

Automated DNA Purification was performed with Zymo ZR-96 DNA Purification kit in 96 well plate format using standard protocols. All centrifugations were done at 2000 g for 5 min.

Liquid Handling

All liquid handling except for mixes preparation were done on a Tecan Freedom 2000 robot controlled by in-house developed software. Mixes preparation were done by hand.

Capillary Electrophoresis

5' fluorescently tagged primers, tagged either with FAM or HEX fluorophores were ordered from IDT and mixed with identical non-fluorescent primers at 1% (m/m) concentration. 1 µl of PCR or elongation products were mixed with 15 µl pure formamide containing ladder (by ABI). Fragment analysis was done on an ABI 3130 Genetic Analyzer.

Cloning

Fragments were cloned into the pGEM-T easy Vector System1 from PROMEGA using standard procedures. Vectors containing cloned fragments were transformed into JM109 competent cells from PROMEGA1 using standard procedures. Cells were plated onto agar plates with LB+AMP antibiotics (by Hy Laboratories Ltd.) and incubated at 37° C. for 1-2 days.

Sequencing

Single colonies were picked manually from the plates and transferred to 50 µl PBS buffer.

Plasmids were amplified in vitro using the commercial kit Templiphi (by GE Healthcare).

Amplified plasmids were sent to sequencing in house using the standard primers SP6 & T7 (see pGEM-T manual).

TABLE 1

Target sequences

NATIVE
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTACGGATTAGAAGCCGCC
GAGCGGGCGACAGCCCTCCGACGGAAGACTCTCCTCCGTGCGTCCTCGT
CTTCACCGGTCGCGTTCCTGAAACGCAGATGTGCCTCGCGCCGCACTGC
TCCGACAATAAAGATTCTACAATACTAGCTTTTATGGTTATGAAGAGG
AAAAATTGGCAGTAACCTGGCCCCACAAACCTTCAAATTAACGAATCAA
ATTAACAACCATAGGATGATAATGCGATTAGTTTTTTAGCCTTATTTCT
GGGGTAATTAATCAGCGAAGCGATGATTTTTGATCTATTAACAGATATA
TAAATGGAAAAGCTGCATAACCACTTTAACTAATACTTTCAACATTTTC
AGTTTGTATTACTTCTTATTCAAATGTCATAAAAGTATCAACAAAAAAT
TGTTAATATACCTCTATACTTTAACGTCAAGGAGAAAAAACTATAATGT
TAATTAAGGATCCATCGA

GAL80
CCTTTCTTCTCTCCCCTGCAATATAATAGTTTAATTCTAATATTAATAA
TATCCTATATTTTCTTCATTTACCGGCGCACTCTCGCCCGAACGACCTC
AAAATGTCTGCTACATTCATAATAACCAAAAGCTCATAACTTTTTTTTT
TGA

EDT1_T1
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTACGGATTAGAAGCCGCC
GAGCGGGCGACAGCCCTCCGACGGAAGACTCTCCTCCGTGCGTCCTCGT
CTTCACCGGTCGCGTTCCTGAAACGCAGATGTGCCTCGCGCCGCACTGC
TCCGTCCACAACATATAAGTAAGATTAGATATGGATATGTATATGGTGG
TAATGCCATGTAATATGATTATTAAAACAATAAAGATTCTACAATACTA
GCTTTTATGGTTATGAAGAGGAAAAATTGGCAGTAACCTGGCCCCACAA
ACCTTCAAATTAACGAATCAAATTAACAACCATAGGATGATAATGCGAT
TAGTTTTTTAGCCTTATTTCTGGGGTAATTAATCAGCGAAGCGATGATT
TTTGATCTATTAACAGATATATAAATGGAAAAGCTGCATAACCACTTTA
ACTAATACTTTCAACATTTTCAGTTTGTATTACTTCTTATTCAAATGTC
ATAAAAGTATCAACAAAAAATTGTTAATATACCTCTATACTTTAACGTC
AAGGAGAAAAAACTATAATGTTAATTAAGGATCCATCGA

EDT1_T2
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTAAACAATAAAGATTCTA
CAATACTAGCTTTTATGGTTATGAAGAGGAAAAATTGGCAGTAACCTGG
CCCCACAAACCTTCAAATTAACGAATCAAATTAACAACCATAGGATGAT
AATGCGATTAGTTTTTTAGCCTTATTTCTGGGGTAATTAATCAGCGAAG
CGATGATTTTTGATCTATTAACAGATATATAAATGGAAAAGCTGCATAA
CCACTTTAACTAATACTTTCAACATTTTCAGTTTGTATTACTTCTTATT
CAAATGTCATAAAAGTATCAACAAAAAATTGTTAATATACCTCTATACT
TTAACGTCAAGGAGAAAAAACTATAATGTTAATTAAGGATCCATCGA

TABLE 1-continued

Target sequences

EDT1_T3
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTAAACAATAAAGATTCTA
CAATACTAGCTTTTATGGTTATGAAGAGGAAAAATTGGCAGTAACCTGG
CCCCACAAACCTTCAAATTAACGAATCAAATTAACAACCATAGGATGAT
AATGCGATTAGTTTTTTAGCCTTATTTCTGGGGTAATTAATCAGCGAAG
CGATGATTTTTGATCTATTAACGGATTAGAAGCCGCCGAGCGGGCGACA
GCCCTCCGACGGAAGACTCTCCTCCGTGCGTCCTCGTCTTCACCGGTCG
CGTTCCTGAAACGCAGATGTGCCTCGCGCCGCACTGCTCCGCAGATATA
TAAATGGAAAAGCTGCATAACCACTTTAACTAATACTTTCAACATTTTC
AGTTTGTATTACTTCTTATTCAAATGTCATAAAAGTATCAACAAAAAAT
TGTTAATATACCTCTATACTTTAACGTCAAGGAGAAAAAACTATAATGT
TAATTAAGGATCCATCGA

EDT1_T4
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTACGGATTAGAAGCCGCC
GAGCGGGCGACAGCCCTCCGACGGAAGACTCTCCTCCGTGCGTCCTCGT
CTTCACCGGTCGCGTTCCTGAAACGCAGATGTGCCTCGCGCCGCACTGC
TCCGAACAATAAAGATTCTACAATACTAGCTTTTATGGTTATGAAGAGG
AAAAATTGGCAGTAACCTGGCCCCACAAACCTTCAAATTAACAATCAA
ATTAACAACCATAGGATGATAATGCGATTAGTTTTTAGCCTTATTTCT
GGGGTAATTAATCAGCGAAGCGATGATTTTTGATCTATTAACGGATTAG
AAGCCGCCGAGCGGGCGACAGCCCTCCGACGGAAGACTCTCCTCCGTGC
GTCCTCGTCTTCACCGGTCGCGTTCCTGAAACGCAGATGTGCCTCGCGC
CGCACTGCTCCGCAGATATATAAATGGAAAAGCTGCATAACCACTTTAA
CTAATACTTTCAACATTTTCAGTTTGTATTACTTCTTATTCAAATGTCA
TAAAAGTATCAACAAAAAATTGTTAATATACCTCTATACTTTAACGTCA
AGGAGAAAAAACTATAATGTTAATTAAGGATCCATCGA

EDT1_T5
ATCGACCCGGGCATTTATATTGAATTTTCAAAAATTCTTACTTTTTTTT
TGGATGGACGCAAAGAAGTTTAATAATCATATTACATGGCATTACCACC
ATATACATATCCATATCTAATCTTACTTATATGTTGTGGAAATGTAAAG
AGCCCCATTATCTTAGCCTAAAAAAACCTTCTCTTTGGAACTTTCAGTA
ATACGCTTAACTGCTCATTGCTATATTGAAGTACCTTTCTTCTCTCCCC
TGCAATATAATAGTTTAATTCTAATATTAATAATATCCTATATTTTCTT
CATTTACCGGCGCACTCTCGCCCGAACGACCTCAAATGTCTGCTACAT
TCATAATAACCAAAAGCTCATAACTTTTTTTTTGAAACAATAAAGATT
CTACAATACTAGCTTTTATGGTTATGAAGAGGAAAAATTGGCAGTAACC
TGGCCCCACAAACCTTCAAATTAACGAATCAAATTAACAACCATAGGAT
GATAATGCGATTAGTTTTTAGCCTTATTTCTGGGGTAATTAATCAGCG
AAGCGATGATTTTTGATCTATTAACAGATATATAAATGGAAAAGCTGCA
TAACCACTTTAACTAATACTTTCAACATTTTCAGTTTGTATTACTTCTT
ATTCAAATGTCATAAAAGTATCAACAAAAAATTGTTAATATACCTCTAT
ACTTTAACGTCAAGGAGAAAAAACTATAATGTTAATTAAGGATCCATCG
A

TABLE 2

Primers

| | |
|---|---|
| EDT1_O2 | ATCGACCCGGGCATTTATATT |
| EDT1_O2 | TCGATGGATCCTTAATTAACATTATAG |
| EDT1_O3 | GTGGACGGAGCAGTGCGGCGC |
| EDT1_O4 | CGCCGCACTGCTCCGTCCACAACATATAAGTAAGATTAGATATGGATA |
| EDT1_O5 | TCCACAACATATAAGTAAGATTAGATATGGATA |
| EDT1_O6 | TCGATGGATCCTTAATTAACATTATAGT |
| EDT1_O7 | CTTTATTGTTTTAATAATCATATTACATGGCATTACCAC |

TABLE 2-continued

Primers

| | |
|---|---|
| EDT1_O8 | TGTATATGGTGGTAATGCCATGTAATATGATTATTAAACAATAAAGATTCTACAATACTAGCT |
| EDT1_O9 | TCCACAACATATAAGTAAGATTAGATATGGATATGTATATGGTGGTAATGCCATGTAATATGATTATTAA |
| EDT1_O10 | CTTTATTGTTTACTTCAATATAGCAATGAGCAG |
| EDT1_O11 | CTTAACTGCTCATTGCTATATTGAAGTAAACAATAAAGATTCTACAATACTAGCT |
| EDT1_O12 | TTCTAATCCGTTAATAGATCAAAAATCATCGCTTCG |
| EDT1_O13 | GAAGCGATGATTTTTGATCTATTAACGGATTAGAAGCCGCC |
| EDT1_O14 | ATCGACCCGGGCATTTATATTGAAT |
| EDT1_O15 | TAATAGATCAAAAATCATCGCTTCG |
| EDT1_O16 | ACGGATTAGAAGCCGCC |
| EDT1_O17 | TTATATATCTGCGGAGCAGTGCGGCGC |
| EDT1_O18 | CCGCACTGCTCCGCAGATATATAAATGGAAAAGCTGC |
| EDT1_O19 | GAGAAGAAAGGTACTTCAATATAGCAATGAGCAG |
| EDT1_O20 | GCTCATTGCTATATTGAAGTACCTTTCTTCTCTCCCTGCA |

EXAMPLE 2

DNA Editing Algorithm for Combinatorial Variant Library

This Example relates to the application of the above-described method for a combinatorial variant library, by using the divide and conquer approach that extends the above described DNA editing method. Since a typical variant library contains many DNA fragments that are shared between the library variants, it is desired to produce shared fragments only once and re-use them as larger building blocks for building other variants. A divide and conquer algorithm computes an efficient protocol that minimizes the cost, time and effort of library production by maximizing the reuse of shared library components. The result of the algorithm is a compact protocol that converges towards the largest shared fragments of the entire variants library. Those large shared fragments are built only once and then reused as a building block for the construction of the final targets.

Given a set of target DNA sequences which are combinatorial variant library of one original template, the method provides an efficient D&C edit protocol for the construction of all the targets while maximizing reuse of shared library components.

Algorithm:

Input: a set of target sequences T which are variant library of one original sequence and existing sequences S.

Pre-Processing:

Go over all the sub-sequences of all the variants that are larger than or equal to a given length MIN_FRAGMENT_SIZE. For each sub-sequence count the number of occurrences in the final products.

For each sequence compute a score which reflects the amount of final library products. The size multiplied by the number of occurrences.

FRAGMENT_SCORE=FRAGMENT_SIZE*FRAGMENT_NUMBER.
Store the fragment score in a FRAGMENTS_DB
Divide & Conquer:
For each of the sequences in T:
The target sequence is given as the initial input for a divide and conquers recursive protocol planning subroutine.
At each recursive step the target sequence is divided at each step into two adjacent parts.
The division point is selected as follows:
　All possible division points are considered. The current candidate division is denoted by CURR_CANDIDATE
　Find the maximal scoring fragment in FRAGMENT_DB that matches the sequence that ends in CURR_CANDIDATE. This fragment is called MAX_LEFT.
　Find the maximal scoring fragment in FRAGMENT_DB that matches the sequence that starts after the CURR_CANDIDATE. This fragment is called MAX_RIGHT.
　The score of the current point CURR_CANDIDATE is calculated by the sum of the two adjacent maximal fragments.
　CANDIDATE_SCORE=MAX_LEFT+MAX_RIGHT The CANDIDATE_SCORE is registered in a list SCORE_LIST for each candidate point.
The SCORE_LIST is sorted to determine the priority of each point for division.
Thus each candidate point is scored according to the sum of the two maximal fragments scores that starts and ends exactly at this point. Thus points which are exactly adjacent to fragments which have large score (reflecting the fact that they are shared by many of the final products) will be preferred for division in many of the target that share them (See intuitive explanation below).
The selected division point is validated for fulfilling the chemical constraints of the basic edit step (See basic chemical step in the DNA edit paper).
The recursive division ends when one of the following occurs:
　The current fragment was already planned (as part of previous target for example)
　The current fragment is found within an existing fragment from S.
　The current fragment is in the size of an oligo that can be synthesized.
If a valid division could not be found (for example, due to chemical constraints) the recursion subroutine returns failure and the next best scoring candidate is selected.
Each division result in two nodes in a graph that are connected to the node which was divided (their parent node). The division continues recursively for the two new nodes.
In case of success the graph node ID of the current subtarget is returned to the calling level.
The output of the algorithm is a set of instructions, preferably in the form of a directed graph which describes the protocol to build the library. Each node in the graph corresponds to DNA fragment. Each node has at most two incoming edges that describe from which nodes it is assembled. A shared component has more than one outgoing edge, reflecting the fact that it is reused.

EXAMPLE 3

A Protein-Variant Library for Protein Design

This Example relates to creating a library of different variations on a particular protein, for example for protein design. For example the DNA of a gene coding for a protein with a known function and structure may be available; however, it may be desired to improve the protein's activity (for example, its catalytic activity or binding affinity). It is possible to screen for a variant of the original protein by replacing the amino acids near the known sites of activity. Typically, desired amino acid mutations occur along the entire length of the DNA coding for the protein, which makes changing several amino acids difficult. Moreover, predicting the result of mutations is difficult, and often it is required to make several mutations before finding a suitable protein.

Figure 7A:
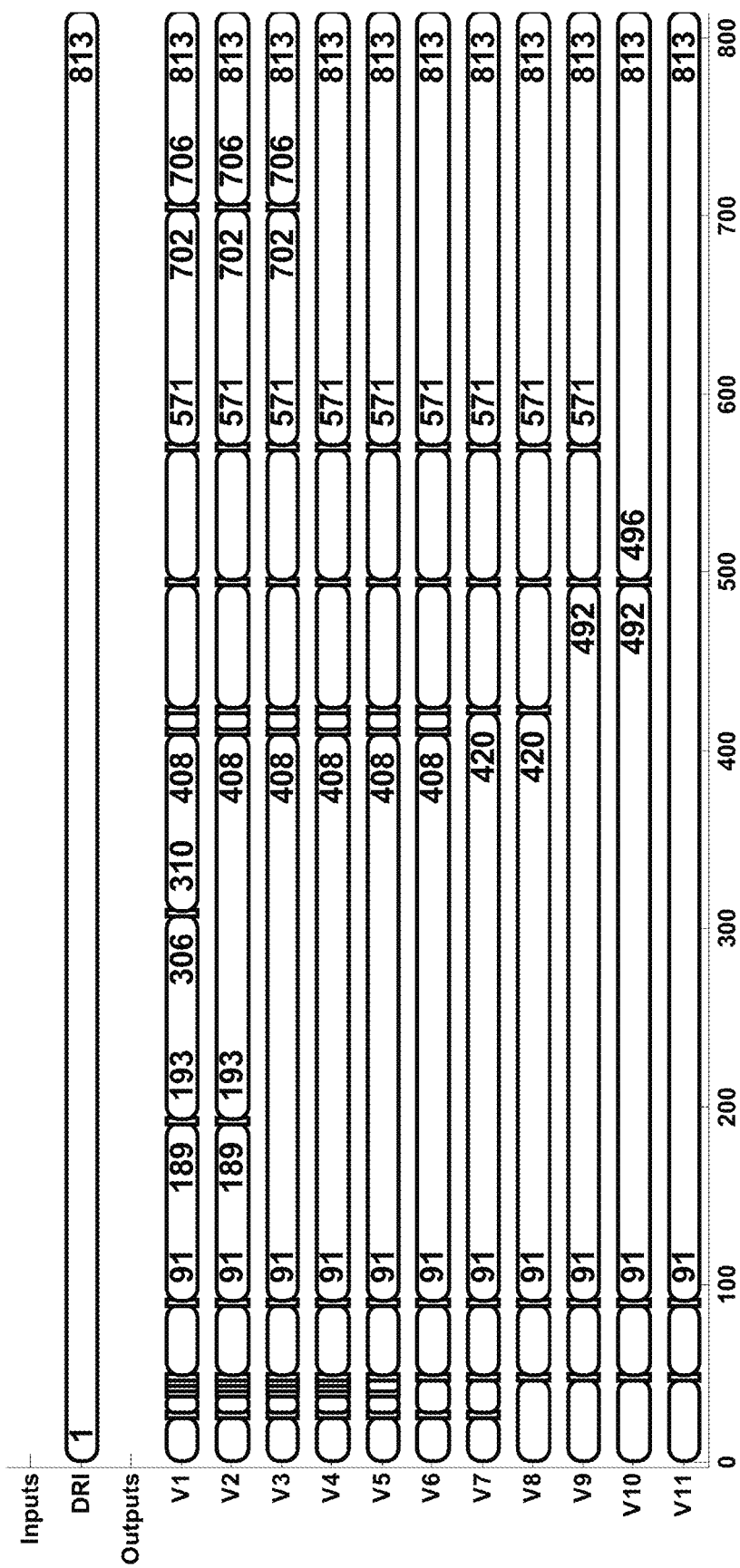
FIG. 7A provides schematic diagrams of the input and output DNA molecules provided for by an optional, exemplary editing protocol as depicted in Example 3 as non-limiting examples only.
Figure 7B:
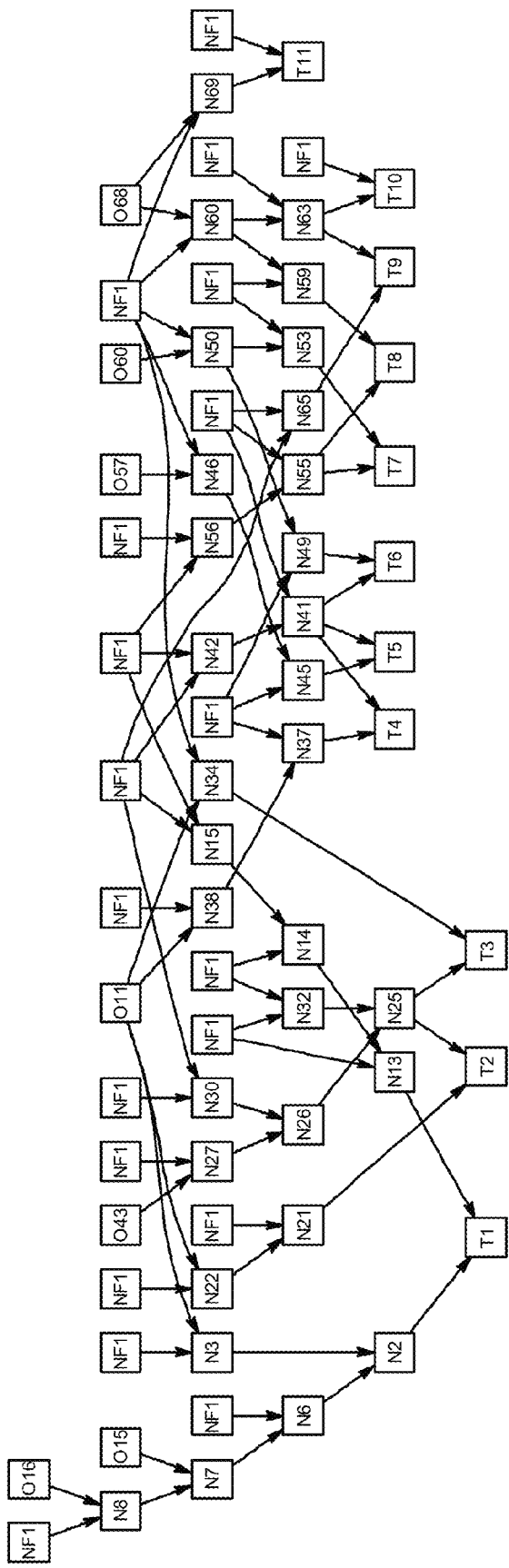
FIGS. 7B-D provide schematic diagrams of exemplary editing protocol maps in the form of a binary tree according to some illustrative embodiments of the system and method of the present invention, relating to the input and output sequences of FIG. 7A.

This example demonstrates the ability of the method of the present invention, in this embodiment, to make up to 12 mutations concurrently and thus efficiently and quickly with only 5 iterations of the construction process (see FIG. 7B).

Figure 7C:
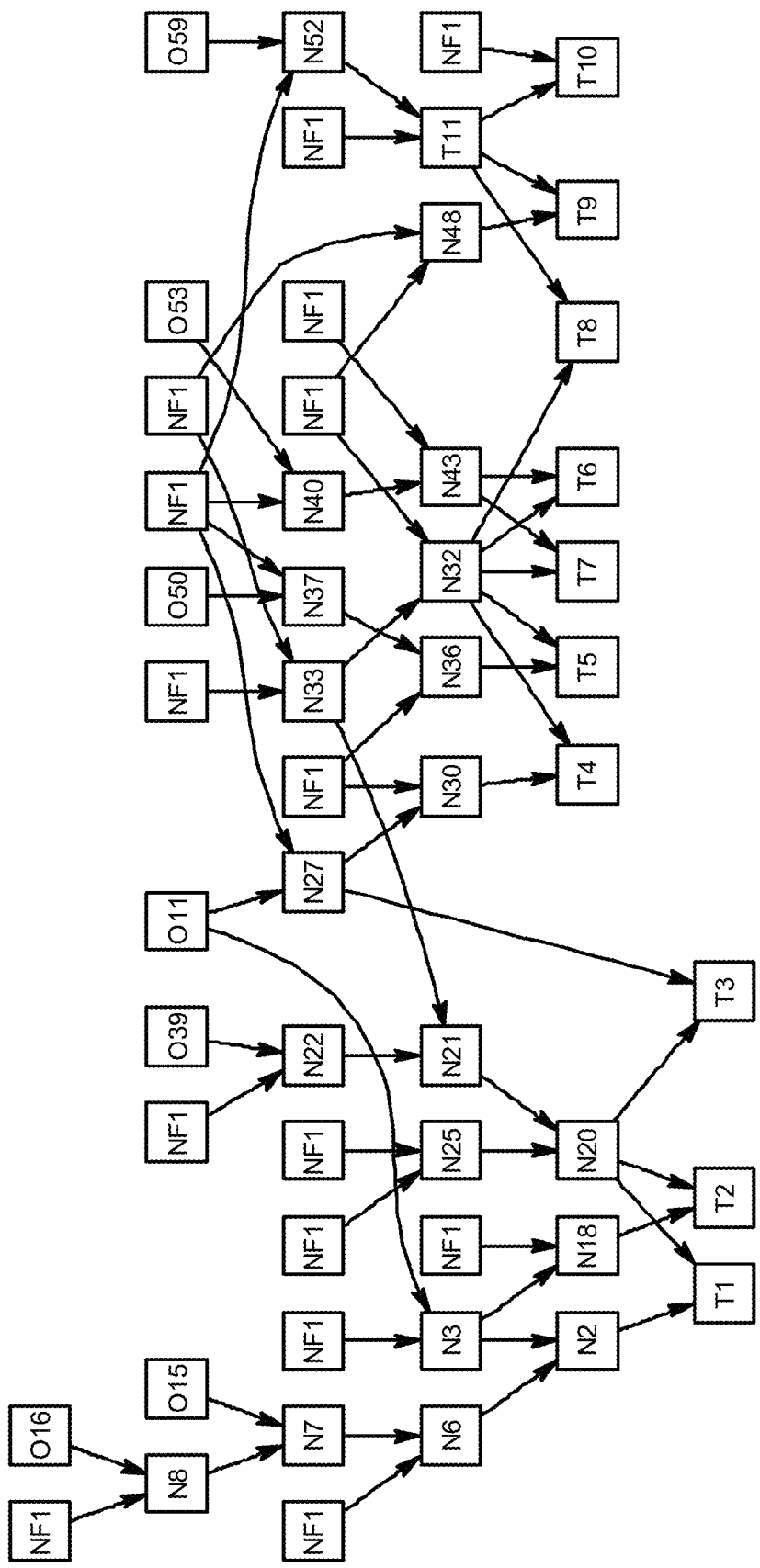
Figure 7D:
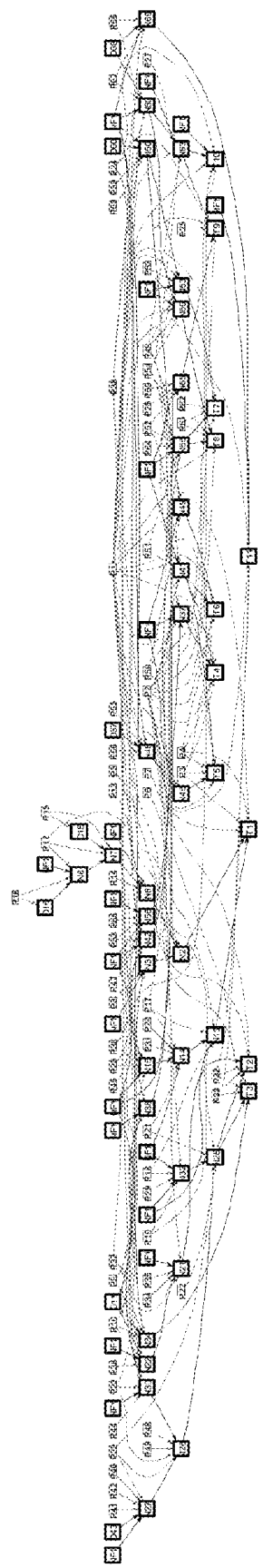

In this Example, one such gene, DRI (see table 3, DRI1_NF1), which is 813 bp long, was used to create a library of 11 mutants which were later used for the optimization of its affinity. FIG. 7a illustrates the desired sequences as a function of the input gene, each with 2 to 12 amino acid substitutions. The editing protocol map (FIG. 7b) has a depth of 5 levels and demonstrates both efficient utilization of the available DNA molecule as well as the sharing of library components among different variants. Since the Y operation can use as input a fragment embedded in a longer sequence, a further optimization is possible, by eliminating graph nodes that represent a fragments contained in other nodes, and using the containing node as the source of the Y operation instead (FIG. 7c). FIG. 7D demonstrates the difficulty of manually performing these editing tasks by showing the full reaction protocol, including all the primers that take part in the process. This complex graph is translated into a robot control program that when executed performs the specified edit protocol. In reality, each arrow in the graph is translated into one or more reagent transfer in the robot program.

The complete set of sequences is shown in Table 3 below. The sequences were created according to the methods described in FIG. 7D and the methods described with regard to Example 1; upon sequencing, no errors were found (data not shown).

TABLE 3

DRI example sequences
DRI1_NF1 is the input molecule (DRI). DRI1_T1 through DRI1_T11 correspond to V1 through V11. DRI1_P1 through DRI1_P69 are the oligos used by the protocol.

| Name | Length | Sequence |
|---|---|---|
| DRI1_P1 | 22 | AAAGATACCATTGCGCTGGTGG |
| DRI1_P2 | 28 | TTGTTTCACAACTAACTTCAGGTCTACG |
| DRI1_P3 | 28 | TCCCGGGCATCGCTTGTACCAGCGATGC |
| DRI1_P4 | 29 | TGGTACAAGCGATGCCCGGGAATGGGGGG |
| DRI1_P5 | 18 | CGCTTGTACCAGCGATGC |
| DRI1_P6 | 37 | TCGGTAGGATCTATAAGCAAGATTTTTGTCCCACGGA |
| DRI1_P7 | 48 | TCCGTGGGACAAAAATCTTGCTTATAGATCCTACCGACTCAGATGCCG |

TABLE 3-continued

DRI example sequences
DRI1_NF1 is the input molecule (DRI). DRI1_T1 through DRI1_T11 correspond to V1 through V11. DRI1_P1 through DRI1_P69 are the oligos used by the protocol.

| Name | Length | Sequence |
|---|---|---|
| DRI1_P8 | 27 | CTATAAGCAAGATTTTTGTCCCACGGA |
| DRI1_P9 | 38 | TCAAAGAGACTTCCCACGGTTCATTTAACGTTTCAACC |
| DRI1_P10 | 40 | CGTTAAATGAACCGTGGGAAGTCTCTTTGAAGGACGGCGC |
| DRI1_O11 | 48 | AAAGATACCATTGCGCTGGTGGTTGAAACGTTAAATGAACCGTGGGAA |
| DRI1_P12 | 21 | ATCCTACCGACTCAGATGCCG |
| DRI1_P13 | 34 | GTACATTGTCTTCTGCAATATGGGACACGACTTC |
| DRI1_P14 | 45 | TCGTGTCCCATATTGCAGAAGACAATGTACTCGGTGGGAAAATCG |
| DRI1_P15 | 60 | TTCTGCAATATGGGACACGACTTCGCCCTTAGTGGCCTGATCATCCAGCGTGATAACGGG |
| DRI1_P16 | 26 | GATCATCCAGCGTGATAACGGGAATG |
| DRI1_P17 | 18 | ATGCCCGGGAATGGGGGG |
| DRI1_P18 | 29 | TCCGGCAATTCTGCTATAGTGGCCGCCAG |
| DRI1_P19 | 35 | GGCCACTATAGCAGAATTGCCGGATCAGATCGGTG |
| DRI1_P20 | 18 | TGCTATAGTGGCCGCCAG |
| DRI1_P21 | 30 | TTTCATCTTCTTGGGCGAACACAGCCTGTA |
| DRI1_P22 | 38 | GCTGTGTTCGCCCAAGAAGATGAAATGGCACTGGGTGC |
| DRI1_P23 | 20 | TTGGGCGAACACAGCCTGTA |
| DRI1_P24 | 29 | TTCGATCATCGTCTGCCGGTTGAGAGGCT |
| DRI1_P25 | 38 | TCAACCGGCAGACGATGATCGAATTAAGGGCCTGAATG |
| DRI1_P26 | 36 | ATGCCCGGGAATGGGGGAGGGATTTCAACAGGCAG |
| DRI1_P27 | 19 | GTCTGCCGGTTGAGAGGCT |
| DRI1_P28 | 27 | GATGATCGAATTAAGGGCCTGAATGTT |
| DRI1_P29 | 24 | GAAGATGAAATGGCACTGGGTGCG |
| DRI1_P30 | 40 | TCAACCGGCAGACGATGATCGAATTAAGGGCCTGAATGTT |
| DRI1_P31 | 39 | GCTGTGTTCGCCCAAGAAGATGAAATGGCACTGGGTGCG |
| DRI1_P32 | 33 | TTAGTGGCCTGATCATCCAGCGTGATAACGGGA |
| DRI1_P33 | 31 | ACGCTGGATGATCAGGCCACTAAGGGCGAAG |
| DRI1_P34 | 36 | CGGTAGGATCTATAAGCAAGATTTTTGTCCCACGGA |
| DRI1_P35 | 43 | GGGACAAAAATCTTGCTTATAGATCCTACCGACTCAGATGCCG |
| DRI1_P36 | 26 | TATAAGCAAGATTTTTGTCCCACGGA |
| DRI1_P37 | 25 | ATCATCCAGCGTGATAACGGGAATG |
| DRI1_P38 | 22 | ATCCAGCGTGATAACGGGAATG |
| DRI1_P39 | 19 | CAGGCCACTAAGGGCGAAG |
| DRI1_P40 | 34 | GCCCGGGAATGGGGGAGGGATTTCAACAGGCAG |
| DRI1_P41 | 18 | TCCCGGGCATCGCTTGTA |
| DRI1_P42 | 35 | CCCTCGCCGGCCTTTTTCGCTATGTAATCTCCAGC |
| DRI1_O43 | 34 | TCCCGGGCATCGCTTGTACCAGCGATGCCCTGCA |
| DRI1_P44 | 22 | GGGGAGGGATTTCAACAGGCAG |
| DRI1_P45 | 39 | CAACCGGCAGACGATGATCGAATTAAGGGCCTGAATGTT |
| DRI1_P46 | 53 | GCGAAAAGGCCGGCGAGGGTGCAAAAGTTATTGAACTGCAGGGCATCGCTGG |
| DRI1_P47 | 31 | AATTCGATCATCGTCTGCCGGTTGAGAGGCT |
| DRI1_P48 | 32 | ATCCCTCCCCCCATTCCCGGGCATCGCTTGTA |
| DRI1_P49 | 32 | TGGCCTGATCATCCAGCGTGATAACGGGAATG |
| DRI1_P50 | 19 | CGCTTGTACCAGCGATGCC |
| DRI1_P51 | 30 | CCATTTCATCTTCTTGGGCGAACACAGCCT |
| DRI1_P52 | 39 | CTGTGTTCGCCCAAGAAGATGAAATGGCACTGGGTGCGC |
| DRI1_P53 | 22 | TTCTTGGGCGAACACAGCCTGT |
| DRI1_P54 | 33 | TCACGCTGGATGATCAGGCCACTAAGGGCGAAG |
| DRI1_P55 | 39 | TCAAAGAGACTTCAAACGGTTCATTTAACGTTTCAACCA |

TABLE 3-continued

DRI example sequences
DRI1_NF1 is the input molecule (DRI). DRI1_T1
through DRI1_T11 correspond to V1 through V11.
DRI1_P1 through DRI1_P69 are the oligos used
by the protocol.

| Name | Length | Sequence |
|---|---|---|
| DRI1_P56 | 44 | GAAACGTTAAATGAACCGTTTGAAGTCTCTTTGAAGGACGGCGC |
| DRI1_O57 | 48 | AAAGATACCATTGCGCTGGTGGTTGAAACGTTAAATGAACCGTTTGAA |
| DRI1_P58 | 40 | TCAAAGAGACTTCAAACGGGTTATTTAACGTTTCAACCAC |
| DRI1_P59 | 45 | TGAAACGTTAAATAACCCGTTTGAAGTCTCTTTGAAGGACGGCGC |
| DRI1_O60 | 48 | AAAGATACCATTGCGCTGGTGGTTGAAACGTTAAATAACCCGTTTGAA |
| DRI1_P61 | 25 | CCTCCCCCCATTCCCGGGCCGCGCT |
| DRI1_P62 | 32 | GGCCCGGGAATGGGGGAGGGATTTCAACAGG |
| DRI1_P63 | 15 | TTCCCGGGCCGCGCT |
| DRI1_P64 | 22 | TGGGGGGAGGGATTTCAACAGG |
| DRI1_P65 | 25 | TGGGGGGAGGGATTTCAACAGGCAG |
| DRI1_P66 | 38 | TCAAAGAGACTTCAAACGGGTTATTTAACGTGCTAACC |
| DRI1_P67 | 43 | GCACGTTAAATAACCCGTTTGAAGTCTCTTTGAAGGACGGCGC |
| DRI1_O68 | 48 | AAAGATACCATTGCGCTGGTGGTTAGCACGTTAAATAACCCGTTTGAA |
| DRI1_P69 | 32 | CCATTTCATCTTCTTGGGCGAACACAGCCTGT |
| DRI1_NF1 | 813 | AAAGATACCATTGCGCTGGTGGTTAGCACGTTAAATAACCCGTTTTTCGTCTCTTTGAAGGACGGCGCCCAGAAAGAAGCAGATAAACTTGGTTATAATCTCGTAGTGCTGGACAGTCAAAACAATCCAGCTAAGGAGCTGGCGAACGTTCAGGATTTAACTGTCCGTGGGACAAAAATCTTGCTTATAAATCCTACCGACTCAGATGCCGTAGGAAACGCAGTGAAAATGGCTAATCAAGCGAACATTCCCGTTATCACGCTGGATCGCAGGCCACTAAGGGCGAAGTCGTGTCCCATATTGCATCGGACAATGTACTCGGTGGGAAAATCGCTGGAGATTACATAGCGAAAAAGGCCGGCGAGGGTGCAAAAGTTATTGAACTGCAGGGCATCGCTGGTACAAGCGCGGCCCGGAAAGAGGGGAGGGATTTCAACAGGCAGTGGCGGCTCACAAATTCAACGTCTTAGCCTCTCAACCGGCAGACGATGATCGAATTAAGGGCCTGAATGTTATGCAGAACTTGCTTACCGCGCATCCAGACGTACAGGCTGTGTTCGCCCAAAATGATGAAATGGCACTGGGTGCGCTCCGTGCTTTACAGACGGCCGGCAAAAGTGATGTCATGGTTGTGGGTTTTGACGGGACCCCTGATGAGAGAAAGCAGTAAACGACGGCAAGCTGGCGGCCACTATAGCACAATTGCCGGATCAGATCGGTGCGAAAGGGGTCGAAACAGCTGATAAAGTTCTTAAGGGCGAAAAAGTGCAGGCCAAATATCCCGTAGACCTGAAGTTAGTTGTGAAACAA |
| DRI1_T1 | 813 | AAAGATACCATTGCGCTGGTGGTTGAAACGTTAAATGAACCGTTTGAAGTCTCTTTGAAGGACGGCGCCCAGAAAGAAGCAGATAAACTTGGTTATAATCTCGTAGTGCTGGACAGTCAAAACAATCCAGCTAAGGAGCTGGCGAACGTTCAGGATTTAACTGTCCGTGGGACAAAAATCTTGCTTATAGATCCTACCGACTCAGATGCCGTAGGAAACGCAGTGAAAATGGCTAATCAAGCGAACATTCCCGTTATCACGCTGGATGATCAGGCCACTAAGGGCGAAGTCGTGTCCCATATTGCAGAAGACAATGTACTCGGTGGGAAAATCGCTGGAGATTACATAGCGAAAAAGGCCGGCGAGGGTGCAAAAGTTATTGAACTGCAGGGCATCGCTGGTACAAGCGATGCCCGGGAATGGGGGGAGGGATTTCAACAGGCAGTGGCGGCTCACAAATTCAACGTCTTAGCCTCTCAACCGGCAGACGATGATCGAATTAAGGGCCTGAATGTTATGCAGAACTTGCTTACCGCGCATCCAGACGTACAGGCTGTGTTCGCCCAAGAAGATGAAATGGCACTGGGTGCGCTCCGTGCTTTACAGACGGCCGGCAAAAGTGATGTCATGGTTGTGGGTTTTGACGGGACCCCTGATGAGAGAAAGCAGTAAACGACGGCAAGCTGGCGGCCACTATAGCAGAATTGCCGGATCAGATCGGTGCGAAAGGGGTCGAAACAGCTGATAAAGTTCTTAAGGGCGAAAAAGTGCAGGCCAAATATCCCGTAGACCTGAAGTTAGTTGTGAAACAA |
| DRI1_T2 | 813 | AAAGATACCATTGCGCTGGTGGTTGAAACGTTAAATGAACCGTGGGAAGTCTCTTTGAAGGACGGCGCCCAGAAAGAAGCAGATAAACTTGGTTATAATCTCGTAGTGCTGGACAGTCAAAACAATCCAGCTAAGGAGCTGGCGAACGTTCAGGATTTAACTGTCCGTGGGACAAAAATCTTGCTTATAGATCCTACCGACTCAGATGCCGTAGGAAACGCAGTGAAAATGGCTAATCAAGCGAACATTCCCGTTATCACGCTGGATGATCAGGCCACTAAGGGCGAAGTCGTGTCCCATATTGCATCGGACAATGTACTCGGTGGGAAAATCGCTGGAGATTACATAGCGAAAAAGGCCGGCGAGGGTGCAAAAGTTATTGAACTGCAGGGCATCGCTGGTACAAGCGATGCCCGGGAATGGGGGGAGGGATTTCAACAGGCAGTGGCGGCTCACAAATTCAACGTCTTAGCCTCTCAACCGGCAGACGATGATCGAATTAAGGGCCTGAATGTTATGCAGAACTTGCTTACCGCGCATCCAGACGTACAGGCTGTGTTCGCCCAAGAAGATGAAATGGCACTGGGTGCGCTCCGTGCTTTACAGACGGCCGGCAAAAGTGATGTCATGGTTGTGGGTTTTGACGGGACCCCTGATGAGAGAAAGCAGTAAACGACGGCAAGCTGGCGGCCACTATAGCAGAATTGCCGGATCAGATCGGTGCGAAAGGGGTCGAAACAGCTGATAAAGTTCTTAAGGGCGAAAAAGTGCAGGCCAAATATCCCGTAGACCTGAAGTTAGTTGTGAAACAA |
| DRI1_T3 | 813 | AAAGATACCATTGCGCTGGTGGTTGAAACGTTAAATGAACCGTGGGAAGTCTCTTTGAAGGACGGCGCCCAGAAAGAAGCAGATAAACTTGGTTATAATCTCGTAGTGCTGGACAGTCAAAACAATCCAGCTAAGGAGCTGGCGAACGTTCAGGATTTAACTGTCCGTGGGACAAAAATCTTGCTTATAAATCCTACCGACTCAGATGCCGTAGGAAACGCAGTGAAAATGGCTAATCAAGCGAACATTCCCGTTATCACGCTGGATGATCAGGCCACTAAGGGCGAAGTCGTGTCCCATATTGCATCGGACAATGTACTCGGTGGGAAAATCGCTGGAGATTACATAGCGAAAAAGGCCGGCGAGGGTGCAAAAGTTATTGAACTGCAGGGCATCGCTGGTACAAGCGATGCCCGGGAATGGGGGAGGGATTTCAACAGGCAGTGGCGGCTCACAAATTCAACGTCTTAGCCTCTCAACCGGCAGACGATGATCGAATTAAGGGCCTGAATGTTATGCAGAACTTGCTTACCGCGCATCCAGACGTACAGGCTGTGTTCGCCCAAGAAGATGAAATGGCACTGGGTGCGCTCCGTGCTTTACAGACGGCCGGCAAAAGTGATGTCATGGTT |

TABLE 3-continued

DRI example sequences
DRI1_NF1 is the input molecule (DRI). DRI1_T1
through DRI1_T11 correspond to V1 through V11.
DRI1_P1 through DRI1_P69 are the oligos used
by the protocol.

| Name | Length | Sequence |
|---|---|---|
| | | TTGACGGGACCCCTGATGGAGAGAAAGCACAG |
| | | GTAAACGACGGCAAGCTGGCGGCCACTATAGA |
| | | ATTGCCGGATCAGATCGGTGCGAAAGGGGTGG |
| | | TCGAAACAGCTGATAAAGTTCTTAAGGGCGAA |
| | | AAAGTGCAGGCCAAATATCCCGTAGACCTGAA |
| | | GTTAGTTGTGAAACAA |
| DRI1_T4 | 813 | AAAGATACCATTGCGCTGGTGGTTGAAACGTT |
| | | AAATGAACCGTGGGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGATGCCCG |
| | | GGAATGGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T5 | 813 | AAAGATACCATTGCGCTGGTGGTTGAAACGTT |
| | | AAATGAACCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGATGCCCG |
| | | GGAATGGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T6 | 813 | AAAGATACCATTGCGCTGGTGGTTGAAACGTT |
| | | AAATAACCCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGATGCCCG |
| | | GGAATGGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T7 | 813 | AAAGATACCATTGCGCTGGTGGTTGAAACGTT |
| | | AAATAACCCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGCGGCCCG |
| | | GGAATGGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T8 | 813 | AAAGATACCATTGCGCTGGTGGTTAGCACGTT |
| | | AAATAACCCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGCGGCCCG |
| | | GGAATGGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AACAGCTGATAAAGTTCTTAAGGGCGAAAAAG |
| | | TGCAGGCCAAATATCCCGTAGACCTGAAGTTA |
| | | GTTGTGAAACAA |
| DRI1_T9 | 813 | AAAGATACCATTGCGCTGGTGGTTAGCACGTT |
| | | AAATAACCCGTTTGAAGTCTCTTTGAAGGACG |

TABLE 3-continued

DRI example sequences
DRI1_NF1 is the input molecule (DRI). DRI1_T1 through DRI1_T11 correspond to V1 through V11. DRI1_P1 through DRI1_P69 are the oligos used by the protocol.

| Name | Length | Sequence |
|---|---|---|
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGCGGCCCG |
| | | GGAAAGAGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAGAAGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T10 | 813 | AAAGATACCATTGCGCTGGTGGTTAGCACGTT |
| | | AAATAACCCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGCGGCCCG |
| | | GGAAAGAGGGGAGGGATTTCAACAGGCAGTGG |
| | | CGGCTCACAAATTCAACGTCTTAGCCTCTCAA |
| | | CCGGCAGACGATGATCGAATTAAGGGCCTGAA |
| | | TGTTATGCAGAACTTGCTTACCGCGCATCCAG |
| | | ACGTACAGGCTGTGTTCGCCCAAAATGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |
| DRI1_T11 | 813 | AAAGATACCATTGCGCTGGTGGTTAGCACGTT |
| | | AAATAACCCGTTTGAAGTCTCTTTGAAGGACG |
| | | GCGCCCAGAAAGAAGCAGATAAACTTGGTTAT |
| | | AATCTCGTAGTGCTGGACAGTCAAAACAATCC |
| | | AGCTAAGGAGCTGGCGAACGTTCAGGATTTAA |
| | | CTGTCCGTGGGACAAAAATCTTGCTTATAAAT |
| | | CCTACCGACTCAGATGCCGTAGGAAACGCAGT |
| | | GAAAATGGCTAATCAAGCGAACATTCCCGTTA |
| | | TCACGCTGGATGATCAGGCCACTAAGGGCGAA |
| | | GTCGTGTCCCATATTGCATCGGACAATGTACT |
| | | CGGTGGGAAAATCGCTGGAGATTACATAGCGA |
| | | AAAAGGCCGGCGAGGGTGCAAAAGTTATTGAA |
| | | CTGCAGGGCATCGCTGGTACAAGCGCGGCCCG |
| | | GGAAAGAGGGGAGGGATTTCAACAGGCAGTGG |
| | | CGGCTCACAAATTCAACGTCTTAGCCTCTCAA |
| | | CCGGCAGACTTTGATCGAATTAAGGGCCTGAA |
| | | TGTTATGCAGAACTTGCTTACCGCGCATCCAG |
| | | ACGTACAGGCTGTGTTCGCCCAAAATGATGAA |
| | | ATGGCACTGGGTGCGCTCCGTGCTTTACAGAC |
| | | GGCCGGCAAAAGTGATGTCATGGTTGTGGGTT |
| | | TTGACGGGACCCCTGATGGAGAGAAAGCAGTA |
| | | AACGACGGCAAGCTGGCGGCCACTATAGCACA |
| | | ATTGCCGGATCAGATCGGTGCGAAAGGGGTCG |
| | | AAACAGCTGATAAAGTTCTTAAGGGCGAAAAA |
| | | GTGCAGGCCAAATATCCCGTAGACCTGAAGTT |
| | | AGTTGTGAAACAA |

EXAMPLE 4

A Protein-Chimera Library

In another example, two protein enzymes share extensive sequence homology, yet differ in their substrate specificity. In order to determine which part of the enzymes determines the specificity protein, chimeras may optionally be created, combining different parts from the two proteins. As in any type of search, the speed at which the right position is found is dependent on the amount of variants constructed and tested, given that an efficient assay for measure substrate specificity is available.

Figure 8A:
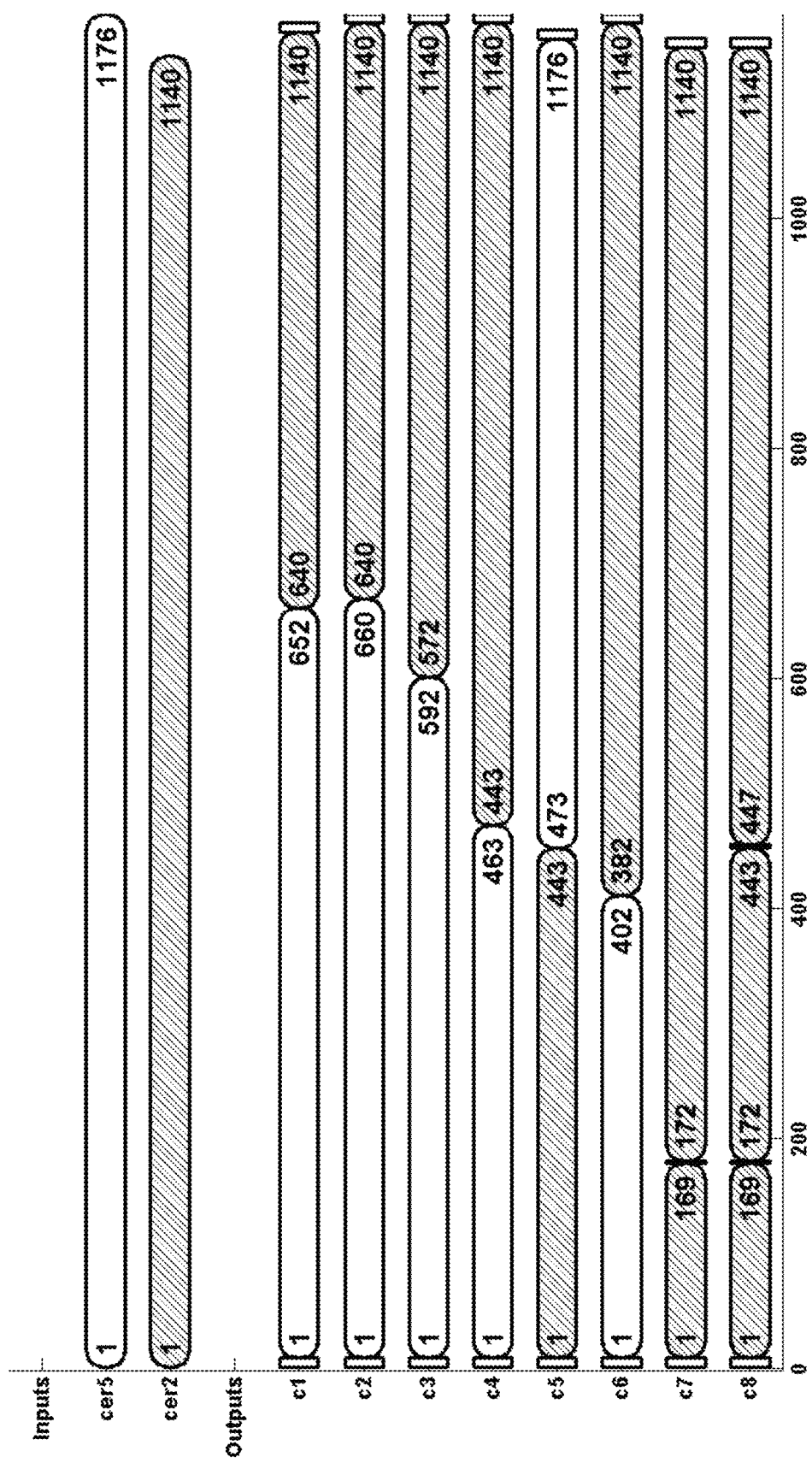
FIG. 8A provides schematic diagrams of the input and output DNA molecules provided for by an optional editing protocol as depicted in Example 4 as non-limiting examples only.
Figure 8B:
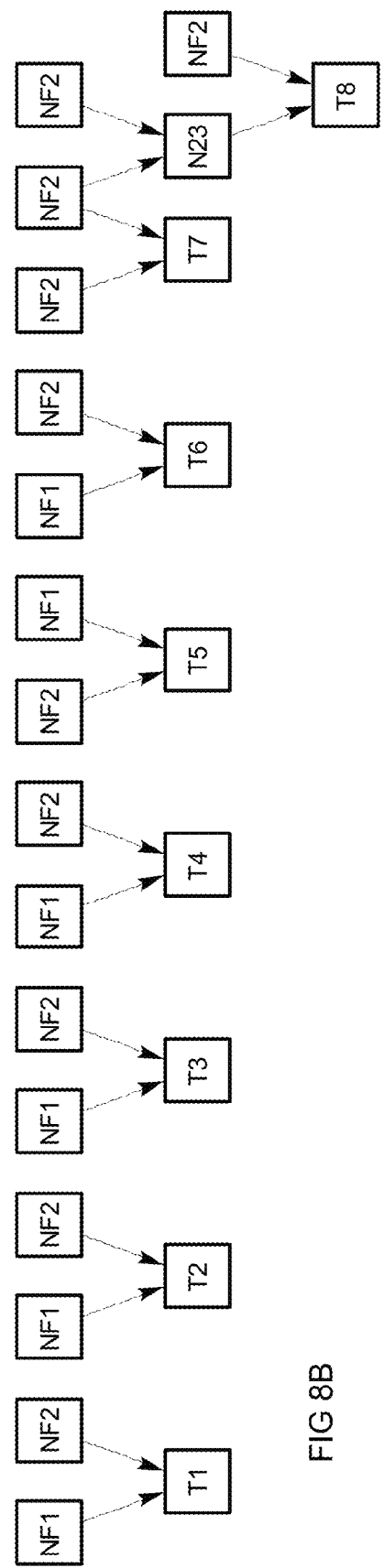
FIG. 8B provides a schematic diagram of an exemplary editing protocol map in the form of a binary tree according to some illustrative embodiments of the system and method of the present invention, relating to the input and output sequences of FIG. 8A.

For this Example, two genes, CER5 and CER2, were used, recombining them in six different ways and making two mutants in one of them. For details see FIGS. 8A and 8B. Briefly, FIG. 8A shows desired recombinations of the two input genes, including two mutants on one of the input genes. In addition, restriction sites were added as flanking regions to each target to facilitate downstream application of the constructs. FIG. 8B shows the construction plan. Note that adding flanking regions as well as making small mutations within sequence do not require additional Y operation and can be incorporated into the primers.

In this example, no error correction step was required. Out of 8 constructs, only one contained an error and a second clone tested was error free.

This example demonstrates the ability to reuse existing DNA to avoid costly error correction as the result is often error free. It thus demonstrates the power of the system to achieve editing of DNA completely in vitro and to combine large pieces of existing DNA.

Materials and Methods

The complete set of sequences is shown in Table 4 below. The sequences were created according to the methods depicted in FIG. 8B and the methods described with regard to Example 1; upon sequencing, no errors were found (data not shown).

TABLE 4

CER example sequences
CER_NF1/NF2 are the input molecules (CER5/CER2 respectively). CER_T1 through CER_T8 are the eight target molecules (referred to as C1-C8 in the figures). CER_P1 through CER_P25 are the oligos used by the protocol.

| | Size | Sequence |
|---|---|---|
| CER_P1 | 29 | CCGAATTCGCGACAGCAGCGCAGGGACCC |
| CER_P2 | 35 | TGGTGGCCACGTGATGCACAAACATGATCAGGAAG |

TABLE 4 -continued

CER example sequences
CER_NF1/NF2 are the input molecules
(CER5/CER2 respectively). CER_T1 through
CER_T8 are the eight target molecules
(referred to as C1-C8 in the figures).
CER_P1 through CER_P25 are the oligos
used by the protocol.

| | Size | Sequence |
|---|---|---|
| CER_P3 | 32 | TGTTTGTGCATCACGTGGCCACCATCATTCTC |
| CER_P4 | 30 | CCCTCGAGTCAGTCATTCTTACGATGGTTG |
| CER_P5 | 35 | GTTCCTTGAAGTCCTTTCTTTTAATGTCTGTAAAC |
| CER_P6 | 48 | CAGTTTACAGACATTAAAAGAAAGGACTTCAAGGAACAGATCATCCAC |
| CER_P7 | 34 | AAGTTCAATCATATAATAGTGATAAAGCCCACTT |
| CER_P8 | 52 | TTCAAGTGGGCTTTATCACTATTATATGATTGAACTTTCCTTCTACTGGTCC |
| CER_P9 | 31 | GCAATCAGATAAAATGTGAATCTCCACATGC |
| CER_P10 | 46 | GCATGTGGAGATTCACATTTTATCTGATTGCCTTCATTGCCGGCAT |
| CER_P11 | 38 | CCCTCGAGTTACTCTTCAGCCCAGTAGCTGCCTCCCAT |
| CER_P12 | 37 | ATATACATAAGTAAAATGTGAATCTCCAGCTGGCTTC |
| CER_P13 | 52 | AGCCAGCTGGAGATTCACATTTTACTTATGTATATTCTGCTATGGAATTAGA |
| CER_P14 | 30 | CCGAATTCCTCCAGACCTTGTATGATTACT |
| CER_P15 | 24 | CGGTCCTGGTTCCTCCGATGGCGA |
| CER_P16 | 32 | CGCCATCGGAGGAACCAGGACCGGCCCAGTCT |
| CER_P17 | 22 | CCGAATTCCTCCAGACCTTGTA |
| CER_P18 | 53 | GATACTTCTTTGAGCGATACGTGGCTACACCACTGGCTGCCCTCTTGAACATA |
| CER_P19 | 33 | CCCTCGAGTCAGTCATTCTTACGATGGTTGTTA |
| CER_P20 | 32 | AGCCACGTATCGCTCAAAGAAGTATCGAACGA |
| CER_P21 | 26 | CCACAATGACTCTCATGCCGGCAATG |
| CER_P22 | 38 | TTGCCGGCATGAGAGTCATTGTGGATAAACCCTGGTTC |
| CER_P23 | 43 | GATACTTCTTTGAGCGATACGTGGCTACACCACTGGCTGCCCT |
| CER_P24 | 19 | TCTCATGCCGGCAATGAAG |
| CER_P25 | 33 | TAGCCACGTATCGCTCAAAGAAGTATCGAACGA |
| CER_NF1 | 1176 | GCGACAGCAGCGCAGGGACCCCTAAGCTTGCTGTGGGGCTGGCTGTGGAGCGAGCGCTTCTGGCTACCCGAGAACGTGAGCTGGGCTGATCTGGAGGGGCCGGCCGACGGCTACGGTTACCCCGCGGCCGGCCACATCCTCTCGGTGTTCCCGCTGGCGGCGGGCATCTTCTTCGTGAGGCTGCTCTTCGAGCGATTTATTGCCAAACCCTGTGCACTCTGTATTGGCATCGAGGACAGTGGTCCTTATCAGGCCCAACCCATCCTTGAAAAGGTGTTCATACTCTATTACCAAGTATCCTGATAAGAAAGGCTGGAGGGCCTGTCAAGCAGCTGGATTGGAATGTCCGAAAAATCCAATGCTGGTTTCGCCATCGGAGGAATCAGGACAAGCCCCCAACCTACTAAATTCTGTGAAAGCATGTGGAGATTCACATTTTATTTATGTATATTCTGCTATGGAATTAGATTTCTCTGGTCGTCACCTTGGTTCTGGGACATCCGACAGTGCTGGCATAACTATCCATTTCAGCCTCTTTCAAGTGGGCTTTATCACTATTATATCATGGAATTGGCCTTCTATT |
| | | GGTCCCTTATGTTTTCTCAGTTTACAGACATTAAAAGAAAGGACTTCCTGATCATGTTTGTGCATCACTTGGTCACCATTGGGCTTATCTCCTTCTCCTACATCAACAATATGGTTCGAGTGGGAACTCTGATCATGTGTCTACATGATGTCTCAGACTTCTTGCTGGAGGCAGCCAAACTGGCCAATTATGCCAAGTATCAGCGGCTCTGTGACACCCTTTTTGTGATCTTCAGTGCTGTTTTTATGGTTACACGACTAGGAATCTATCCATTCTGGATTCTGAACACGACCCTCTTTGAGAGTTGGGAGATAATCGGGCCTTATGCTTCATGGTGGCTCCTCAATGGCCTGCTGCTGACCCTACAGCTTCTGCATGCTCATCTGGTCCTACCTAATTGCACGGATTGCTTTGAAAGCCTTGATCAGGGGAAAGGTATCGAAGGATGATCGCAGTGATGTGGAGAGCAGCTCAGAGGAAGAAGATGTGACCACCTGCACAAAAAGTCCCTGTGACAGTAGCTCCAGCAATGGTGCCAATCGGGTGAATGGTCACATGGGAGGCAGCTACTGGGCTGAAGAGTAA |
| CER_NF2 | 1140 | CTCCAGACCTTGTATGATTACTTCTGGTGGGAACGTCTGTGGCTGCCTGTGAACTTGACCTGGGCCGATCTAGAAGACCGAGATGGACGTGTCTACGCCAAAGCCTCAGATCTCTATATCACGCTGCCCCTGGCCTTGCTCTTCCTCATCGTTCGATACTTCTTTGAGCTGTACGTGGCTACACCACTGGCTGCCCTCTTGAACATAAAGGAGAAACTCGGCTGCGGGCACCTCCCAACGCCACCTTGGAACATTTCTACCTGACCAGTGGCAAGCAGCCCAAGCAGGTGGAAGTAGAGCTTTTGTCCCGGCAGAGCGGGCTCTCTGGCCGCCAGGTAGAGCGTTGGTTCCGTCGCCGGCCGCAACCAGGACCGGCCCAGTCTCCTCAAGAAGTTCCGAGAAGCCAGCTGGAGATTCACATTTTACTTGATTGCCTTCATTGCCGGCATGGCCGTCATTGTGGATAAACCCTGGTTCTATGACATGAAGAAAGTTTGGGAGGGATATCCCATACAGAGCACTATCCCTTCCCAGTATTGGTACTACATGATTGAACTTTCCTTCTACTGGTCCCTGCTCTTCAGCATTGCCTCTGATGTCAAGCGAAAGGATTTCAAGGAACAGATCATCCACCATGTGGCCACCATCATTCTCATCAGCTTTTCCTGGTTTGCCAATTACATCCGAGCTGGGACTCTAATCATGGCTCTGCATGACTCTTCCGATTACCTGCTGGAGTCAGCCAAGATGTTTAACTACGCGGGATGGAAGAACACCTGCAACAACATCTTCATCGTCTTCGCCATTGTTTTATCATCACCCGACTGGTCATCCTGCCCTTCTGGATCCTGCATTGCACCCTGGTGTACCCACTGGAGCTCTATCCTGCCTTCTTTGGCTATTACTTCTTCAATTCCATGATGGGAGTTCTACAGCTGCTGCATATCTTCTGGGCCTACCTCATTTTGCGCATGGCCCACAAGTTCATAACTGGAAAGCTGGTAGAAGATGAACGCAGTGACCGGGAAGAAACAGAGAGCTCAGAGGGGGAGGAGGCTGCAGCTGGGGGAGGAGCAAAGAGCCGGCCCCTAGCCAATGGCCACCCCATCCTCAATAACAACCATCGTAAGAATGACTGA |
| CER_T1 | 1180 | CCGAATTCGCGACAGCAGCGCAGGGACCCCTAAGCTTGCTGTGGGGCTGGCTGTGGAGCGAGCGCTTCTGGCTACCCGAGAACGTGAGCTGGGCTGATCTGGAGGGGCCGGCCGACGGCTACGGTTACCCCCGCGGCCGGCCACATCCTCTCGGTGTTCCCGCTGGCGGCGGGCATCTTCTTCGTGAGGCTGCTCTTCGAGCGATTATTGCCAAACCCTGTGCACTCTGTATTGGCATCGAGGACAGTGGTCCTTATCAGGCCCAACCCATCCATCCTTGAAAAGGTGTTCATATCTATTACCAAGTATCCTGATAAGAAAGGCTGGAGGCCTGTCAAAGCAGCTGGATTGGAATGTCCGAAAAATCCAATGCTGGTTTCGCCATCGGAGGAATCAGGACAAGCCCCCAACCTACTAAATTCTGTGAAAGCATGTGGAGATTCACATTTTATTTATGTATATTCTGCTATGGAATTAGATTTCTCTGGTCGTCACCTTGGTTCTGGGACATCCGACAGTGCTGGCATAACTATCCATTTCAGCCTCTTTCAAGTGGGCTTTATCACTATTATATCATGGAATTGGCCTTCTATTGGTCCCTTATGTTTTCTCAGTTTACAGACATTAAAAGAAAGGACTTCCTGATCATGTTTGTGCATCACGTGGCCACCATCATTCTCATCAGCTTTTCCTGGTTTGCCAATTACATCCGAGCTGGGACTCTAATCATGGCTCTGCATGACTCTTCCGATTACCTGCTGGAGTCAGCCA |

TABLE 4 -continued

CER example sequences
CER_NF1/NF2 are the input molecules
(CER5/CER2 respectively). CER_T1 through
CER_T8 are the eight target molecules
(referred to as C1-C8 in the figures).
CER_P1 through CER_P25 are the oligos
used by the protocol.

| | Size | Sequence |
|---|---|---|
| | | AGATGTTTAACTACGCGGGATGGAAGAACACCTGCAA |
| | | CAACATCTTCATCGTCTTCGCCATTGTTTTTATCATC |
| | | ACCCGACTGGTCATCCTGCCCTTCTGGATCCTGCATT |
| | | GCACCCTGGTGTACCCACTGGAGCTCTATCCTGCCTT |
| | | CTTTGGCTATTACTTCTTCAATTCCATGATGGGAGTT |
| | | CTACAGCTGCTGCATATCTTCTGGGCCTACCTCATTT |
| | | TGCGCATGGCCCACAAGTTCATAACTGGAAAGCTGGT |
| | | AGAAGATGAACGCAGTGACCGGGAAGAAACAGAGAGC |
| | | TCAGAGGGGGAGGAGGCTGCAGCTGGGGAGGAGCAA |
| | | AGAGCCGGCCCCTAGCCAATGGCCACCCCATCCTCAA |
| | | TAACAACCATCGTAAGAATGACTGACTCGAGGG |
| CER_T2 | 1180 | CCGAATTCGCGACAGCAGCGCAGGGACCCCTAAGCTT |
| | | GCTGTGGGGCTGGCTGTGGAGCGAGCGCTTCTGGCTA |
| | | CCCGAGAACGTGAGCTGGGCTGATCTGGAGGGGCCGG |
| | | CCGACGGCTACGGTTACCCCCGCGGCCGGCACATCCT |
| | | CTCGGTGTTCCCGCTGGCGGCGGGCATCTTCTTCGTG |
| | | AGGCTGCTCTTCGAGCGATTTATTGCCAAACCCTGTG |
| | | CACTCTGTATTGGCATCGAGGACAGTGGTCCTTATCA |
| | | GGCCCAACCCAATGCCATCCTTGAAAAGGTGTTCATA |
| | | TCTATTACCAAGTATCCTGATAAGAAAAGGCTGGAGG |
| | | GCCTGTCAAAGCAGCTGGATTGGAATGTCCGAAAAAT |
| | | CCAATGCTGGTTTCGCCATCGGAGGAATCAGGACAAG |
| | | CCCCCAACGCTTACTAAATTCTGTGAAAGCATGTGGA |
| | | GATTCACATTTTATTTATGTATATTCTGCTATGGAAT |
| | | TAGATTTCTCTGGTCGTCACCTTGGTTCTGGGACATC |
| | | CGACAGTGCTGGCATAACTATCCATTTCAGCCTCTTT |
| | | CAAGTGGGCTTTATCACTATTATATCATGGAATTGGC |
| | | CTTCTATTGGTCCCTGCTCTTCAGCATTGCCTCTGAT |
| | | GTCAAGCGAAAGGATTTCAAGGAACAGATCATCCACC |
| | | ATGTGGCCACCATCATTCTCATCAGCTTTTCCTGGTT |
| | | TGCCAATTACATCCGAGCTGGGACTCTAATCATGGCT |
| | | CTGCATGACTCTTCCGATTACCTGCTGGAGTCAGCCA |
| | | AGATGTTTAACTACGCGGGATGGAAGAACACCTGCAA |
| | | CAACATCTTCATCGTCTTCGCCATTGTTTTTATCATC |
| | | ACCCGACTGGTCATCCTGCCCTTCTGGATCCTGCATT |
| | | GCACCCTGGTGTACCCACTGGAGCTCTATCCTGCCTT |
| | | CTTTGGCTATTACTTCTTCAATTCCATGATGGGAGTT |
| | | CTACAGCTGCTGCATATCTTCTGGGCCTACCTCATTT |
| | | TGCGCATGGCCCACAAGTTCATAACTGGAAAGCTGGT |
| | | AGAAGATGAACGCAGTGACCGGGAAGAAACAGAGAGC |
| | | TCAGAGGGGGAGGAGGCTGCAGCTGGGGAGGAGCAA |
| | | AGAGCCGGCCCCTAGCCAATGGCCACCCCATCCTCAA |
| | | TAACAACCATCGTAAGAATGACTGACTCGAGGG |
| CER_T3 | 1180 | CCGAATTCGCGACAGCAGCGCAGGGACCCCTAAGCTT |
| | | GCTGTGGGGCTGGCTGTGGAGCGAGCGCTTCTGGCTA |
| | | CCCGAGAACGTGAGCTGGGCTGATCTGGAGGGGCCGG |
| | | CCGACGGCTACGGTTACCCCCGCGGCCGGCACATCCT |
| | | CTCGGTGTTCCCGCTGGCGGCGGGCATCTTCTTCGTG |
| | | AGGCTGCTCTTCGAGCGATTTATTGCCAAACCCTGTG |
| | | CACTCTGTATTGGCATCGAGGACAGTGGTCCTTATCA |
| | | GGCCCAACCCAATGCCATCCTTGAAAAGGTGTTCATA |
| | | TCTATTACCAAGTATCCTGATAAGAAAAGGCTGGAGG |
| | | GCCTGTCAAAGCAGCTGGATTGGAATGTCCGAAAAAT |
| | | CCAATGCTGGTTTCGCCATCGGAGGAATCAGGACAAG |
| | | CCCCCAACGCTTACTAAATTCTGTGAAAGCATGTGGA |
| | | GATTCACATTTTATTTATGTATATTCTGCTATGGAAT |
| | | TAGATTTCTCTGGTCGTCACCTTGGTTCTGGGACATC |
| | | CGACAGTGCTGGCATAACTATCCATTTCAGCCTCTTT |
| | | CAAGTGGGCTTTATCACTATTATATCATGGAATTGGC |
| | | CTTCTACTGGTCCCTGCTCTTCAGCATTGCCTCTGAT |
| | | GTCAAGCGAAAGGATTTCAAGGAACAGATCATCCACC |
| | | ATGTGGCCACCATCATTCTCATCAGCTTTTCCTGGTT |
| | | TGCCAATTACATCCGAGCTGGGACTCTAATCATGGCT |
| | | CTGCATGACTCTTCCGATTACCTGCTGGAGTCAGCCA |
| | | AGATGTTTAACTACGCGGGATGGAAGAACACCTGCAA |
| | | CAACATCTTCATCGTCTTCGCCATTGTTTTTATCATC |
| | | ACCCGACTGGTCATCCTGCCCTTCTGGATCCTGCATT |
| | | GCACCCTGGTGTACCCACTGGAGCTCTATCCTGCCTT |
| | | CTTTGGCTATTACTTCTTCAATTCCATGATGGGAGTT |
| | | CTACAGCTGCTGCATATCTTCTGGGCCTACCTCATTT |
| | | TGCGCATGGCCCACAAGTTCATAACTGGAAAGCTGGT |
| | | AGAAGATGAACGCAGTGACCGGGAAGAAACAGAGAGC |
| | | TCAGAGGGGGAGGAGGCTGCAGCTGGGGAGGAGCAA |
| | | AGAGCCGGCCCCTAGCCAATGGCCACCCCATCCTCAA |
| | | TAACAACCATCGTAAGAATGACTGACTCGAGGG |
| CER_T4 | 1180 | CCGAATTCGCGACAGCAGCGCAGGGACCCCTAAGCTT |
| | | GCTGTGGGGCTGGCTGTGGAGCGAGCGCTTCTGGCTA |
| | | CCCGAGAACGTGAGCTGGGCTGATCTGGAGGGGCCGG |
| | | CCGACGGCTACGGTTACCCCCGCGGCCGGCACATCCT |
| | | CTCGGTGTTCCCGCTGGCGGCGGGCATCTTCTTCGTG |
| | | AGGCTGCTCTTCGAGCGATTTATTGCCAAACCCTGTG |
| | | CACTCTGTATTGGCATCGAGGACAGTGGTCCTTATCA |
| | | GGCCCAACCCAATGCCATCCTTGAAAAGGTGTTCATA |
| | | TCTATTACCAAGTATCCTGATAAGAAAAGGCTGGAGG |
| | | GCCTGTCAAAGCAGCTGGATTGGAATGTCCGAAAAAT |
| | | CCAATGCTGGTTTCGCCATCGGAGGAATCAGGACAAG |
| | | CCCCCAACGCTTACTAAATTCTGTGAAAGCATGTGGA |
| | | GATTCACATTTTATCTGATTGCCTTCATTGCCGGCAT |
| | | GGCCGTCATTGTGGATAAACCCTGGTTCTATGACATG |
| | | AAGAAAGTTTGGGAGGGATATCCCATCAGAGGCACTA |
| | | TCCCTTCCCAGTATTGGTACTACATGATTGAACTTTC |
| | | CTTCTACTGGTCCCTGCTCTTCAGCATTGCCTCTGAT |
| | | GTCAAGCGAAAGGATTTCAAGGAACAGATCATCCACC |
| | | ATGTGGCCACCATCATTCTCATCAGCTTTTCCTGGTT |
| | | TGCCAATTACATCCGAGCTGGGACTCTAATCATGGCT |
| | | CTGCATGACTCTTCCGATTACCTGCTGGAGTCAGCCA |
| | | AGATGTTTAACTACGCGGGATGGAAGAACACCTGCAA |
| | | CAACATCTTCATCGTCTTCGCCATTGTTTTTATCATC |
| | | ACCCGACTGGTCATCCTGCCCTTCTGGATCCTGCATT |
| | | GCACCCTGGTGTACCCACTGGAGCTCTATCCTGCCTT |
| | | CTTTGGCTATTACTTCTTCAATTCCATGATGGGAGTT |
| | | CTACAGCTGCTGCATATCTTCTGGGCCTACCTCATTT |
| | | TGCGCATGGCCCACAAGTTCATAACTGGAAAGCTGGT |
| | | AGAAGATGAACGCAGTGACCGGGAAGAAACAGAGAGC |
| | | TCAGAGGGGGAGGAGGCTGCAGCTGGGGAGGAGCAA |
| | | AGAGCCGGCCCCTAGCCAATGGCCACCCCATCCTCAA |
| | | TAACAACCATCGTAAGAATGACTGACTCGAGGG |
| CER_T5 | 1168 | CCGAATTCCTCCAGACCTTGTATGATTACTTCTGGTG |
| | | GGAACGTCTGTGGCTGCCTGTGAACTTGACCTGGGCC |
| | | GATCTAGAAGACCGAGATGGACGTGTCTACGCCAAG |
| | | CCTCAGATCTCTATATCACGCTGCCCCTGGCCTTGCT |
| | | CTTCCTCATCGTTCGATACTTCTTTGAGCTGTACGTG |
| | | GCTACACCACTGGCTGCCCTCTTGAACATAAAGGAGA |
| | | AAACTCGGCTGCGGGCACCTCCCAACGCCACCTTGGA |
| | | ACATTTCTACCTGACCAGTGGCAAGCAGCCCAAGCAG |
| | | GTGGAAGTAGAGCTTTTGTCCCGGCAGAGCGGGCTCT |
| | | CTGGCCGCCAGGTAGAGCGTTGGTTCCGTCGCCGCCG |
| | | CAACCAGGACCGGCCAGTCTCCTCAAGAAGTTCCGA |
| | | GAAGCCAGCTGGAGATTCACATTTTACTTATGTATAT |
| | | TCTGCTATGGAATTAGATTTCTCTGGTCGTCACCTTG |
| | | GTTCTGGGACATCCGACAGTGCTGGCATAACTATCCA |
| | | TTTCAGCCTCTTTCAAGTGGGCTTTATCACTATTATA |
| | | TCATGGAATTGGCCTTCTATTGGTCCCTTATGTTTTC |
| | | TCAGTTTACAGACATTAAAAGAAAGGACTTCCTGATC |
| | | ATGTTTGTGCATCACTTGGTCACCATTGGGCTTATCT |
| | | CCTTCTCCTACATCAACAATATGGTTCGAGTGGGAAC |
| | | TCTGATCATGTGTCTACATGATGTCTCAGACTTCTTG |
| | | CTGGAGGCAGCCAAACTGGCCAATTATGCCAAGTATC |
| | | AGCGGCTCTGTGACACCCTTTTTGTGATCTTCAGTGC |
| | | TGTTTTTATGGTTACACGACTAGGAATCTATCCATTC |
| | | TGGATTCTGAACATTCTGTTTGAGAGTTGGAGA |
| | | TAATCGGGCCTTATGCTTCATGGTGGCTCCTCAATGG |
| | | CCTGCTGCTGACCCTACAGCTTCTGCATGTCATCTGG |
| | | TCCTACCTAATTGCACGGATTGCTTTGAAAGCCTTGA |
| | | TCAGGGGAAAGGTATCGAAGGATGATCGCAGTGATGT |
| | | GGAGAGCAGCTCAGAGGAAGAAGATGTGACCACCTGC |

TABLE 4 -continued

CER example sequences
CER_NF1/NF2 are the input molecules
(CER5/CER2 respectively). CER_T1 through
CER_T8 are the eight target molecules
(referred to as C1-C8 in the figures).
CER_P1 through CER_P25 are the oligos
used by the protocol.

| | Size | Sequence |
|---|---|---|
| | | ACAAAAAGTCCCTGTGACAGTAGCTCCAGCAATGGTG CCAATCGGGTGAATGGTCACATGGGAGGCAGCTACTG GGCTGAAGAGTAACTCGAGGG |
| CER_T6 | 1180 | CCGAATTCGCGACAGCAGCGCAGGGACCCCTAAGCTT GCTGTGGGGCTGGCTGTGGAGCGAGCGCTTCTGGCTA CCCGAGAACGTGAGCTGGGCTGATCTGGAGGGGCCGG CCGACGGCTACGGTTACCCCCGCGGCCGGCACATCCT CTCGGTGTTCCCGCTGGCGGCGGGCATCTTCTTCGTG AGGCTGCTCTTCGAGCGATTTATTGCCAAACCCTGTG CACTCTGTATTGGCATCGAGGACAGTGGTCCTTATCA GGCCCAACCCAATGCCATCCTTGAAAAGGTGTTCATA TCTATTACCAAGTATCCTGATAAGAAAAGGCTGGAGG GCCTGTCAAAGCAGCTGGATTGGAATGTCCGAAAAAT CCAATGCTGGTTTCGCCATCGGAGGAACCAGGACCGG CCCAGTCTCCTCAAGAAGTTCCGAGAAGCCAGCTGGA GATTCACATTTTACCTGATTGCCTTCATTGCCGGCAT GGCCGTCATTGTGGATAAACCCTGGTTCTATGACATG AAGAAAGTTTGGGAGGGATATCCCATACAGAGCACTA TCCCTTCCCAGTATTGGTACTACATGATTGAACTTTC CTTCTACTGGTCCCTGCTCTTCAGCATTGCCTCTGAT GTCAAGCGAAAGGATTTCAAGGAACAGATCATCCACC ATGTGGCCACCATCATTCTCATCAGCTTTTCCTGGTT TGCCAATTACATCCGAGCTGGGACTCTAATCATGGCT CTGCATGACTCTTCCGATTACCTGCTGGAGTCAGCCA AGATGTTTAACTACGCGGGATGGAAGAACACCTGCAA CAACATCTTCATCGTCTTCGCCATTGTTTTTATCATC ACCCGACTGGTCATCCTGCCCTTCTGGATCCTGCATT GCACCCTGGTGTACCCACTGGAGCTCTATCCTGCCTT CTTTGGCTATTACTTCTTCAATTCCATGATGGGAGTT CTACAGCTGCTGCATATCTTCTGGGCCTACCTCATTT TGCGCATGCCCACAAGTTCATAACTGGAAAGCTGGT AGAAGATGAACGCAGTGACCGGGAAGAAACAGAGAGC TCAGAGGGGAGGAGGCTGCAGCTGGGGGAGGAGCAA AGAGCCGGCCCCTAGCCAATGGCCACCCCATCCTCAA TAACAACCATCGTAAGAATGACTGACTCGAGGG |
| CER_T7 | 1156 | CCGAATTCCTCCAGACCTTGTATGATTACTTCTGGTG GGAACGTCTGTGGCTGCCTGTGAACTTGACCTGGGCC GATCTAGAAGACCGAGATGGACGTGTCTACGCCAAAG CCTCAGATCTCTATATCACGCTGCCCCTGGCCTTGCT CTTCCTCATCGTTCGATACTTCTTTGAGCGATACGTG GCTACACCACTGGCTGCCCTCTTGAACATAAAGGAGA AAACTCGGCTGCGGGCACCTCCCAACGCCACCTTGGA ACATTTCTACCTGACCAGTGGCAAGCAGCCCAAGCAG GTGGAAGTAGAGCTTTTGTCCCGGCAGAGCGGGCTCT CTGGCCGCCAGGTAGAGCGTTGGTTCCGTCGCCGCCG CAACCAGGACCGGCCCAGTCTCCTCAAGAAGTTCCGA GAAGCCAGCTGGAGATTCACATTTTACCTGATTGCCT TCATTGCCGGCATGGCCGTCATTGTGGATAAACCCTG GTTCTATGACATGAAGAAAGTTTGGGAGGGATATCCC ATACAGAGCACTATCCCTTCCCAGTATTGGTACTACA TGATTGAACTTTCCTTCTACTGGTCCCTGCTCTTCAG CATTGCCTCTGATGTCAAGCGAAAGGATTTCAAGGAA CAGATCATCCACCATGTGGCCACCATCATTCTCATCA GCTTTTCCTGGTTTGCCAATTACATCCGAGCTGGGAC TCTAATCATGGCTCTGCATGACTCTTCCGATTACCTG CTGGAGTCAGCCAAGATGTTTAACTACGCGGGATGGA AGAACACCTGCAACAACATCTTCATCGTCTTCGCCAT TGTTTTTATCATCACCCGACTGGTCATCCTGCCCTTC TGGATCCTGCATTGCACCCTGGTGTACCCACTGGAGC TCTATCCTGCCTTCTTTGGCTATTACTTCTTCAATTC CATGATGGGAGTTCTACAGCTGCTGCATATCTTCTGG GCCTACCTCATTTTGCGCATGCCCACAAGTTCATAA CTGGAAAGCTGGTAGAAGATGAACGCAGTGACCGGGA AGAAACAGAGAGCTCAGAGGGGAGGAGGCTGCAGCT GGGGGAGGAGCAAAGAGCCGGCCCCTAGCCAATGGCC ACCCCATCCTCAATAACAACCATCGTAAGAATGACTG ACTCGAGGG |
| CER_T8 | 1156 | CCGAATTCCTCCAGACCTTGTATGATTACTTCTGGTG GGAACGTCTGTGGCTGCCTGTGAACTTGACCTGGGCC GATCTAGAAGACCGAGATGGACGTGTCTACGCCAAAG CCTCAGATCTCTATATCACGCTGCCCCTGGCCTTGCT CTTCCTCATCGTTCGATACTTCTTTGAGCGATACGTG GCTACACCACTGGCTGCCCTCTTGAACATAAAGGAGA AAACTCGGCTGCGGGCACCTCCCAACGCCACCTTGGA ACATTTCTACCTGACCAGTGGCAAGCAGCCCAAGCAG GTGGAAGTAGAGCTTTTGTCCCGGCAGAGCGGGCTCT CTGGCCGCCAGGTAGAGCGTTGGTTCCGTCGCCGCCG CAACCAGGACCGGCCCAGTCTCCTCAAGAAGTTCCGA GAAGCCAGCTGGAGATTCACATTTTACCTGATTGCCT TCATTGCCGGCATGGCCGTCATTGTGGATAAACCCTG GTTCTATGACATGAAGAAAGTTTGGGAGGGATATCCC ATACAGAGCACTATCCCTTCCCAGTATTGGTACTACA TGATTGAACTTTCCTTCTACTGGTCCCTGCTCTTCAG CATTGCCTCTGATGTCAAGCGAAAGGATTTCAAGGAA CAGATCATCCACCATGTGGCCACCATCATTCTCATCA GCTTTTCCTGGTTTGCCAATTACATCCGAGCTGGGAC TCTAATCATGGCTCTGCATGACTCTTCCGATTACCTG CTGGAGTCAGCCAAGATGTTTAACTACGCGGGATGGA AGAACACCTGCAACAACATCTTCATCGTCTTCGCCAT TGTTTTTATCATCACCCGACTGGTCATCCTGCCCTTC TGGATCCTGCATTGCACCCTGGTGTACCCACTGGAGC TCTATCCTGCCTTCTTTGGCTATTACTTCTTCAATTC CATGATGGGAGTTCTACAGCTGCTGCATATCTTCTGG GCCTACCTCATTTTGCGCATGCCCACAAGTTCATAA CTGGAAAGCTGGTAGAAGATGAACGCAGTGACCGGGA AGAAACAGAGAGCTCAGAGGGGAGGAGGCTGCAGCT GGGGGAGGAGCAAAGAGCCGGCCCCTAGCCAATGGCC ACCCCATCCTCAATAACAACCATCGTAAGAATGACTG ACTCGAGGG |

REFERENCES

1 Kunkel, T. Rapid and efficient site-specific mutagenesis without phenotypic selection. Proc Natl Acad Sci USA 82, 488-492 (1985).

2 Ho, S., Hunt, H., Horton, R., Pullen, J. & Pease, L. Site-directed mutagenesis by overlap extension using the polymerase chain reaction. Gene 77, 51-59 (1989).

3 Landt, O., Grunert, H. & Hahn, U. A general method for rapid site-directed mutagenesis using the polymerase chain reaction. Gene 96, 125-128 (1990).

4 Cirino, P., Mayer, K. & Umeno, D. Generating mutant libraries using error-prone PCR. Methods Mol Biol 231, 3-9 (2003).

5 Stemmer, W., Crameri, A., Ha, K., Brennan, T. & Heyneker, H. Single-step assembly of a gene and entire plasmid from large is numbers of oligodeoxyribonucleotides. Gene 164, 49-53 (1995).

6 Wilson, G. Cloned restriction-modification systems—a review. Gene 74, 281-289 (1988).

7 Wilson, G. & Murray, N. Restriction and modification systems. Annu Rev Genet 25, 585-627 (1991).

8 Hartley, J., Temple, G. & Brasch, M. DNA cloning using in vitro site-specific recombination. Genome Res 10, 1788-1795 (2000).

9 Li, M. & Elledge, S. Harnessing homologous recombination in vitro to generate recombinant DNA via SLIC. Nat Methods 4, 251-256 (2007).

10. Au, L., Yang, F., Yang, W., Lo, S. & Kao, C. Gene synthesis by a LCR-based approach: high-level production of leptin-L54 using synthetic gene in *Escherichia coli*. Biochem Biophys Res Commun 248, 200-203 (1998).
11. Smith, H., Hutchison, C. r., Pfannkoch, C. & Venter, J. Generating a synthetic genome by whole genome assembly: phiX174 bacteriophage from synthetic oligonucleotides. Proc Natl Acad Sci USA 100, 15440-15445 (2003).
12. Xiong, A. et al. PCR-based accurate synthesis of long DNA sequences. Nat Protoc 1, 791-797 (2006).
13. Horton, R., Hunt, H., Ho, S., Pullen, J. & Pease, L. Engineering hybrid genes without the use of restriction enzymes: gene splicing by overlap extension. Gene 77, 61-68 (1989).
14. Coco, W. et al. DNA shuffling method for generating highly recombined genes and evolved enzymes. Nat Biotechnol 19, 354-359 (2001).
15. Gaytán, P., Yañez, J., Sánchez, F., Mackie, H. & Soberón, X. Combination of DMT-mononucleotide and Fmoc-trinucleotide phosphoramidites in oligonucleotide synthesis affords an automatable codon-level mutagenesis method. Chem Biol 5, 519-527 (1998).
16. Merkle, R. C. Convergent assembly. Nanotechnology 8, 18-22 (1997).
17. Xiong, A. S. et al. A simple, rapid, high-fidelity and cost-effective PCR-based two-step DNA synthesis method for long gene sequences. Nucleic Acids Res 32, e98 (2004).
18. Tian J, Gong H, Sheng N, Zhou X, Gulari E, Gao X, Church G., Accurate multiplex gene synthesis from programmable DNA microchips. Nature 432(7020):1050-4 (2004).

While the invention has been described with respect to a limited number of embodiments, it will be appreciated that many variations, modifications and other applications of the invention may be made.

What is claimed is:

1. A method for synthesizing a target DNA molecule having a target DNA sequence from a plurality of existing input DNA molecules having a plurality of existing input DNA sequences, comprising
   a. implementing selected steps as a plurality of software instructions being executed by a computer by mapping said existing input DNA sequences to said target DNA sequence, comprising:
      1. identifying a plurality of portions of said existing input DNA sequences within said target DNA sequence therein defining a plurality of input fragments;
      2. defining boundaries and division points along said plurality of input fragments wherein each division point comprises a first and a second side;
      3. evaluating each of said division points to select a plurality of selected division points according to said plurality of input fragments;
      4. organizing said selected division points to form a mapping protocol from said plurality of input fragments to at least a portion of said target DNA, wherein said mapping protocol defines a plurality of core operations to be performed on said plurality of input fragments to form said target DNA, wherein each core operation is defined as receiving a plurality of input DNA molecules and producing an output DNA molecule, wherein said plurality of core operations is recursive and hierarchical, such that an output DNA molecule of a prior core operation forms an input DNA molecule to a subsequent core operation; and
      5. defining a plurality of oligonucleotides according to said mapping protocol;
   b. synthesizing said plurality of oligonucleotides defined from said plurality of input fragments with a DNA synthesizer to form synthesized oligonucleotides, wherein said oligonucleotides are at least 15 nucleotides in length;
   c. providing said plurality of existing input DNA molecules determined from said plurality of input fragments; and
   d. implementing a plurality of steps with said synthesized oligonucleotides and said plurality of existing input DNA molecules as input DNA molecules in vitro according to said mapping protocol by:
      1. performing a plurality of in vitro core operations to provide for DNA editing functions, each in vitro core operation receiving a plurality of input DNA molecules and forming an output DNA molecule, selected from the group consisting of cut, copy, paste, insert, delete, replace, substitute, cut and paste, and copy and paste, taken alone or in any combination, with the proviso that each in vitro core operation is independent of the use of site specific restriction enzyme sequences and with the proviso that each in vitro core operation is independent of the sequence of said plurality of input DNA molecules, wherein at least one in vitro core operation comprises ligation of a plurality of said input DNA molecules or polymerase integration of said plurality of input DNA molecules with annealing; and
      2. repeating said performing said plurality of in vitro core operations until said target DNA molecule is formed as said output DNA molecule wherein each in vitro core operation concatenates said input DNA molecules to form at least a portion of said target DNA molecule, and wherein each in vitro core operation is independent of the use of site specific restriction enzyme sequences.

2. The method of claim 1, wherein said mapping protocol is optimized according to factors selected from the group consisting of: available primers, time, number of core operations required, use of intermediate products for parallel use, relative size of the fragments that are concatenated; and wherein said mapping protocol comprises editing a map in the form of a binary tree of a plurality of core operations.

3. The method of claim 1 wherein each in vitro core operation comprises concatenating a first input DNA molecule to a second input DNA molecule to form at least a portion of said target DNA molecule, the method further comprising:
   a. extending said first and second input DNA molecules with a primer to form a first primer-extended input molecule and a second primer-extended input molecule comprising an overlapping region; and
   b. annealing said first and second primer-extended input molecules over said overlapping region to form an intermediate complex; and
   c. elongating said intermediate complex to form said target DNA molecule.

4. The method of claim 1, wherein said evaluating each of said division points to select a plurality of selected division points comprises:
   scoring each of said division points with a score proportional to the sum of the sizes of the largest input fragment wholly found on both sides of each division point; and providing a small penalty to each of said division points for the distance from the center of the input fragment;
   providing a penalty to each of said division points proportional to the distance from the boundary from the closest input fragment;
   and identifying and validating primers for each of said division points according to at least one primer parameter.

5. The method of claim 4 wherein said primer validation parameters are chosen from the group consisting of specificity, affinity, melting point (Tm), dimerization, amplification length, elongation length, or any combination thereof.

6. The method of claim 1 wherein said method is performed automatically.

7. The method of claim 3, wherein said primer or said input DNA sequence is selected from the group consisting of: an existing DNA sequence, an oligo comprising at least 15 base pairs and up to 100 base pairs, an oligo comprising up to 100 base pairs, an oligo comprising up to 80 base pairs, synthetic oligonucleotides, a sequence comprising an overlapping region corresponding to a portion of said first input sequence and a portion of said second input sequence.

8. The method of claim 1, wherein each of said core operations for said mapping protocol and for performing in vitro is selected from the group consisting of cut, copy, paste, cut and paste, copy and paste, taken alone or in any combination, wherein each core operation of copy and paste comprises: duplicating at least one, but not all, of a plurality of parts of a first polynucleotide to form a copied polynucleotide fragment and adding said copied polynucleotide fragment to a second polynucleotide by concatenation or insertion; wherein each core operation of cut comprises removing at least one, but not all, of a plurality of parts of a polynucleotide to form a cut polynucleotide fragment; wherein each core operation of cut and paste comprises removing at least one, but not all, of a plurality of parts of a first polynucleotide to form a cut polynucleotide fragment and adding said cut polynucleotide fragment to a second polynucleotide by concatenation or insertion; wherein each core operation of copy comprises duplicating at least one, but not all, of a plurality of parts of a polynucleotide to form a copied polynucleotide fragment; and wherein each core operation of paste comprises adding a first polynucleotide to a second polynucleotide by concatenation or insertion.

9. The method of claim 1, further comprising producing a library of target DNA molecules, comprising repeating the above stages for a plurality of target DNA molecules, wherein said mapping said input DNA sequences to said target DNA sequence comprises mapping said input DNA sequences to a plurality of target DNA sequences such that said plurality of target DNA sequences comprises a plurality of shared DNA sequences and such that said mapping said input DNA sequences comprises determining said input DNA molecules for said core operations such that said input DNA molecules have nucleotide sequences comprising said plurality of shared DNA sequences.

10. The method of claim 9, wherein said mapping said input DNA sequences comprises determining said input DNA molecules for said core operations such that said input DNA molecules are reused for constructing said plurality of target DNA molecules.

11. The method of claim 8, wherein said core operation comprises
   editing existing input DNA sequences molecules to form at least a portion of a targeted DNA sequence molecule, wherein said editing includes at least one or more functions selected from the group consisting of: cut, copy, paste, insert, delete, replace, substitute, cut and paste, copy and paste, or any combination thereof.

12. The method of claim 1, wherein said evaluating each of said division points to select a plurality of selected division points according to said plurality of input fragments comprises examining said first side and said second side of each division point to determine a concatenation operation for joining said first side and said second side; recursively determining a plurality of division points for said first side and said second side, and examining said first side and said second side to determine said concatenation operation; comparing said plurality of input fragments to each of said first sides and said second sides; and selecting said selected division points according to said comparing said plurality of input fragments to each of said first sides and said second sides.

13. The method of claim 12, wherein said comparing said plurality of input fragments to each of said first sides and said second sides further comprises scoring each of said division points according to a size of two largest input fragments for said first and second sides.

14. The method of claim 13, wherein said scoring each of said division points further comprises penalizing each of said division points according to a distance from each input fragment to said boundaries.

15. The method of claim 14, wherein said scoring each of said division points further comprises penalizing each of said division points according to a distance from each division point to said boundaries.

16. A method for synthesizing a target DNA molecule having a target DNA sequence from a plurality of existing input DNA molecules having a plurality of existing input DNA sequences, comprising
   a. creating a mapping protocol by implementing selected steps as a plurality of software instructions being executed by a computer, comprising:
      1. identifying a plurality of portions of said existing input DNA sequences within said target DNA sequence therein defining a plurality of existing input fragments;
      2. determining a plurality of existing input DNA sequences and oligonucleotide sequences to be synthesized for constructing said target DNA sequence;
      3. creating a mapping protocol to construct said target DNA sequence from said existing input DNA sequences and said oligonucleotide sequences to be synthesized;
   b. synthesizing said plurality of oligonucleotides defined from said oligonucleotide sequences with a DNA synthesizer, wherein said oligonucleotides are at least 15 nucleotides in length;

c. providing said plurality of existing input DNA molecules determined from said plurality of existing input fragments; and
d. implementing a plurality of steps with said oligonucleotides and said plurality of existing input DNA molecules as input DNA molecules in vitro according to said mapping protocol by:
  1. performing a plurality of in vitro core operations to provide for DNA editing functions, each in vitro core operation receiving a plurality of input DNA molecules and forming an output DNA molecule, selected from the group consisting of cut, copy, paste, insert, delete, replace, substitute, cut and paste, and copy and paste, taken alone or in any combination, with the proviso that each in vitro core operation is independent of the use of site specific restriction enzyme sequences and with the proviso that each in vitro core operation is independent of the sequence of said plurality of input DNA molecules, wherein at least one in vitro core operation comprises ligation of a plurality of said input DNA molecules or polymerase integration of said plurality of input DNA molecules with annealing, wherein said in vitro core operations are defined according to said mapping protocol; and
  2. repeating said performing said plurality of in vitro core operations until said target DNA molecule is formed as said output DNA molecule wherein each in vitro core operation concatenates said input DNA molecules to form at least a portion of said target DNA molecule, and wherein each in vitro core operation is independent of the use of site specific restriction enzyme sequences.

\* \* \* \* \*